United States Patent
Campana et al.

(10) Patent No.: US 11,648,269 B2
(45) Date of Patent: May 16, 2023

(54) T CELL RECEPTOR-DEFICIENT CHIMERIC ANTIGEN RECEPTOR T-CELLS AND METHODS OF USE THEREOF

(71) Applicant: National University of Singapore, Singapore (SG)

(72) Inventors: Dario Campana, Singapore (SG); Takahiro Kamiya, Tokyo (JP)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 433 days.

(21) Appl. No.: 16/100,117

(22) Filed: Aug. 9, 2018

(65) Prior Publication Data

US 2019/0046571 A1 Feb. 14, 2019

Related U.S. Application Data

(60) Provisional application No. 62/543,735, filed on Aug. 10, 2017.

(51) Int. Cl.
| | |
|---|---|
| *A61K 35/17* | (2015.01) |
| *A61K 39/00* | (2006.01) |
| *C07K 16/28* | (2006.01) |
| *A61P 35/02* | (2006.01) |
| *A61P 37/06* | (2006.01) |
| *C12N 5/0783* | (2010.01) |
| *C12N 15/62* | (2006.01) |
| *A61K 35/12* | (2015.01) |

(52) U.S. Cl.
CPC ............ *A61K 35/17* (2013.01); *A61K 39/001* (2013.01); *A61K 39/0008* (2013.01); *A61K 39/001111* (2018.08); *A61K 39/001112* (2018.08); *A61P 35/02* (2018.01); *A61P 37/06* (2018.01); *C07K 16/2803* (2013.01); *C07K 16/2809* (2013.01); *C12N 5/0636* (2013.01); *C12N 15/62* (2013.01); *A61K 2035/122* (2013.01); *A61K 2039/505* (2013.01); *A61K 2039/5156* (2013.01); *A61K 2039/5158* (2013.01); *C07K 2317/56* (2013.01); *C07K 2317/622* (2013.01); *C07K 2319/02* (2013.01); *C07K 2319/03* (2013.01); *C07K 2319/04* (2013.01); *C07K 2319/32* (2013.01); *C07K 2319/33* (2013.01)

(58) Field of Classification Search
CPC ............ A61K 35/17; A61K 39/001111; A61K 39/001112; A61K 39/0008; A61K 39/001; A61P 37/06; A61P 35/02; C07K 16/2803; C07K 16/2809; C12N 5/0636; C12N 15/62
See application file for complete search history.

(56) References Cited

U.S. PATENT DOCUMENTS

| | | | |
|---|---|---|---|
| 7,887,805 B2 | 2/2011 | Pedersen et al. | |
| 8,119,775 B2 | 2/2012 | Moretta et al. | |
| 8,399,645 B2 | 3/2013 | Campana et al. | |
| 8,580,714 B2 | 11/2013 | Almagro et al. | |
| 8,637,258 B2 | 1/2014 | Padkjaer et al. | |
| 8,796,427 B2 | 8/2014 | Spee et al. | |
| 8,981,065 B2 | 3/2015 | Moretta et al. | |
| 9,181,527 B2 | 11/2015 | Sentman | |
| 9,273,283 B2 | 3/2016 | Sentman | |
| 9,422,368 B2 | 8/2016 | Spee et al. | |
| 9,683,042 B2 | 6/2017 | Lee et al. | |
| 9,902,936 B2 | 2/2018 | Moretta et al. | |
| 10,730,942 B2 | 8/2020 | Pule et al. | |
| 10,765,699 B2 | 9/2020 | Campana et al. | |
| 2006/0034834 A1 | 2/2006 | Marasco et al. | |
| 2007/0036773 A1 | 2/2007 | Cooper et al. | |
| 2009/0196850 A1 | 8/2009 | Romagne et al. | |
| 2012/0282256 A1 | 11/2012 | Campana et al. | |
| 2013/0287748 A1 | 10/2013 | June et al. | |
| 2014/0120622 A1 | 5/2014 | Gregory | |
| 2014/0186387 A1 | 7/2014 | Lauer | |
| 2016/0256488 A1 | 9/2016 | Wu | |
| 2016/0312182 A1 | 10/2016 | Sentman | |
| 2017/0335331 A1 | 11/2017 | Zhao et al. | |
| 2018/0008638 A1 | 1/2018 | Campana et al. | |
| 2018/0066034 A1* | 3/2018 | Ma ........................ | A61K 48/00 |

(Continued)

FOREIGN PATENT DOCUMENTS

| | | |
|---|---|---|
| CA | 2 937 157 A1 | 1/2018 |
| EP | 2247619 A1 | 11/2010 |

(Continued)

OTHER PUBLICATIONS

Lorentzen et al. "CD19-Chimeric Antigen Receptor T Cells for Treatment of Chronic Lymphocytic Leukaemia and Acute Lymphoblastic Leukaemia", Scand J Immunol. Oct. 2015;82(4):307-19 (Year: 2015).*
The Merck Manuals Online Medical Library, [online]. Merck Research Laboratories, 2006-2007. [retrieved on Oct. 19, 2020]. < URL: https://www.merckmanuals.com/professional/hematology-and-oncology/overview-of-cancer/cellular-and-molecular-basis-of-cancer >. Cellular and Molecular Basis of Cancer (Year: 2020).*
Li-Lian et al. "Molecular Mechanisms and Potential Therapeutic Reversal of Pancreatic Cancer-Induced Immune Evasion", Cancers 12.7: 1872 (Year: 2020).*

(Continued)

Primary Examiner — Amy E Juedes
Assistant Examiner — Peter Johansen
(74) Attorney, Agent, or Firm — Wilson Sonsini Goodrich & Rosati

(57) ABSTRACT

The present invention provides compositions comprising a protein expression blocker or PEBL comprising a target-binding molecule and localizing domain, and methods of using such compositions in cancer therapy. PEBLs are useful as a blockade of expression of target surface receptors (peptides or antigens) in immune cells. Also provided herein are CD3/TCRαβ-deficient T cells and CD3/TCRαβ-deficient chimeric antigen receptor T cells that express such PEBLs.

16 Claims, 19 Drawing Sheets

Specification includes a Sequence Listing.

(56) References Cited

U.S. PATENT DOCUMENTS

| | | | |
|---|---|---|---|
| 2018/0086831 | A1* | 3/2018 | Pule ................. A61K 39/0011 |
| 2019/0002912 | A1 | 1/2019 | Lu et al. |
| 2019/0038733 | A1 | 2/2019 | Campana et al. |
| 2019/0345217 | A1 | 11/2019 | Ma et al. |
| 2020/0087398 | A1 | 3/2020 | Qasim et al. |
| 2021/0046112 | A1 | 2/2021 | Campana et al. |
| 2022/0347219 | A1 | 11/2022 | Campana et al. |

FOREIGN PATENT DOCUMENTS

| | | |
|---|---|---|
| EP | 3169773 A2 | 5/2017 |
| EP | 3322801 A1 | 5/2018 |
| EP | 3359168 A1 | 8/2018 |
| EP | 3474867 A1 | 5/2019 |
| EP | 3568467 A1 | 11/2019 |
| JP | H03219896 A | 9/1991 |
| JP | H09501824 A | 2/1997 |
| JP | 2001516766 A | 10/2001 |
| JP | 2008506368 A | 3/2008 |
| JP | 2008518021 A | 5/2008 |
| JP | 2009511495 A | 3/2009 |
| JP | 2010537671 A | 12/2010 |
| JP | 2011510047 A | 3/2011 |
| JP | 2014507118 A | 3/2014 |
| JP | 6895380 B2 | 6/2021 |
| WO | WO 99/14353 A2 | 3/1999 |
| WO | WO 03/051926 A2 | 6/2003 |
| WO | WO-2005017163 A2 | 2/2005 |
| WO | WO-2006003179 A2 | 1/2006 |
| WO | WO-2009092805 A1 | 7/2009 |
| WO | WO 2012/079000 A1 | 6/2012 |
| WO | WO-2014011984 A1 | 1/2014 |
| WO | WO 2014/124143 A1 | 8/2014 |
| WO | WO 2015/075468 A1 | 5/2015 |
| WO | WO 2015/150771 A1 | 10/2015 |
| WO | WO 2016/055551 A1 | 4/2016 |
| WO | WO 2016/102965 A1 | 6/2016 |
| WO | WO 2016/126213 A1 | 8/2016 |
| WO | WO 2017/213979 A1 | 12/2017 |
| WO | WO 2018/027036 A1 | 2/2018 |
| WO | WO-2019032916 A1 | 2/2019 |

OTHER PUBLICATIONS

Kotteas et al. "Immunotherapy for pancreatic cancer", Journal of Cancer Research & Clinical Oncology, 142.8: 1795-1805. (Year: 2016).*
Böldicke et al. "Functional inhibition of transitory proteins by intrabody-mediated retention in the endoplasmatic reticulum", (Methods. Mar. 2012;56(3):338-50). (Year: 2012).*
Clift, Dean, et al "A Method for the Acute and Rapid Degradation of Endogenous Proteins", Elsevier Inc., Cell 172, Dec. 14, 2017, pp. 1692-1706.
Marschall, Andrea LJ, et al "Specific in vivo knockdown of protein function by intrabodies", Taylor & Francis Group, LLC, Nov./Dec. 2015, vol. 7, Issue 6, pp. 1010-1035.
Arase, Hisashi, et al. "Recognition of virus infected cells by NK cells", Department of Immunochemistry, Research Institute for Microbial Diseases, Osaka University, vol. 54, No. 2, pp. 153-160.
Milone, Michael C., et al. "Chimeric Receptors Containing CD137 Signal Transduction Domains Mediate Enhanced Survival of T Cells and Increased Antileukemic Efficacy In Vivo," Mol. Ther., 2009, vol. 17, No. 8, pp. 1453-1464.
XP-002784541 "A simple protein-based method for generation of 'off the shelf' allogeneic chimeric antigen receptor T-cells", Journal Conference Abstract, Molecular Therapy, May 1, 2018, vol. 26, No. 5, pp. 296-297.
Böldicke, Thomas, "Blocking translocation of cell surface molecules from the ER to the cell surface by intracellular antibodies targeted to the ER", J. Cell. Mol. Med., vol. 11, No. 1, 2007, pp. 54-70.
Hegde, M. et al., "Combinational targeting offsets antigen escape and enhances effector functions of adoptively transferred T cells in glioblastoma", Molecular Therapy, 2013, vol. 21, pp. 2087-2101.

Imamura. M. et al., "Autonomous growth and increased cytotoxicity of natural killer cells expressing membrane-bound interleukin-15", Blood, 2014, vol. 124, pp. 1081-1088.
Kamiya, et al., A novel method to generate T-cell receptor-deficient antigen receptor T cells, Blood Advances, vol. 2, No. 5, Mar. 13, 2018, pp. 517-528.
Kloss, C.C. et al., "Combinatorial antigen recognition with balanced signaling promotes selective tumor eradication by engineered T cells", Nature Biotechnology, 2013, vol. 31, pp. 71-75.
Kudo, K. et al., "T lymphocytes expressing a CD16 signaling receptor exert antibody dependent cancer cell killing". Cancer Research, 2014, vol. 74, pp. 93-103.
Lantis, E. et al., "Chimeric antigen receptor T Cells with dissociated signaling domains exhibit focused antitumor activity with reduced potential for toxicity in vivo", Cancer Immunology Research, 2013, vol. 1, pp. 43-53.
Lo, A.S.Y. et al., "Harnessing the tumour-derived cytokine, CSF-1, to co-stimulate Tcell growth and activation", Molecular Immunology, 2008, vol. 45, pp. 1276-1287.
Png, Yi Tian, et al., "Blockade of CD7 expression in T cells for effective chimeric antigen receptor targeting of T-cell malignancies", 2017, Blood Advances, vol. 1, pp. 2348-2360.
Rossig, C. et al., "Genetic modification of T lymphocytes for adoptive immunotherapy", Molecular Therapy, 2004, vol. 10, pp. 5-18.
Rowley, J. et al., "Expression of IL-15RA or an IL-15/IL-15RA fusion on CD8+ T cells modifies adoptively transferred T-cell function in cis", European Journal of Immunology, 2009, vol. 39, pp. 491-506.
Sanz, L. et al., "Antibodies and gene therapy: teaching old 'magic bullets' new tricks", Trends in Immunology, 2004, vol. 25, pp. 85-91.
Zhou, P. et al., "Cells transfected with a non-neutralizing antibody gene are resistant to HIV infection: targeting the endoplasmic reticulum and trans-Golgi network", The Journal of Immunology, 1998, vol. 160, pp. 1489-1496.
Grimshaw, Benjamin David "Developing a universal T cell for use in adoptive immunotherapy", XP055493578, Jan. 1, 2015, pp. 190-197, retrieved from internet: URL:http://discovery.ucl.ac.uk/1470207/1/Grimshaw%20Ben%20Thesis.pdf.
Alanen et al., Beyond KDEL: the role of positions 5 and 6 in determining ER localization. J. Mol. Biol. (2011) 409, 291-297. Available online Apr. 6, 2011.
Alarcon et al., Assembly of the human T cell receptor-CD3 complex takes place in the endoplasmic reticulum and involves intermediary complexes between the CD3-gamma.delta.epsilon core and single T cell receptor alpha or beta chains, Journal of Biological Chemistry, Feb. 25, 1988;263(6):2953-61.
Anti-CD3 epsilon [OKT-3 (muromonab)]. Absolute Antibody. Website. Copyright 2021. Retrieved Dec. 26, 2021 at URL : https://absoluteantibody.com/product/anti-cd3-epsilon-okt-3- . . . 4 pages.
Anti-CD3D monoclonal antibody, clone PLU4 (DCABH-10124). Product Information. CD Creative Diagnostics. Publication date unknown. 2 pages.
Anti-TCR [BMA031]. Absolute Antibody. Website. Copyright 2021. Retrieved Dec. 26, 2021 at URL: https://absoluteantibody.com/product/anti-tcr-bma031/ 4 pages.
Anwer et al., Donor origin CAR T cells: graft versus malignancy effect without GVHD, a systematic review, Immunotherapy, Jan. 2017;9(2):123-130.
Appelbaum. Haematopoietic cell transplantation as immunotherapy. Nature, vol. 411, pp. 385-389 (2001).
Arafat et al. Antineoplastic effect of anti-erbB-2 intrabody is not correlated with scFv affinity for its target. Cancer Gene Therapy, vol. 7, No. 9, 2000: pp. 1250-1256.
Boettcher et al., Choosing the Right Tool for the Job: RNAi, TALEN, or CRISPR, Mol Cell. May 21, 2015;58:575-85.
Brentjens et al. CD19-targeted T cells rapidly induce molecular remissions in adults with chemotherapy-refractory acute lymphoblastic leukemia. Sci Transl Med. Mar. 20, 2013;5(177):177ra38. 9 pages.
Brentjens et al. Safety and persistence of adoptively transferred autologous CD19-targeted T cells in patients with relapsed or

(56) References Cited

OTHER PUBLICATIONS chemotherapy refractory B-cell leukemias. Blood. Nov. 3, 2011;118(18):4817-28. Prepublished online Aug. 17, 2011.
Brudno et al. Allogeneic T cells that express an anti-CD19 chimeric antigen receptor induce remissions of B-cell malignancies that progress after allogeneic hematopoietic stem-cell transplantation without causing graft-versus-host disease. J Clin Oncol 34(10):1112-1121 (2016).
Campana et al. 4-1BB chimeric antigen receptors. Cancer J. Mar.-Apr. 2014;20(2):134-40.
Chang et al. A chimeric receptor with NKG2D specificity enhances natural killer cell activation and killing of tumor cells. Cancer Res 73(6):1777-86 (Mar. 15, 2013). Published online Jan. 9, 2013.
Chen et al., Donor-derived CD19-targeted T cell infusion induces minimal residual disease-negative remission in relapsed B-cell acute lymphoblastic leukaemia with no response to donor lymphocyte infusions after haploidentical haematopoietic stem cell transplantation. British Journal of Haematology, 2017, 179, 598-605. Epub Oct. 26, 2017.
Clevers et al., The T cell receptor/CD3 complex: a dynamic protein ensemble, Annual Review of Immunology, 1988;6:629-62.
Cooley et al. Donor selection for natural killer cell receptor genes leads to superior survival after unrelated transplantation for acute myelogenous leukemia. Blood (2010) 116 (14): 2411-2419.
Dai et al., Tolerance and efficacy of autologous or donor-derived T cells expression CD19 chimeric antigen receptors in adult B-ALL with extramedullary leukemia. OncoImmunology, 4:11, e1027469 (2015). 12 pages.
Davila. Efficacy and toxicity management of 19-28z CAR T cell therapy in B cell acute lymphoblastic leukemia. Sci Transl Med 6(224):224ra25 (2014).
Dotti et al. Design and Development of Therapies using Chimeric Antigen Receptor-Expressing T cells. Immunol Rev. 257(1):35 pgs (2014).
EP16746922.0 Extended European Search Report dated Sep. 21, 2018.
EP18844536.5 Extended European Search Report dated Mar. 18, 2021.
Eyquem et al., Targeting a CAR to the TRAC locus with CRISPR/Cas9 enhances tumour rejection, Nature. Mar. 2, 2017; 543(7643): 113-117.
Gao et al. Retention mechanisms for ER and Golgi membrane proteins. Trends in Plant Science, vol. 19, Issue 8, pp. 508-515 (Aug. 2014).
Geiger et al. Integrated src kinase and costimulatory activity enhances signal transduction through single-chain chimeric receptors in T lymphocytes. Blood 98(8):2364-2371 (2001).
Ghosh et al., Donor CD19 CAR T cells exert potent graft-versus-lymphoma activity with diminished graft-versus-host activity, Nat Med. Feb. 2017 ; 23(2): 242-249.
Giebel et al. Survival advantage with KIR ligand incompatibility in hematopoietic stem cell transplantation from unrelated donors. Blood (2003) 102 (3): 814-819.
Grimshaw, B.D. et al., BGST Abstract Mar. 9, 2012, abstract P023, "Creating a 'null' T cell for use in adoptive immunotherapy", British Society for Gene and Cell Therapy 2012, http://www.bsqct.orq, Human Gene Therapy, 22 pages.
Grimshaw et al. Creating a Null T Cell for Adoptive Immunotherapy. Poster. Mar. 9, 2012. One page.
Grovender et al. Single-chain antibody fragment-based adsorbent for the extracorporeal removal of β2-microglobulin. Kidney International, vol. 65 (2004), pp. 310-322.
Grupp et al. Chimeric Antigen Receptor-Modified T Cellsfor Acute Lymphoid Leukemia. N Engl J Med 368;16, pp. 1509-1508 (Apr. 18, 2013). With correction published N. Engl J. Med (2016) 374(10) 998.
Haynes et al. Rejection of syngeneic colon carcinoma by CTLs expressing single-chain antibody receptors codelivering CD28 costimulation. J Immunol 2002; 169:5780-5786.

Haynes et al. Single-chain antigen recognition receptors that costimulate potent rejection of established experimental tumors. Blood. Nov. 1, 2002;100(9):3155-63. Published online Jul. 5, 2002.
Hegde, M. et al., Supplementary Material for "Combinational targeting offsets antigen escape and enhances effector functions of adoptively transferred T cells in glioblastoma", Molecular Therapy, 2013, vol. 21, pp. 2087-2101. Retrieved Jan. 6, 2022 from URL: https://ars.els-cdn.com/content/image/1-s2.0-S1525001616309315-mmc1.pdf. 9 pages.
Hombach et al. Tumor-Specific T Cell Activation by Recombinant Immunoreceptors: CD3ζ Signaling and CD28 Costimulation Are Simultaneously Required for Efficient IL-2 Secretion and Can Be Integrated Into One Combined CD28/CD3ζ Signaling Receptor Molecule. J Immunol 2001; 167:6123-6131.
Imai et al. Chimeric receptors with 4-1BB signaling capacity provoke potent cytotoxicity against acute lymphoblastic leukemia. Leukemia (2004) 18, 676-684.
Imai et al. Genetic modification of primary natural killer cells overcomes inhibitory signals and induces specific killing of leukemic cells. Blood (2005) 106 (1): 376-383.
<img>Imamura. M. et al., Supplementary Material for "Autonomous growth and increased cytotoxicity of natural killer cells expressing membrane-bound interleukin-15", Blood, 2014, vol. 124, pp. 1081-1088. Retrieved Jan. 6, 2021 at URL: https://ash.silverchair-cdn.com/ash/content_public/journal/blood/124/7/10.1182_blood-2014-02-556837/4/blood-2014-02-556837-1.pdf?Expires=1644340511&Signature=uyyKt0KS8WtXpVUILTgok2Ryynm zBJgE2vCNIDD4xdwCv13vsg0goCLOpQLU~KVPtlTvlHtmCLeX 2MhA7mcxzXy~ydDqrj6rHeZEBNohY4NOkmjpH9529c9SCChM FB1n80TH-cM-MgQfrETegs4oK6vjiveJODaZP6TfW1gGK~5JUA n5LesZfPv9W28NmBfMoAOMVeX4Pz54V~9dWaBcCfXCR7vO rx1N8cpbxmlAumSziwKqxNCy79dwOL6ddz3joiyKtMiGNuY1c6 I1f6b~MwbLxZ3jKI6EE-giQZhSxfLm2ctwuCbOMj8RIHCM4cO5a2zIKMAM6dut-dafGbQaRQ_&Key-Pair-Id=APKAIE5G5CRDK6RD3PGA. 11 pages.
Jackson et al., Identification of a consensus motif for retention of transmembrane proteins in the endoplasmic reticulum, EMBO J. Oct. 1990; 9(10): 3153-3162.
Joshi et al. Fusion to a highly charged proteasomal retargeting sequence increases soluble cytoplasmic expression and efficacy of diverse anti-synuclein intrabodies. mAbs, vol. 4, Issue 6, pp. 686-693 (2012). Published online: Aug. 28, 2012.
Kalos, et al., "T Cells with Chimeric Antigen Receptors Have Potent Antitumor Effects and Can Establish Memory in Patients with Advanced Leukemia", Science Translation Medicine 3.95 (2011):95ra73-95ra73.
Kamiya et al. Blocking expression of inhibitory receptor NKG2A overcomes tumor resistance to NK cells. J Clin Invest. 2019;129(5):2094-2106.
Kloss, C.C. et al., Supplementary Text and Figures for "Combinatorial antigen recognition with balanced signaling promotes selective tumor eradication by engineered T cells", Nature Biotechnology, 2013, vol. 31, pp. 71-75. Retrieved Jan. 6, 2021 at URL: https://static-content.springer.com/esm/art%3A10.1038%2Fnbt.2459/MediaObjects/41587_2013_BFnbt2459_MOESM2_ESM.pdf. 5 pages.
Kochenderfer et al. B-cell depletion and remissions of malignancy along with cytokine-associated toxicity in a clinical trial of anti-CD19 chimeric-antigen-receptor-transduced T cells. Blood. 2012;119(12):2709-2720. Published online Dec. 8, 2011.
Kochenderfer et al., Chemotherapy-refractory diffuse large B-cell lymphoma and indolent B-cell malignancies can be effectively treated with autologous T cells expressing an anti-CD19 chimeric antigen receptor, Journal of Clinical Oncology, Feb. 20, 2015; 33(6); pp. 540-549. Published online Aug. 25, 2014.
Kochenderfer et al., Donor-derived CD19-targeted T cells cause regression of malignancy persisting after allogeneic hematopoietic stem cell transplantation, Blood. 2013;122(25):4129-4139.
Kolb et al. Graft-versus-leukemia effect of donor lymphocyte transfusions in marrow grafted patients. Blood, vol. 86. No. 5 (Sep. 1, 1995): pp. 2041-2050.

(56) References Cited

OTHER PUBLICATIONS

Zhan et al. Modification of ricin A chain, by addition of endoplasmic reticulum (KDEL) or Golgi (YQRL) retention sequences, enhances its cytotoxicity and translocation. Cancer Immunology, Immunotherapy. vol. 46, pp. 55-60 (1998).

Lee, et al. Current concepts in the diagnosis and management of cytokine release syndrome. Blood. Jul. 10, 2014;124(2):188-95. doi: 10.1182/blood-2014-05-552729. Epub May 29, 2014.

Lee et al., T cells expressing CD 19 chimeric antigen receptors for acute lymphoblastic leukaemia in children and young adults: a phase 1 dose-escalation trial. Lancet, Feb. 7, 2015; 385 (9967); pp. 517-528. Epub Oct. 13, 2014.

Maciocia et al. A simple protein-based method for generation of 'off the shelf' allogeneic chimeric antigen receptor T-cells. DATABASE EMBASE [Online] 1-15, Elsevier Science Publishers, Amsterdam, NL (May 1, 2018). Abstract. XP002784541. Database Accession No. EMB-623339718.

Maciocia et al. A simple protein-based method for generation of 'off the shelf' allogeneic chimeric antigen receptor T-cells. Molecular Therapy, vol. 26, No. 5, Supplement 1, pp. 296-297 (May 2018). Cell Press NLD. May 16, 2018 to May 19, 2018 Chicago, IL-297 Conf. ISSN: 1525-0024.

Macleod et al., Integration of a CD19 CAR into the TCR Alpha Chain Locus Streamlines Production of Allogeneic Gene-Edited CAR T Cells, Molecular Therapy, vol. 25, No. 4, pp. 949-961, Apr. 2017.

Maher et al. Human T-lymphocyte cytotoxicity and proliferation directed by a single chimeric TCRzeta /CD28 receptor. Nat Biotech 20(1):70-75 (2002).

Marasco et al. Design, intracellular expression, and activity of a human anti-human immunodeficiency virus type 1 gp120 single-chain antibody. PNAS USA 90:7889-7893 (1993).

Maude, et al., "Chimeric Antigen Receptor T Cells for Sustained Remissions in Leukemia" N. Engl J. Med (2014) 371(16) 1507-1517. With correction published N. Engl J. Med (2016) 374(10) 998.

Miller et al. Successful adoptive transfer and in vivo expansion of human haploidentical NK cells in patients with cancer. Blood 105:3051-3057 (2005).

Miller. Therapeutic applications: natural killer cells in the clinic. Hematology Am Soc Hematol Educ Program (2013) 2013 (1): 247-253.

Munro et al., A C-terminal signal prevents secretion of luminal ER proteins, Cell. Mar. 13, 1987;48:899-907. Retrieved Apr. 7, 2022 at URL: https://bio.davidson.edu/molecular/MunPelham/mufixed.html.

Kochenderfer et al., Eradication of B-lineage cells and regression of lymphoma in a patient treated with autologous T cells genetically engineered to recognize CD19 (Blood, 2010, 116:4099-4102) (Year: 2010).

Neelapu et al., Axicabtagene Ciloleucel CAR T-Cell Therapy in Refractory Large B-Cell Lymphoma, N Engl J Med 377;26 pp. 2531-2544 (Dec. 28, 2017).

Pardoll. The blockade of immune checkpoints in cancer immunotherapy. Nat Rev Cancer. 12(4):252-264 (2012).

Park et al. Are all chimeric antigen receptors created equal? J Clin Oncol. Feb. 20, 2015;33(6):651-3. Epub Jan. 20, 2015.

Park et al., CD19-targeted CAR T-cell therapeutics for hematologic malignancies: interpreting clinical outcomes to date, Blood. 2016;127(26):3312-3320.

PCT/SG2016/050063 International Search Report and Written Opinion dated May 9, 2016.

PCT/US2018/046137 International Search Report and Written Opinion dated Oct. 29, 2018.

Pearson and Lipman, Improved tools for biological sequence comparison, Proc. Nat. Acad Sci USA., 85:2444-2448, (1988).

Peipp et al. A Recombinant CD7-specific Single-Chain Immunotoxin Is a Potent Inducer of Apoptosis in Acute Leukemic T Cells. Cancer Research 62, pp. 2848-2855 (May 15, 2002).

Poirot et al. Multiplex Genome-Edited T-cell Manufacturing Platform for Off-the-ShelfAdoptive T-cell Immunotherapies. Cancer Research 75(18):3853-3864 (2015).

Porter et al., Chimeric antigen receptor-modified T cells in chronic lymphoid leukemia. N Engl J Med 365:725-733 (2011). With correction published N. Engl J. Med (2016) 374(10) 998.

Porter et al. Induction of Graft-versus-Host Disease as Immunotherapy for Relapsed Chronic Myeloid Leukemia. N Engl J Med 1994; 330:100-106.

Qasim et al., Molecular remission of infant B-ALL after infusion of universal TALEN gene-edited CART cells. Sci. Transl. Med. 9, eaaj2013 (2017). With Erratum. Erratum retrieved Apr. 7, 2022 at URL: https://www.science.org/doi/10.1126/scitranslmed.aam9292. 3 pages.

Reshef et al. Blockade of lymphocyte chemotaxis in visceral graft-versus-host disease. N Engl J Med 367;3 pp. 135-145 (Jul. 12, 2012).

Rosenberg et al. Adoptive cell transfer as personalized immunotherapy for human cancer. Science 348(6230):62-68 (2015).

Rowley, J. et al., Supplementary Information for "Expression of IL-15RA or an IL-15/IL-15RA fusion on CD8+ T cells modifies adoptively transferred T-cell function in cis", European Journal of Immunology, 2009, vol. 39, pp. 491-506. Retrieved Jan. 6, 2022 at URL: https://onlinelibrary.wiley.com/action/downloadSupplement?doi=10.1002%2Feji.200838594&file=eji_200838594_sm_SupplInfoFig.pdf. 6 pages.

Rubnitz et al. NKAML: A Pilot Study to Determine the Safety and Feasibility of Haploidentical Natural Killer Cell Transplantation in Childhood Acute Myeloid Leukemia. J Clin Oncol. Feb. 20, 2010; 28(6): 955-959.

Ruggeri et al. Effectiveness of donor natural killer cell alloreactivity in mismatched hematopoietic transplants. Science 295(5562):2097-2100 (2002).

Sadelain et al. The Basic Principles of Chimeric Antigen Receptor Design. Cancer Discov. Apr. 2013; 3(4): 388-398.

Sadelain et al. Therapeutic T cell engineering. Nature 545:423-431 (2017).

Sato et al. Single domain intrabodies against WASP inhibit TCR-induced immune responses in transgenic mice T cells. Sci Rep. Oct. 21, 2013;3:3003. 10 pages.

Schumann, et al. Generation of knock-in primary human T cells using Cas9 ribonucleoproteins. Proc Natl Acad Sci USA. Aug. 18, 2015; 112(33):10437-42. doi: 10.1073/pnas.1512503112. Epub Jul. 27, 2015.

Schuster et al., Chimeric Antigen Receptor T Cells in Refractory B-Cell Lymphomas, Dec. 28, 2017,, the New England Journal of Medicine, 2017; 377; pp. 2545-2554.

Sharma et al., "Novel cancer immunotherapy agents with survival benefit: recent successes and next steps," Nat Rev Cancer, 11(11):805-812 (2011).

Shikano et al., Membrane receptor trafficking: Evidence of proximal and distal zones conferred by two independent endoplasmic reticulum localization signals, PNAS May 13, 2003 100 (10) 5783-5788.

Shimasaki et al. A clinically adaptable method to enhance the cytotoxicity of natural killer cells against B-cell malignancies. Cytotherapy, 2012; 14: 830-840.

Shimasaki et al., Natural killer cell reprogramming with chimeric immune receptors, Methods Mol Biol. 2013;969:203-20.

Slavin et al. Allogeneic cell therapy with donor peripheral blood cells and recombinant human interleukin-2 to treat leukemia relapse after allogeneic bone marrow transplantation. Blood (1996) 87 (6): 2195-2204.

Smith et al. Comparison of Biosequences. Advances in Applied Mathematics. 2:482-489 (1981).

Sommermeyer et al., Fully human CD19-specific chimeric antigen receptors for T-cell therapy. Leukemia. Oct. 2017; 31(10): 2191-2199.

Strebe et al. Functional knockdown of VCAM-1 at the post-translational level with ER retained antibodies. Journal of Immunological Methods 341 (2009) 30-40. Available online Nov. 25, 2008.

(56) References Cited

OTHER PUBLICATIONS

Su et al., CRISPR-Cas9 mediated efficient PD-I disruption on human primary T cells from cancer patients, Sci Rep 6, 20070, Published: Jan. 28, 2016. 14 pages.
Till et al. CD20-specific adoptive immunotherapy for lymphoma using a chimeric antigen receptor with both CD28 and 4-1BB domains: pilot clinical trial results. Blood 119(17):3940-3950 (2012).
Topp et al. Targeted therapy with the T-cell-engaging antibody blinatumomab of chemotherapy-refractory minimal residual disease in B-lineage acute lymphoblastic leukemia patients results in high response rate and prolonged leukemia-free survival. J Clin Oncol. Jun. 20, 2011;29(18):2493-8.
Torikai et al. A foundation for universal T-cell based immunotherapy: T cells engineered to express a CD19-specific chimeric-antigen-receptor and eliminate expression of endogenous TCR. Blood 119(24):5697-5705 (2012).
Turtle et al. CD19 CAR-T cells of defined CD4+:CD8+ composition in adult B cell ALL patients. J Clin Invest 126(6):2123-2138 (2016).
U.S. Appl. No. 15/548,577 Notice of Allowance dated May 4, 2020.
U.S. Appl. No. 15/548,577 Office Action dated Jan. 14, 2019.
U.S. Appl. No. 15/548,577 Office Action dated Jul. 20, 2018.
U.S. Appl. No. 15/548,577 Office Action dated Sep. 17, 2019.
U.S. Appl. No. 16/100,120 Office Action dated Aug. 2, 2019.
U.S. Appl. No. 16/100,120 Office Action dated Feb. 24, 2020.
U.S. Appl. No. 16/100,120 Office Action dated Jan. 28, 2019.
U.S. Appl. No. 16/100,120 Office Action dated Oct. 6, 2020.
Verneris et al. Natural Killer Cell Consolidation for Acute Myelogenous Leukemia: A Cell Therapy Ready for Prime Time? J Clin Oncol. Feb. 20, 2010; 28(6): 909-910.
Vivier, Eric et al., Innate or adaptive immunity? The example of natural killer cells, Science (New York,N.Y.) vol. 331,6013 (2011): 44-9. doi:10.1126/science.1198687.
Wheeler et al. Intrabody and intrakine strategies for molecular therapy. Molecular Therapy, vol. 8, No. 3, pp. 355-366, Sep. 2003.
Yang et al., Challenges and opportunities of allogeneic donor-derived CAR T cells, Current Opinion in Hematology, Nov. 2015; 22 (6); pp. 509-515.
Zang et al. The B7 family and cancer therapy: costimulation and coinhibition. Clin Cancer Res 13(18) pp. 5271-5279 (Sep. 15, 2007).
Austyn et al. T cell activation by anti-CD3 antibodies: function of Fc receptors on B cell blasts, but not resting B cells, and CD18 on the responding T cells. Eur J Immunol 17:1329-1335 (1987).
Ceuppens et al. Failure of OKT3 monoclonal antibody to induce lymphocyte mitogenesis: a familial defect in monocyte helper function. J Immunol, vol. 134, No. 3, pp. 1498-1502 (Mar. 1985).
Haegert et al. Co-expression of surface immunoglobulin and T3 on hairy cells. Scand J Haematol 1986;37:196-202.
Smith et al. T cell activation by anti-T3 antibodies: Comparison of IgG1 and IgG2b switch variants and direct evidence for accessory function of macrophage Fc receptors. Eur J Immunol 16:478-486 (1986).
Van Wauwe et al. Human T lymphocyte activation by monoclonal antibodies; OKT3, but not UCHT1, triggers mitogenesis via an interleukin 2-dependent mechanism. J Immunol, vol. 133, No. 1, pp. 129-132 (Jul. 1984).
Verwilghen et al. Differences in the stimulating capacity of immobilized anti-CD3 monoclonal antibodies: variable dependence on interleukin-1 as a helper signal for T-cell activation. Immunology 72:269-276 (1991).
Wang et al. Expression and characterization of recombinant soluble monkey CD3 molecules: mapping the FN18 polymorphic epitope. Molecular Immunology 40:1179-1188 (2004).
Burns et al. Two monoclonal anti-human T lymphocyte antibodies have similar biologic effects and recognize the same cell surface antigen. J Immunol 1982; 129:1451-1457.
Hexham et al. Influence of relative binding affinity on efficacy in a panel of anti-CD3 scFv immunotoxins. Molecular Immunology 38 (2001) 397-408.
Weetall et al. T-cell depletion and graft survival induced by anti-human CD3 immunotoxins in human CD3ε transgenic mice. Transplantation, vol. 73, 1658-1666, No. 10 (May 27, 2002).
Wunderlich et al. OKT3 prevents xenogeneic GVHD and allows reliable xenograft initiation from unfractionated human hematopoietic tissues. Blood. 2014;123(24):e134-e144.
Almagro, Juan C., Fransson, Johan. Humanization of antibodies. Frontiers in Bioscience 13;1619-1633 (Jan. 1, 2008).
Co-pending U.S. Appl. No. 17/862,797, inventors Campana; Dario et al., filed Jul. 12, 2022.
Grimshaw. Developing a universal T cell for use in adoptive immunotherapy (thesis), University College London (2015). Retrieved Aug. 22, 2022 at URL: http://discovery.ucl.ac.Uk/1470207/1/Grimshaw%20Ben%20Thesis.pdf. 267 pages.
Kloss. Combinatorial antigen recognition with balanced signaling promotes selective tumor eradication by engineered T cells. Nature Technology, vol. 31, No. 1, pp. 71-75 (Jan. 2013). Published online Dec. 16, 2012.
Lo et al. Harnessing the tumour-derived cytokine, CSF-1, to co-stimulate T-cell growth and activation. Molecular Immunology 45 (2008) 1276-1287. Available online Oct. 24, 2007.
Rudikoff, et al. Single amino acid substitution altering antigen-binding specificity. Proc Natl Acad Sci USA. Mar. 1982;79(6):1979-83.
Score Search Results Detail for U.S. Appl. No. 17/862,721 and Search Results 20220829_091720_us-17-862-721-16.rag. Search run on Aug. 29, 2022. retrieved Aug. 30, 2022 at score.uspto.gov/ScoreAccessWeb/getItemDetail?appId=17862721&docId=bc544287-1664-44c7-9aff-7ec7ba8cb7ea&itemName=20220829_091720 . . . 14 pages.
Score Search Results Detail for U.S. Appl. No. 17/862,721 and Search Results 20220829_091720_us-17-862-721-16.rai. Search run on Aug. 29, 2022. retrieved Aug. 30, 2022 at score.uspto.gov/ScoreAccessWeb/getItemDetail?appId=17862721&docId=131a34de-dcc5-448f-b75f-7ea24f699275&itemName=20220829_091720_ . . . 8 pages.
Score Search Results Detail for U.S. Appl. No. 17/862,721 and Search Results 20220829_091720_us-17-862-721-16.rapm. Search run on Aug. 29, 2022. retrieved Aug. 30, 2022 at score.uspto.gov/ScoreAccessWeb/getItemDetail?appId=17862721&docId=e6f49583-c02c-4eee-a87c-e0ece396955c&itemName=20220829_091720 . . . 10 pages.
Score Search Results Detail for U.S. Appl. No. 17/862,721 and Search Results 20220829_091720_us-17-862-721-17.rag. Search run on Aug. 29, 2022. retrieved Aug. 30, 2022 at score.uspto.gov/ScoreAccessWeb/getItemDetail?appId=17862721&docId=cbb41ae5-1511-498f-ac7c-0b33abd2492f&itemName=20220829_091720 . . . 15 pages.
Score Search Results Detail for U.S. Appl. No. 17/862,721 and Search Results 20220829_091720_us-17-862-721-17.rai. Search run on Aug. 29, 2022. retrieved Aug. 31, 2022 at score.uspto.gov/ScoreAccessWeb/getItemDetail?appId=17862721&docId=73e892a9-d59f-4aff-8df1-883c983c2966&itemName=20220829_091720_u . . . 8 pages.
Score Search Results Detail for U.S. Appl. No. 17/862,721 and Search Results 20220829_091720_us-17-862-721-17.rapm. Search run on Aug. 29, 2022. retrieved Aug. 31, 2022 at score.uspto.gov/ScoreAccessWeb/getItemDetail?appId=17862721&docId=9851a8bc-7a77-4e69-985e-903a1f2622ae&itemName=20220829_09172 . . . 10 pages.
Score Search Results Detail for U.S. Appl. No. 17/862,721 and Search Results 20220829_091720_us-17-862-721-17.rpr. Search run on Aug. 29, 2022. retrieved Aug. 31, 2022 at score.uspto.gov/ScoreAccessWeb/getItemDetail?appId=17862721&docId=e04b2be2-c5c8-4cba-b806-cd02a1efe868&itemName=20220829_091720_ . . . 7 pages.
Score Search Results Detail for U.S. Appl. No. 17/862,721 and Search Results 20220829_091720_us-17-862-721-20.rai. Search run on Aug. 29, 2022. retrieved Aug. 31, 2022 at score.uspto.gov/ScoreAccessWeb/getItemDetail?appId=17862721&docId=d17ad86f-3b93-47e9-a94e-a9258afaa3e3&itemName=20220829_091720_ . . . 9 pages.

(56) References Cited

OTHER PUBLICATIONS

Score Search Results Detail for U.S. Appl. No. 17/862,721 and Search Results 20220829_091720_us-17-862-721-20.rapm. Search run on Aug. 29, 2022. retrieved Aug. 31, 2022 at score.uspto.gov/ScoreAccessWeb/getItemDetail?appId=17862721&docId=5747899e-d2f6-4407-8197-6ae6e43ac551&itemName=20220829_09172 . . . 11 pages.
Score Search Results Detail for U.S. Appl. No. 17/862,721 and Search Results 20220829_091720_us-17-862-721-20.rpr. Search run on Aug. 29, 2022. retrieved Aug. 31, 2022 at score.uspto.gov/ScoreAccessWeb/getItemDetail?appId=17862721&docId=8db4eb9f-566a-448b-8a1b-9244e2b8f0ee&itemName=20220829_091720_ . . . 7 pages.
Score Search Results Detail for U.S. Appl. No. 17/862,721 and Search Results 20220829_091720_us-17-862-721-21.rag. Search run on Aug. 29, 2022. retrieved Aug. 31, 2022 at score.uspto.gov/ScoreAccessWeb/getItemDetail?appId=17862721&docId=69e4190a-317d-4f26-9846-c30ab0601669&itemName=20220829_09172 . . . 14 pages.
Score Search Results Detail for U.S. Appl. No. 17/862,721 and Search Results 20220829_091720_us-17-862-721-21.rai. Search run on Aug. 29, 2022. retrieved Aug. 31, 2022 at score.uspto.gov/ScoreAccessWeb/getItemDetail?appId=17862721&docId=a9c72e86-3699-4e4c-8110-8367d0fe6cf4&itemName=20220829_091720_ . . . 8 pages.
U.S. Appl. No. 17/862,721 Office Action dated Sep. 7, 2022.
Score Search Results Details for U.S. Appl. No. 15/548,577 and Search Result 20190107_143513_us-15-548-577-37.rag. Search run on Jan. 7, 2019. retrieved Sep. 11, 2019 at http://score.uspto.gov/ScoreAccessWeb/getItem.htm?AppId=15548577&seqId=09323b67 . . . 4 pages.
Score Search Results Details for U.S. Appl. No. 15/548,577 and Search Result 20190107_143514_us-15-548-577-36.rapbm. Search run on Jan. 7, 2019. retrieved Sep. 11, 2019 at http://score.uspto.gov/ScoreAccessWeb/getItem.htm?AppId=15548577&seqId=09323b67 . . . 4 pages.
Score Search Results Details for U.S. Appl. No. 15/548,577 and Search Result 20190107_143513_us-15-548-577-37.rag. Search run on Jan. 7, 2019. retrieved Jan. 8, 2019 at http://score.uspto.gov/ScoreAccessWeb/getItem.htm?AppId=15548577&seqId=09323b678 . . . 21 pages.
Score Search Results Details for U.S. Appl. No. 15/548,577 and Search Result 20190107_143514_us-15-548-577-36.rapbm. Search run on Jan. 7, 2019. retrieved Jan. 8, 2019 at http://score.uspto.gov/ScoreAccessWeb/getItem.htm?AppId=15548577&seqId=09323b678 . . . 13 pages.
Score Search Results Details for U.S. Appl. No. 15/548,577 and Search Result 20190107_143514_us-15-548-577-37.rai. Search run on Jan. 7, 2019. retrieved Jan. 8, 2019 at http://score.uspto.gov/ScoreAccessWeb/getItem.htm?AppId=15548577&seqId=09323b678 . . . 11 pages.
Score Search Results Details for U.S. Appl. No. 15/548,577 and Search Result 20190107_145543_us-15-548-577-32.rag. Search run on Jan. 7, 2019. retrieved Jan. 8, 2019 at http://score.uspto.gov/ScoreAccessWeb/getItem.htm?AppId=15548577&seqId=09323b678 . . . 23 pages.
Score Search Results Details for U.S. Appl. No. 15/548,577 and Search Result 20190107_145544_us-15-548-577-32.rai. Search run on Jan. 7, 2019. retrieved Jan. 8, 2019 at http://score.uspto.gov/ScoreAccessWeb/getItem.htm?AppId=15548577&seqId=09323b678 . . . 4 pages.
Score Search Results Details for U.S. Appl. No. 15/548,577 and Search Result 20190107_145544_us-15-548-577-32.rapbm. Search run on Jan. 7, 2019. retrieved Jan. 8, 2019 at http://score.uspto.gov/ScoreAccessWeb/getItem.htm?AppId=15548577&seqId=09323b678 . . . 6 pages.
Score Search Results Details for U.S. Appl. No. 15/548,577 and Search Result 20190107_145544_us-15-548-577-33.rai. Search run on Jan. 7, 2019. retrieved Jan. 8, 2019 at http://score.uspto.gov/ScoreAccessWeb/getItem.htm?AppId=15548577&seqId=09323b678 . . . 4 pages.
Score Search Results Details for U.S. Appl. No. 15/548,577 and Search Result 20190107_145544_us-15-548-577-33.rapbm. Search run on Jan. 7, 2019. retrieved Jan. 8, 2019 at http://score.uspto.gov/ScoreAccessWeb/getItem.htm?AppId=15548577&seqId=09323b678 . . . 12 pages.
EP22180254.9 Extended European Search Report dated Jan. 16, 2023.
U.S. Appl. No. 17/862,721 Office Action dated Jan. 5, 2023.

* cited by examiner

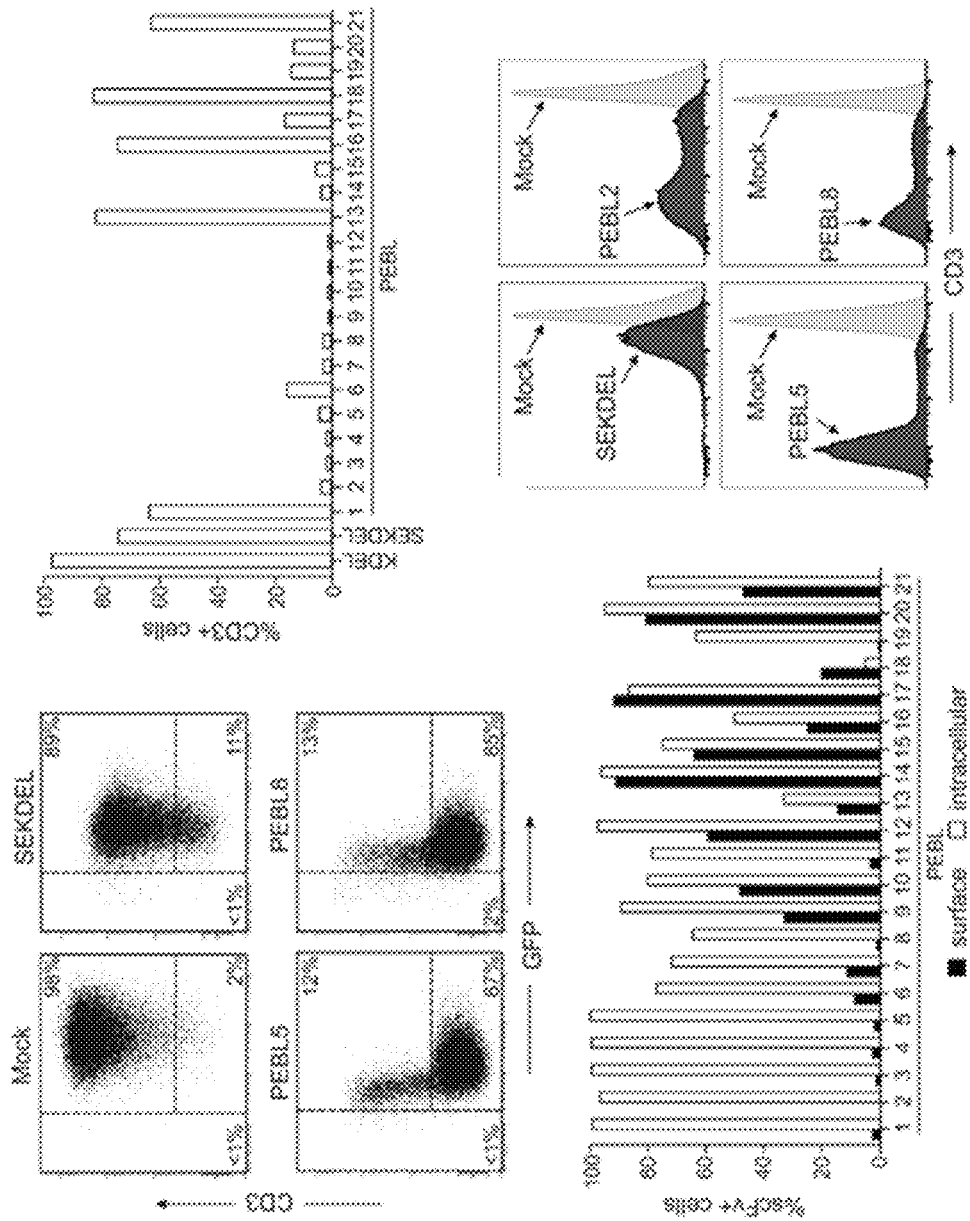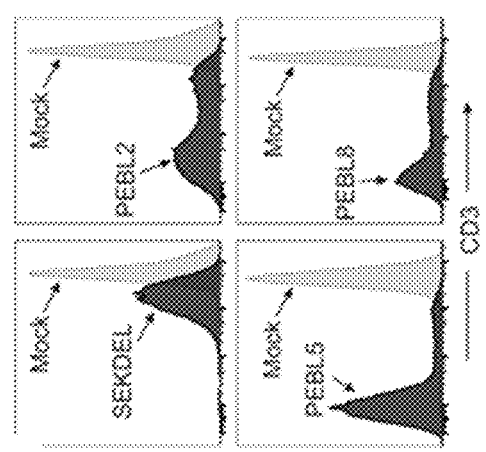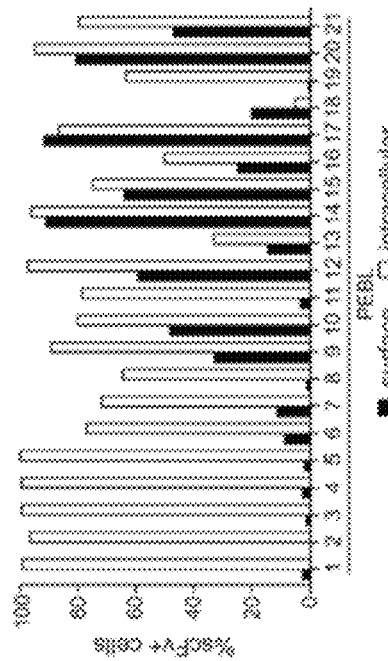

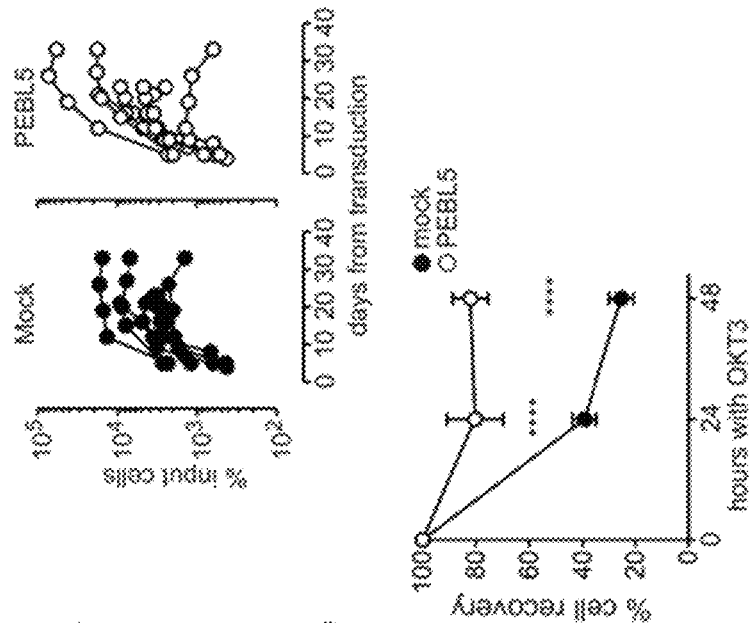
FIG. 3B
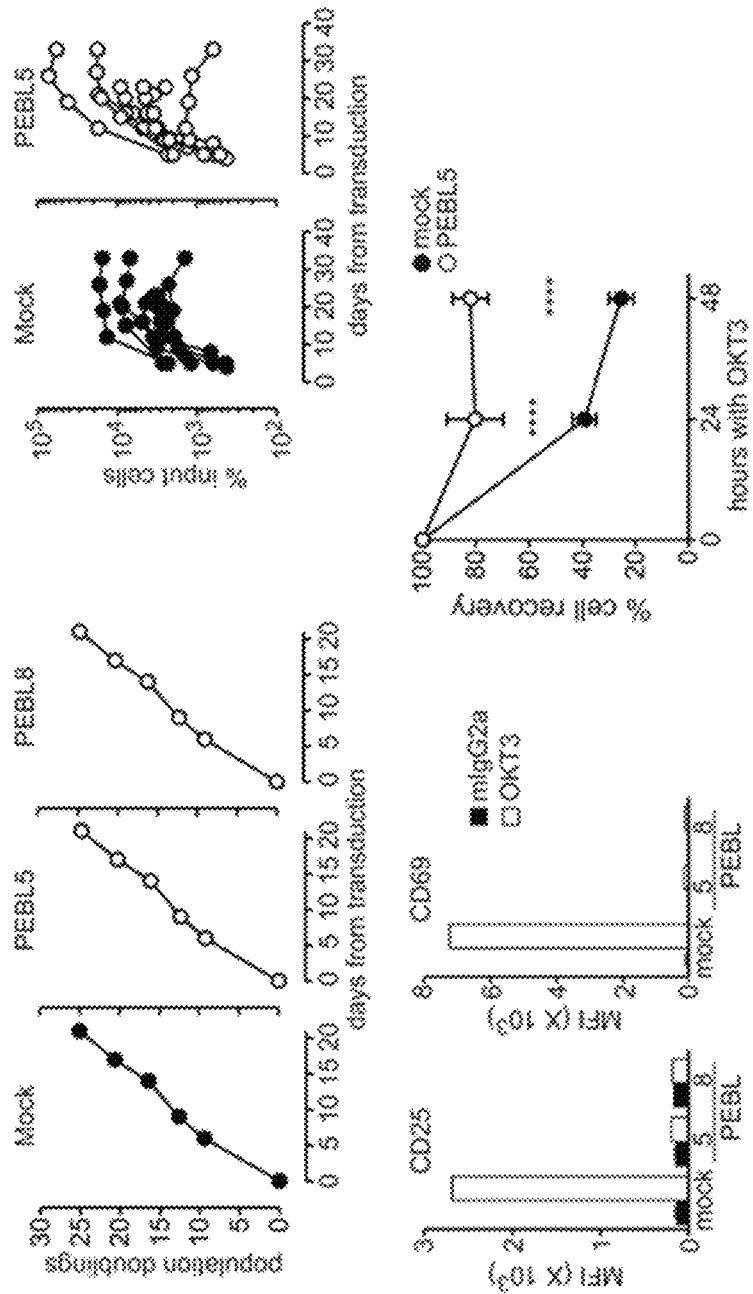
FIG. 3A
FIG. 3C
FIG. 3D

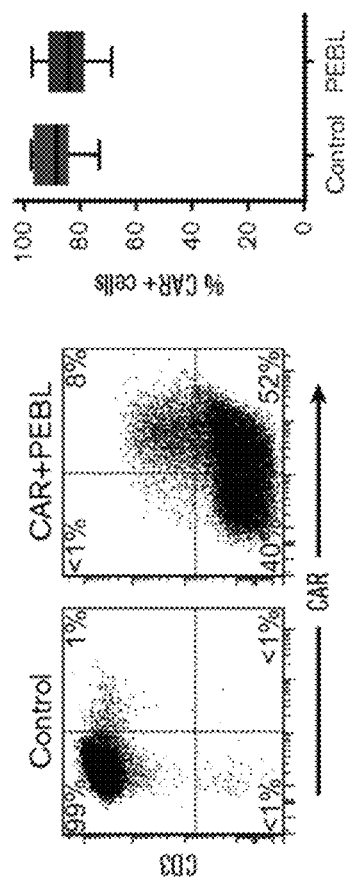
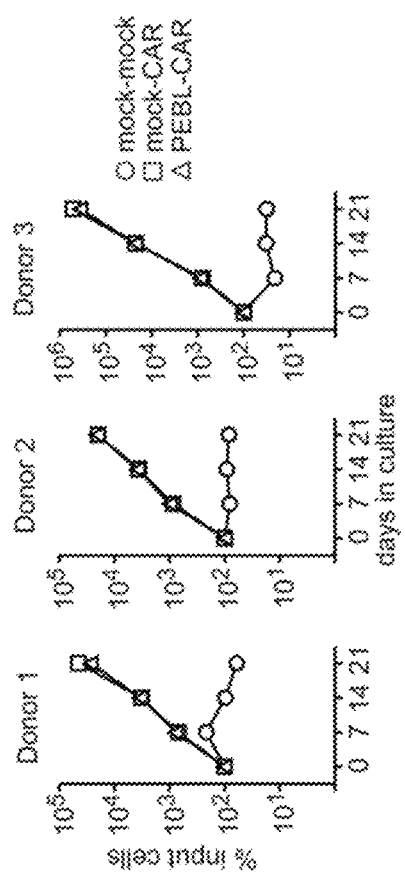
FIG. 4A
FIG. 4B
FIG. 4C
FIG. 4D

FIG. 8A

| PEBL | Amino acid Sequence | SEQ ID NO: |
|---|---|---|
| 1 | AEKDEL | 11 |
| 2 | EQKLISEEDLKDEL | 12 |
| 3 | GGGGSGGGGSKDEL | 13 |
| 4 | GGGGSGGGGSGGGGSGGGGSKDEL | 14 |
| 5 | GGGGSGGGGSGGGGSGGGGSAEKDEL | 15 |
| 6 | CD8α* plus KYKSRRSFIEEKKMP | 16 |
| 7 | CD8α* plus LKYKSRRSFIEEKKMP | 17 |
| 8 | CD8α* plus LYKYKSRRSFIEEKKMP | 18 |
| 9 | CD8α* plus LYCKYKSRRSFIEEKKMP | 19 |
| 10 | CD8α* plus LYCNKYKSRRSFIEEKKMP | 20 |
| 11 | CD8α* plus LYKYKSRRSFIDEKKMP | 21 |
| 12 | CD8α* plus  LYCNKYKSRRSFIDEKKMP | 22 |
| 13 | CD8α* plus LYEQKLISEEDLKYKSRRSFIEEKKMP | 23 |
| 14 | CD8α* plus LYCYPYDVPDYAKYKSRRSFIEEKKMP | 24 |
| 15 | CD8α* plus LYKKLETFKKTN | 25 |
| 16 | CD8α* plus LYEQKLISEEDLKKLETFKKTN | 26 |
| 17 | CD8α* plus LYYQRL | 27 |
| 18 | CD8α* plus LYEQKLISEEDLYQRL | 28 |
| 19 | CD8α* plus LYKRKIIAFALEGKRSKVTRRPKASDYQRL | 29 |
| 20 | CD8α* plus LYRNIKCD | 30 |
| 21 | CD8α* plus LYEQKLISEEDLRNIKCD | 31 |
|  | CD8α* is CD8α TM domain (SEQ ID NO:7) |  |

FIG. 8B

| Marker | n | Mock (%) | PEBL (%) |
|---|---|---|---|
| CD4 | 5 | 33.0 ± 8.0 | 31.0 ± 11.1 |
| CD8 | 5 | 63.7 ± 8.0 | 65.7 ± 11.1 |
| CD2 | 3 | 100 ± 0 | 100 ± 0 |
| CD7 | 3 | 99.6 ± 0.2 | 99.6 ± 0.2 |
| CD25(IL2Rα) | 3 | 58.1 ± 24.7 | 60.9 ± 25.5 |
| CD62L | 3 | 78.5 ± 11.0 | 68.3 ± 17.5 |
| CD69 | 3 | 21.9 ± 5.4 | 25.2 ± 6.7 |
| 41BB (CD137) | 3 | 17.0 ± 13.0 | 3.7 ± 2.9 |
| TIM-3 (CD366) | 3 | 89.6 ± 0.4 | 88.3 ± 3.0 |
| PD-1 (CD279) | 3 | 25.5 ± 10.1 | 26.0 ± 8.0 |
| LAG3 (CD223) | 3 | 25.3 ± 8.6 | 21.5 ± 6.9 |

FIG. 8C

| Organ | No T cells | | | Control | | | anti-CD3 PBL | | |
|---|---|---|---|---|---|---|---|---|---|
| | Description | Fibrosis | Inflammation | Description | Fibrosis | Inflammation | Description | Fibrosis | Inflammation |
| Spleen | Minimal focal perivascular fibrosis | 1 | 0 | Severe multifocal perivascular fibrosis with mononuclear cell infiltrate; individual cell necrosis; decreased extramedullary hematopoietic cells | 4 | 4 | Moderate multifocal perivascular fibrosis with mononuclear cell infiltrate | 3 | 3 |
| Liver | | 0 | 0 | Moderate periportal mononuclear cell infiltrate; sinusoidal leukocytosis; mild multifocal extra-medullary hematopoiesis | 2 | 2 | Minimal periportal mononuclear cell infiltrate; sinusoidal leukocytosis; mild multifocal extra-medullary hematopoiesis | 1 | 1 |
| Lung | | 0 | 0 | Severe diffuse perivascular and interstitial mono- and poly-nuclear cell infiltrate, fibrosis and edema; severe diffuse alveolar histiocytosis | 4 | 4 | Mild diffuse perivascular and interstitial mono- and poly-nuclear cell infiltrate, fibrosis and edema; mild diffuse alveolar histiocytosis | 1 | 1 |
| Skin | | 0 | 0 | Minimal diffuse mononuclear and mast cell interstitial dermal infiltrate | 0 | 1 | | 0 | 0 |
| Small intestine | | 0 | 0 | Mild lamina propria lymphoplasmacytic infiltrate and fibrosis | 1 | 1 | | 0 | 0 |
| Bone marrow | | 0 | 0 | Severe fibrosis; mononuclear cell infiltrate; loss of hematopoietic cells | 3 | 2 | | 0 | 0 |

The severity of infiltrate with respect to fibrosis and inflammation is scored as follows: 0, no infiltration; 1, sporadic or <5% infiltration; 2, mild infiltration of 5%-25%; 3, moderate infiltration of 25%-50%; 4, severe infiltration of 60%.

SEQUENCE LISTING

```
<160> NUMBER OF SEQ ID NOS: 43

<210> SEQ ID NO 1
<211> LENGTH: 120
<212> TYPE: PRT
<213> ORGANISM: Artificial Sequence
<220> FEATURE:
<223> OTHER INFORMATION: synthetic polypeptide

<400> SEQUENCE: 1

Glu Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60
```

```
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala
        115                 120

<210> SEQ ID NO 2
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 2

Gln Ile Val Leu Thr Gln Ser Pro Ala Ile Met Ser Ala Ser Pro Gly
  1               5                  10                  15

Glu Lys Val Thr Met Thr Cys Ser Ala Ser Ser Ser Val Ser Tyr Met
                 20                  25                  30

Asn Trp Tyr Gln Gln Lys Ser Gly Thr Ser Pro Lys Arg Trp Ile Tyr
             35                  40                  45

Asp Thr Ser Lys Leu Ala Ser Gly Val Pro Ala His Phe Arg Gly Ser
 50                  55                  60

Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn Arg
            100                 105

<210> SEQ ID NO 3
<211> LENGTH: 360
<212> TYPE: DNA
<213> ORGANISM: Artificial Sequence
<220> FEATURE:
<223> OTHER INFORMATION: synthetic polynucleotide

<400> SEQUENCE: 3
gaggtccagc tgcagcagtc tggggctgaa ctggcaagac ctggggcctc agtgaagatg      60
tcctgcaagg cttctggcta cacctttact aggtacacga tgcactgggt aaaacagagg     120
cctggacagg gtctggaatg gattggatac attaatccta gccgtggtta ctactaattac    180 aatcagaagt tcaaggacaa ggccacattg actacagaca atcctccag cacagcctac      240 atgcaactga gcagcctgac atctgaggac tctgcagtct attactgtgc aagatattat     300
gatgatcatt actgccttga ctactggggc caaggcacca ctctcacagt ctcctcagcc     360

<210> SEQ ID NO 4
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 4
caaattgttc tcacccagtc tccagcaatc atgtctgcat ctccagggga gaaggtcacc      60
atgacctgca gtgccagctc aagtgtaagt tacatgaact ggtaccagca gaagtcaggc     120
```

```
acctccccca aaagatggat ttatgacaca tccaaactgg cttctggagt ccctgctcac    180
ttcaggggca gtgggtctgg gacctcttac tctctcacaa tcagcggcat ggaggctgaa    240
gatgctgcca cttattactg ccagcagtgg agtagtaacc cattcacgtt cggctcgggg    300
acaaagttgg aaataaaccg g                                              321
```

```
<210> SEQ ID NO 5
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 5

Met Ala Leu Pro Val Thr Ala Leu Leu Leu Pro Leu Ala Leu Leu
1               5                   10                  15

His Ala Ala Arg Pro
            20
```

```
<210> SEQ ID NO 6
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 6

Gly Gly Gly Gly Ser Gly Gly Gly Ser Gly Gly Gly Gly Ser Gly
1               5                   10                  15

Gly Gly Gly Ser
            20
```

```
<210> SEQ ID NO 7
<211> LENGTH: 69
<212> TYPE: PRT
<213> ORGANISM: Artificial Sequence
<220> FEATURE:
<223> OTHER INFORMATION: synthetic polypeptide

<400> SEQUENCE: 7

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Ile Thr Leu Tyr
65
```

```
<210> SEQ ID NO 8
<211> LENGTH: 63
<212> TYPE: DNA
<213> ORGANISM: Artificial Sequence
<220> FEATURE:
<223> OTHER INFORMATION: synthetic polynucleotide

<400> SEQUENCE: 8
atggccttac cagtgaccgc cttgctcctg ccgctggcct tgctgctcca cgccgccagg     60
ccg                                                                   63
```

<210> SEQ ID NO 9
<211> LENGTH: 60
<212> TYPE: DNA
<213> ORGANISM: Artificial Sequence
<220> FEATURE:
<223> OTHER INFORMATION: synthetic polynucleotide

<400> SEQUENCE: 9
ggtggtggtg gttctggtgg tggtggttct ggcggcggcg gctccggtgg tggtggatcc    60

<210> SEQ ID NO 10
<211> LENGTH: 210
<212> TYPE: DNA
<213> ORGANISM: Artificial Sequence
<220> FEATURE:
<223> OTHER INFORMATION: synthetic polynucleotide

<400> SEQUENCE: 10
aagcccacca cgacgccagc gccgcgacca ccaacaccgg cgcccaccat cgcgtcgcag    60
cccctgtccc tgcgcccaga ggcgtgccgg ccagcggcgg ggggcgcagt gcacacgagg   120
gggctggact cgcctgtga tatctacatc tgggcgccct tggccgggac ttgtgggtc    180 cttctcctgt cactggttat caccctttac                                    210

<210> SEQ ID NO 11
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 11

Ala Glu Lys Asp Glu Leu
1               5

<210> SEQ ID NO 12
<211> LENGTH: 14
<212> TYPE: PRT
<213> ORGANISM: Artificial Sequence
<220> FEATURE:
<223> OTHER INFORMATION: synthetic polypeptide

<400> SEQUENCE: 12

Glu Gln Lys Leu Ile Ser Glu Glu Asp Leu Lys Asp Glu Leu
1               5                   10

<210> SEQ ID NO 13
<211> LENGTH: 14
<212> TYPE: PRT
<213> ORGANISM: Artificial Sequence
<220> FEATURE:
<223> OTHER INFORMATION: synthetic polypeptide

<400> SEQUENCE: 13

Gly Gly Gly Gly Ser Gly Gly Gly Gly Ser Lys Asp Glu Leu
1               5                   10

<210> SEQ ID NO 14
<211> LENGTH: 24
<212> TYPE: PRT
<213> ORGANISM: Artificial Sequence
<220> FEATURE:
<223> OTHER INFORMATION: synthetic polypeptide

<400> SEQUENCE: 14

```
Gly Gly Gly Gly Ser Gly Gly Gly Ser Gly Gly Gly Ser Gly
1               5                   10                  15

Gly Gly Gly Ser Lys Asp Glu Leu
                20
```

<210> SEQ ID NO 15
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 15

```
Gly Gly Gly Gly Ser Gly Gly Gly Ser Gly Gly Gly Ser Gly
1               5                   10                  15

Gly Gly Gly Ser Ala Glu Lys Asp Glu Leu
                20                  25
```

<210> SEQ ID NO 16
<211> LENGTH: 84
<212> TYPE: PRT
<213> ORGANISM: Artificial Sequence
<220> FEATURE:
<223> OTHER INFORMATION: synthetic polypeptide

<400> SEQUENCE: 16

```
Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Leu Ser
        50                  55                  60

Leu Ile Thr Leu Tyr Lys Tyr Lys Ser Arg Arg Ser Phe Ile Glu Glu
65                  70                  75                  80

Lys Lys Met Pro
```

<210> SEQ ID NO 17
<211> LENGTH: 85
<212> TYPE: PRT
<213> ORGANISM: Artificial Sequence
<220> FEATURE:
<223> OTHER INFORMATION: synthetic polypeptide

<400> SEQUENCE: 17

```
Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Leu Ser
        50                  55                  60

Leu Ile Thr Leu Tyr Leu Lys Tyr Lys Ser Arg Arg Ser Phe Ile Glu
65                  70                  75                  80

Glu Lys Lys Met Pro
                85
```

```
<210> SEQ ID NO 18
<211> LENGTH: 86
<212> TYPE: PRT
<213> ORGANISM: Artificial Sequence
<220> FEATURE:
<223> OTHER INFORMATION: synthetic polypeptide

<400> SEQUENCE: 18

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Ile Thr Leu Tyr Leu Tyr Lys Tyr Lys Ser Arg Arg Ser Phe Ile
65                  70                  75                  80

Glu Glu Lys Lys Met Pro
                85

<210> SEQ ID NO 19
<211> LENGTH: 87
<212> TYPE: PRT
<213> ORGANISM: Artificial Sequence
<220> FEATURE:
<223> OTHER INFORMATION: synthetic polypeptide

<400> SEQUENCE: 19

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Ile Thr Leu Tyr Leu Tyr Cys Lys Tyr Lys Ser Arg Arg Ser Phe
65                  70                  75                  80

Ile Glu Glu Lys Lys Met Pro
                85

<210> SEQ ID NO 20
<211> LENGTH: 88
<212> TYPE: PRT
<213> ORGANISM: Artificial Sequence
<220> FEATURE:
<223> OTHER INFORMATION: synthetic polypeptide

<400> SEQUENCE: 20

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Ile Thr Leu Tyr Leu Tyr Cys Asn Lys Tyr Lys Ser Arg Arg Ser
65                  70                  75                  80
```

Phe Ile Glu Glu Lys Lys Met Pro
                85

<210> SEQ ID NO 21
<211> LENGTH: 86
<212> TYPE: PRT
<213> ORGANISM: Artificial Sequence
<220> FEATURE:
<223> OTHER INFORMATION: synthetic polypeptide

<400> SEQUENCE: 21

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Leu Ser
    50                  55                  60

Leu Ile Thr Leu Tyr Leu Tyr Lys Tyr Lys Ser Arg Arg Ser Phe Ile
65                  70                  75                  80

Asp Glu Lys Lys Met Pro
                85

<210> SEQ ID NO 22
<211> LENGTH: 88
<212> TYPE: PRT
<213> ORGANISM: Artificial Sequence
<220> FEATURE:
<223> OTHER INFORMATION: synthetic polypeptide

<400> SEQUENCE: 22

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Leu Ser
    50                  55                  60

Leu Ile Thr Leu Tyr Leu Tyr Cys Asn Lys Tyr Lys Ser Arg Arg Ser
65                  70                  75                  80

Phe Ile Asp Glu Lys Lys Met Pro
                85

<210> SEQ ID NO 23
<211> LENGTH: 96
<212> TYPE: PRT
<213> ORGANISM: Artificial Sequence
<220> FEATURE:
<223> OTHER INFORMATION: synthetic polypeptide

<400> SEQUENCE: 23

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Ser
            50                  55                  60

Leu Ile Thr Leu Tyr Leu Tyr Glu Gln Lys Leu Ile Ser Glu Glu Asp
 65                  70                  75                  80

Leu Lys Tyr Lys Ser Arg Arg Ser Phe Ile Glu Glu Lys Lys Met Pro
                85                  90                  95

<210> SEQ ID NO 24
<211> LENGTH: 96
<212> TYPE: PRT
<213> ORGANISM: Artificial Sequence
<220> FEATURE:
<223> OTHER INFORMATION: synthetic polypeptide

<400> SEQUENCE: 24

Lys Pro Thr Thr Thr Pro Ala Pro Arg Pro Pro Thr Pro Ala Pro Thr
  1               5                  10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Leu Ser
        50                  55                  60

Leu Ile Thr Leu Tyr Leu Tyr Cys Tyr Pro Tyr Asp Val Pro Asp Tyr
 65                  70                  75                  80

Ala Lys Tyr Lys Ser Arg Arg Ser Phe Ile Glu Glu Lys Lys Met Pro
                85                  90                  95

<210> SEQ ID NO 25
<211> LENGTH: 81
<212> TYPE: PRT
<213> ORGANISM: Artificial Sequence
<220> FEATURE:
<223> OTHER INFORMATION: synthetic polypeptide

<400> SEQUENCE: 25

Lys Pro Thr Thr Thr Pro Ala Pro Arg Pro Pro Thr Pro Ala Pro Thr
  1               5                  10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Leu Ser
        50                  55                  60

Leu Ile Thr Leu Tyr Leu Tyr Lys Lys Leu Glu Thr Phe Lys Lys Thr
 65                  70                  75                  80

Asn

<210> SEQ ID NO 26
<211> LENGTH: 91
<212> TYPE: PRT
<213> ORGANISM: Artificial Sequence
<220> FEATURE:
<223> OTHER INFORMATION: synthetic polypeptide

<400> SEQUENCE: 26

Lys Pro Thr Thr Thr Pro Ala Pro Arg Pro Pro Thr Pro Ala Pro Thr
  1               5                  10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Leu Ser
    50                  55                  60

Leu Ile Thr Leu Tyr Leu Tyr Glu Gln Lys Leu Ile Ser Glu Glu Asp
65                  70                  75                  80

Leu Lys Lys Leu Glu Thr Phe Lys Lys Thr Asn
                85                  90

<210> SEQ ID NO 27
<211> LENGTH: 75
<212> TYPE: PRT
<213> ORGANISM: Artificial Sequence
<220> FEATURE:
<223> OTHER INFORMATION: synthetic polypeptide

<400> SEQUENCE: 27

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Leu Ser
    50                  55                  60

Leu Ile Thr Leu Tyr Leu Tyr Tyr Gln Arg Leu
65                  70                  75

<210> SEQ ID NO 28
<211> LENGTH: 85
<212> TYPE: PRT
<213> ORGANISM: Artificial Sequence
<220> FEATURE:
<223> OTHER INFORMATION: synthetic polypeptide

<400> SEQUENCE: 28

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Leu Ser
    50                  55                  60

Leu Ile Thr Leu Tyr Leu Tyr Glu Gln Lys Leu Ile Ser Glu Glu Asp
65                  70                  75                  80

Leu Tyr Gln Arg Leu
                85

<210> SEQ ID NO 29
<211> LENGTH: 99
<212> TYPE: PRT
<213> ORGANISM: Artificial Sequence
<220> FEATURE:
<223> OTHER INFORMATION: synthetic polypeptide

<400> SEQUENCE: 29

Lys Pro Thr Thr Thr Pro Ala Pro Arg Pro Pro Thr Pro Ala Pro Thr
1               5                   10                  15

```
Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Ile Thr Leu Tyr Leu Tyr Lys Arg Lys Ile Ile Ala Phe Ala Leu
65                  70                  75                  80

Glu Gly Lys Arg Ser Lys Val Thr Arg Arg Pro Lys Ala Ser Asp Tyr
                85                  90                  95

Gln Arg Leu

<210> SEQ ID NO 30
<211> LENGTH: 77
<212> TYPE: PRT
<213> ORGANISM: Artificial Sequence
<220> FEATURE:
<223> OTHER INFORMATION: synthetic polypeptide

<400> SEQUENCE: 30

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Ile Thr Leu Tyr Leu Tyr Arg Asn Ile Lys Cys Asp
65                  70                  75

<210> SEQ ID NO 31
<211> LENGTH: 87
<212> TYPE: PRT
<213> ORGANISM: Artificial Sequence
<220> FEATURE:
<223> OTHER INFORMATION: synthetic polypeptide

<400> SEQUENCE: 31

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Ile Thr Leu Tyr Leu Tyr Glu Gln Lys Leu Ile Ser Glu Glu Asp
65                  70                  75                  80

Leu Arg Asn Ile Lys Cys Asp
                85

<210> SEQ ID NO 32
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 32
```

Lys Asp Glu Leu
1

<210> SEQ ID NO 33
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 33

Lys Lys Met Pro
1

<210> SEQ ID NO 34
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 34

Tyr Gln Arg Leu
1

<210> SEQ ID NO 35
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (3)..(4)
<223> OTHER INFORMATION: wherein Xaa is any amino acid

<400> SEQUENCE: 35

Lys Lys Xaa Xaa
1

<210> SEQ ID NO 36
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 36

Gly Gly Gly Gly Ser
1               5

<210> SEQ ID NO 37
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 37

Gly Gly Gly Gly Ser Gly Gly Gly Gly Ser Gly Gly Gly Gly Ser Gly
1               5                   10                  15

Gly Gly Gly Ser
            20

<210> SEQ ID NO 38
<211> LENGTH: 15

```
<212> TYPE: PRT
<213> ORGANISM: Artificial Sequence
<220> FEATURE:
<223> OTHER INFORMATION: synthetic polypeptide

<400> SEQUENCE: 38

Gly Gly Gly Gly Ser Gly Gly Gly Gly Ser Gly Gly Gly Gly Ser
1               5                   10                  15

<210> SEQ ID NO 39
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 39

Gly Gly Gly Gly Ser Gly Gly Gly Gly Ser
1               5                   10

<210> SEQ ID NO 40
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<223> OTHER INFORMATION: wherein n is 2-12

<400> SEQUENCE: 40

Gly Gly Gly Gly Ser
1               5

<210> SEQ ID NO 41
<211> LENGTH: 40
<212> TYPE: PRT
<213> ORGANISM: Artificial Sequence
<220> FEATURE:
<223> OTHER INFORMATION: synthetic polypeptide

<400> SEQUENCE: 41

Ser His Gly Phe Pro Pro Glu Val Glu Glu Gln Asp Asp Gly Thr Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
        35                  40

<210> SEQ ID NO 42
<211> LENGTH: 19
<212> TYPE: PRT
<213> ORGANISM: Artificial Sequence
<220> FEATURE:
<223> OTHER INFORMATION: synthetic polypeptide

<400> SEQUENCE: 42

Ala Thr Asn Phe Ser Leu Leu Lys Gln Ala Gly Asp Val Glu Glu Asn
1               5                   10                  15

Pro Gly Pro

<210> SEQ ID NO 43
<211> LENGTH: 4
<212> TYPE: PRT
<213> ORGANISM: Artificial Sequence
<220> FEATURE:
```

```
<223> OTHER INFORMATION: synthetic polypeptide

<400> SEQUENCE: 43

Lys Lys Thr Asn
1
```

T CELL RECEPTOR-DEFICIENT CHIMERIC ANTIGEN RECEPTOR T-CELLS AND METHODS OF USE THEREOF

CROSS-REFERENCE TO RELATED APPLICATIONS

This application claims benefit to U.S. Provisional Application No. 62/543,735 filed Aug. 10, 2017, the disclosure in its entirety is herein incorporated by reference.

REFERENCE TO A SEQUENCE LISTING

The instant application contains a Sequence Listing which has been submitted electronically in ASCII format and is hereby incorporated by reference in its entirety. Said ASCII copy, created on Aug. 9, 2018, is named "119419-5003-US-SequenceListing_ST25.txt" and is 24.0 kilobytes in size.

BACKGROUND OF THE INVENTION

Genetically-engineered immune cells are a powerful new treatment for cancer. Results of recent clinical trials with T lymphocytes expressing chimeric antigen receptors (CARs) have provided compelling demonstration of the power of this approach. Chimeric antigen receptors (CARs) can redirect immune cells to specifically recognize and kill tumor cells. CARs are artificial multi-molecular proteins constituted by a single-chain variable region (scFv) of an antibody linked to a signaling molecule via a transmembrane domain. When the scFv ligates its cognate antigen, signal transduction is triggered, resulting in tumor cell killing by CAR-expressing cytotoxic T lymphocytes (Eshhar Z, Waks T, et al. PNAS USA. 90(2):720-724, 1993; Geiger T L, et al. J Immunol. 162(10):5931-5939, 1999; Brentjens R J, et al. Nat Med. 9(3):279-286, 2003; Cooper L J, et al. Blood 101(4):1637-1644, 2003; Imai C, et al. Leukemia. 18:676-684, 2004). Clinical trials with CAR-expressing autologous T lymphocytes have shown positive responses in patients with B-cell refractory leukemia and lymphoma (see, e.g., Till B G, et al. Blood 119(17):3940-3950, 2012; Maude S L, et al. N Engl J Med. 371(16):1507-1517, 2014).

It has been shown that CAR-T cells specific for the surface molecule CD19 induced morphologic and molecular remissions in patients with treatment-refractory CD19-positive malignancies, such as acute lymphoblastic leukemia (ALL), chronic lymphocytic leukemia, and non-Hodgkin lymphoma. Other malignancies can be attacked by T cells redirected against different antigens. Hence, the possible applications for genetically-engineered cellular therapy in oncology are wide-ranging.

The initial clinical experience with CAR-T cell infusions has also identified potential limitations, which could seriously diminish therapeutic effect and hamper development. A major issue is the variable fitness of immune cells collected from patients with cancer, resulting in an unpredictable capacity to expand in vivo, and exert anti-tumor effects. This variability complicates the identification of the most effective cell dosages, might lead to the infusion of short-lived and ineffective cell products, and could ultimately prevent the development of a consistent "living drug". The use of T lymphocytes from healthy donors should improve effectiveness and consistency, but carries the risk of graft-versus-host disease (GvHD), a serious, and potentially fatal, consequence of donor lymphocyte infusion. In such allogeneic setting, additional modifications to the infused T cells are required to suppress their capacity to recognize tissue antigens expressed by indispensable cells.[13]

The advent of practical methodologies for gene editing has opened new opportunities for therapeutic cell engineering which are applicable to cell therapy of cancer. Zinc finger meganucleases, TALEN, and CRISPR-Cas9 can be used to delete the genes encoding TCRαβ chains leading to T cells that lack alloreactivity, while other genes can be targeted to delay rejection. A report using TALEN deletion of the TCRα and CD52 loci together with anti-CD19 CAR expression indicates that combining CAR-expression with gene editing is feasible in a clinical setting, although technically challenging.

In sum, there is a significant unmet need for new therapeutic options for patients with B-cell malignancies.

SUMMARY OF THE INVENTION

Provided herein is a simple and effective method for the blockade of surface receptor expression in immune cells. Specific constructs, named Protein Expression Blockers (PEBLs), prevent transport of targeted proteins to the cell membrane. PEBL constructs can be readily combined with other gene modifications and be incorporated into existing large-scale cGMP-grade protocols for ex vivo cell processing to optimize the function of immune cells.

In one aspect, the present invention provides a method that allows rapid and efficient downregulation of surface molecules in T cells, including CAR-T cells. In one embodiment of the present invention, provided is an anti-CD3ε PEBL wherein transduction of the anti-CD3ε PEBL caused intracellular retention of CD3 which, in turn, prevented expression of TCRαβ on the surface of T lymphocytes. PEBL constructs outlined herein may have minimal or no extracellular leakage and are highly effective at blocking CD3/TCRαβ expression and signaling. Such PEBL constructs can render T cells transduced with anti-viral TCRs unable to respond to a cognate viral peptide, and can markedly reduce the capacity of human T cells to cause graft-versus-host disease (GvHD). PEBL expression and CD3/TCRαβ blockage are durable and do not affect expression of other surface molecules. PEBL-expressing T cells can survive and proliferate as well as comparable T cells. Importantly, PEBL-expressing T cells respond normally to CAR signaling and can effectively kill CAR-targeted leukemic cells in vitro. PEBL blockade of CD3/TCRαβ expression and signaling is a simple and effective tool to support infusion of allogeneic T cells, such as CAR-T cells.

In one aspect, the invention provides an engineered CD3/TCRαβ-deficient T cell comprising a polypeptide comprising a target-binding molecule linked to a localizing domain, wherein the target-binding molecule comprises an antibody that binds a CD3/TCRαβ complex protein, the localizing domain comprises a retention signaling domain comprising an amino acid sequence selected from the group consisting of an endoplasmic reticulum (ER) retention sequence, a Golgi retention sequence, and a proteosome localizing sequence, and the target-binding molecule linked to the localizing domain is not secreted by the engineered CD3/TCRαβ-deficient T cell.

In some embodiments, the antibody is a single chain variable fragment (scFv) that binds the CD3/TCRαβ complex protein selected from the group consisting of TCRα, TCRβ, CD3ε, CD3δ, CD3γ, and CD3ζ. In certain embodiments, the scFv comprises a variable heavy chain ($V_H$) sequence having at least 95% sequence identity to SEQ ID NO:1 and a variable light chain (V_L) sequence having at least 95% sequence identity to SEQ ID NO:2.

In some embodiments, the localizing domain further comprises a transmembrane domain selected from a transmembrane domain derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In some embodiments, the ER retention sequence comprises an amino acid sequence selected from KDEL (SEQ ID NO:32), KKMP (SEQ ID NO:33), KKTN (SEQ ID NO:43), or KKXX, wherein X is any amino acid (SEQ ID NO:35).

In other aspects, provided herein is pharmaceutical composition comprising any one of the engineered T cells described herein, and a pharmaceutically acceptable carrier. In some embodiments, also provided herein is method of reducing or eliminating the likelihood of graft-versus-host disease in a patient, comprising administering to the patient a therapeutically effective amount of such a pharmaceutical composition.

In some embodiments, the engineered T cell described herein further comprises a chimeric antigen receptor (CAR), such as, but not limited to a CAR that binds CD3 or CD19. Disclosed herein is a pharmaceutical composition comprising such an engineered T cell and and a pharmaceutically acceptable carrier. In some aspect, the invention is directed to a method of treating cancer in a patient in need thereof comprising administering a therapeutically effective amount of such a pharmaceutical composition. In some instances, the cancer is a hematopoietic cancer. In other instances, the cancer is a CD3 expressing cancer (e.g., cancer cells express CD3). In certain instances, the cancer is a CD19 expressing cancer (e.g., cancer cells express CD19).

In various aspects, the present invention provides an engineered CD3/TCRαβ-deficient chimeric antigen receptor T cell (CAR-T cell) comprising: (i) a polypeptide comprising a target-binding molecule linked to a localizing domain, wherein the target-binding molecule comprises an antibody that binds a CD3/TCRαβ complex protein, wherein the localizing domain comprises a retention signaling domain comprising an amino acid sequence selected from the group consisting of an endoplasmic reticulum (ER) retention sequence, a Golgi retention sequence, and a proteosome localizing sequence, and wherein the target-binding molecule linked to the localizing domain is not secreted by the engineered cell; and (ii) a chimeric antigen receptor (CAR).

In some embodiments, the antibody is a single chain variable fragment (scFv) that binds the CD3/TCRαβ complex protein selected from the group consisting of TCRα, TCRβ, CD3ε, CD3δ, CD3γ, and CD3ζ. In certain embodiments, the scFv comprises a variable heavy chain (V_H) sequence having at least 95% sequence identity to SEQ ID NO:1 and a variable light chain (V_L) sequence having at least 95% sequence identity to SEQ ID NO:2. The localizing domain can also include a transmembrane domain selected from a transmembrane domain derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In some embodiments, the ER retention sequence comprises an amino acid sequence selected from KDEL (SEQ ID NO:32), KKMP (SEQ ID NO:33), KKTN (SEQ ID NO:43), or KKXX, wherein X is any amino acid (SEQ ID NO:35).

In some embodiments, the CAR of the engineered CD3/TCRαβ-deficient CAR-T cell binds CD3 or CD19. In some instances, the CAR comprises an anti-CD19 scFv domain, a 4-1BB stimulatory signaling domain, and a CD3ζ signaling domain. In other instances, the CAR comprises an anti-CD3 scFv domain, a 4-1BB stimulatory signaling domain, and a CD3ζ signaling domain.

In certain aspects, provided herein is a method of treating cancer in a patient in need thereof comprising administering to the patient a therapeutically effective amount of a pharmaceutical composition comprising an engineered CD3/TCRαβ-deficient chimeric antigen receptor T cell (CAR-T cell) comprising (i) a polypeptide comprising a target-binding molecule linked to a localizing domain, wherein the target-binding molecule comprises an antibody that binds a CD3/TCRαβ complex protein, wherein the localizing domain comprises a retention signaling domain comprising an amino acid sequence selected from the group consisting of an endoplasmic reticulum (ER) retention sequence, a Golgi retention sequence, and a proteosome localizing sequence, and wherein the target-binding molecule linked to the localizing domain is not secreted by the engineered cell; and (ii) a chimeric antigen receptor (CAR). The antibody can be a single chain variable fragment (scFv) that binds to the CD3/TCRαβ complex protein selected from the group consisting of TCRα, TCRβ, CD3ε, CD3δ, CD3γ, and CD3. In some embodiments, the scFv that binds CD3ε comprises a variable heavy chain (V_H) sequence having at least 95% sequence identity to SEQ ID NO:1 and a variable light chain (V_L) sequence having at least 95% sequence identity to SEQ ID NO:2. In some embodiments, the localizing domain further comprises a transmembrane domain selected from a transmembrane domain derived from CD8α, CD8β, 4-1BB, CD28, CD34, CD4, FcεRIγ, CD16, OX40, CD3c CD3ε, CD3γ, CD3δ, TCRα, CD32, CD64, VEGFR2, FAS, or FGFR2B. In some embodiments, the ER retention sequence comprises an amino acid sequence selected from the group consisting of KDEL (SEQ ID NO:32), KKMP (SEQ ID NO:33), KKTN (SEQ ID NO:43), or KKXX, wherein X is any amino acid (SEQ ID NO:35). In other embodiments, the localizing domain comprises an amino acid sequence selected from any one of SEQ ID NOS:11-31. In some instances, the CAR of the engineered CAR-T cell binds to CD3. In other instances, the CAR of the engineered CAR-T cell binds to CD3. The CAR can include an anti-CD19 scFv domain, a 4-1BB stimulatory signaling domain, and a CD3ζ signaling domain. Or, the CAR can include an anti-CD3 scFv domain, a 4-1BB stimulatory signaling domain, and a CD3ζ signaling domain.

In some embodiments, the engineered CAR-T cell is an allogeneic T cell (e.g., allogeneic engineered CAR-T cell). In other embodiments, the engineered CAR-T cell is an autologous T cell (e.g., autologous engineered CAR-T cell). Such an engineered CAR-T cell may elicit a reduced graft-versus-host response in a patient upon administration of the cell.

In some embodiments, the patient has a cancer such as a CD3-positive cancer. In other embodiments, the patient has a cancer such as a CD19-positive cancer.

In other aspects, provided herein is a method of treating cancer in a patient in need thereof comprising administering to the patient a therapeutically effective amount of a pharmaceutical composition comprising an allogenic engineered CD3/TCRαβ-deficient chimeric antigen receptor T cell (CAR-T cell) comprising: i) a polypeptide comprising a target-binding molecule linked to a localizing domain, wherein the target-binding molecule comprises an antibody that binds CDε, wherein the localizing domain comprises a retention signaling domain comprising an amino acid sequence selected from the group consisting of an endoplasmic reticulum (ER) retention sequence, a Golgi retention sequence, and a proteosome localizing sequence, and wherein the target-binding molecule linked to the localizing domain is not secreted by the engineered cell; and (ii) a chimeric antigen receptor (CAR).

In some embodiments, the antibody is a single chain variable fragment (scFv) that binds CD3ε. The scFv that binds CD3ε comprises a variable heavy chain ($V_H$) sequence having at least 95% sequence identity to SEQ ID NO:1 and a variable light chain ($V_L$) sequence having at least 95% sequence identity to SEQ ID NO:2. In some embodiments, the localizing domain further comprises a transmembrane domain selected from a transmembrane domain derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In some embodiments, the ER retention sequence comprises an amino acid sequence selected from KDEL (SEQ ID NO:32), KKNIP (SEQ ID NO:33), KKTN (SEQ ID NO:43), or KKXX, wherein X is any amino acid (SEQ ID NO:35). In some embodiments, the localizing domain comprises an amino acid sequence selected from any one of SEQ ID NOS:11-31. In some instances, the CAR binds CD3 or CD19. The CAR can include an anti-CD3 scFv domain, a 4-1BB stimulatory signaling domain, and a CD3ζ signaling domain, or an anti-CD19 scFv domain, a 4-1BB stimulatory signaling domain, and a CD3ζ signaling domain.

Provided herein is an engineered CD3/TCRαβ-negative T cell comprising a polypeptide comprising a target-binding molecule linked to a localizing domain, wherein the target-binding molecule comprises an antibody that binds a CD3/TCRαβ complex protein, wherein the localizing domain comprises a retention signaling domain comprising an amino acid sequence selected from the group consisting of an endoplasmic reticulum (ER) retention sequence, a Golgi retention sequence, and a proteosome localizing sequence, and wherein the target-binding molecule linked to the localizing domain is not secreted by the engineered cell.

Also, provided herein is a polynucleotide encoding a target-binding molecule linked to a localizing domain, wherein the target-binding molecule comprises an antibody that binds a CD3/TCRαβ complex protein, and wherein the localizing domain comprises a retention signaling domain comprising an amino acid sequence selected from the group consisting of an endoplasmic reticulum (ER) retention sequence, a Golgi retention sequence, and a proteosome localizing sequence.

Provided herein is an engineered CD3/TCRαβ-negative chimeric antigen receptor T cell (CAR-T cell) comprising: (i) a chimeric antigen receptor (CAR), and (ii) a target-binding molecule linked to a localizing domain, wherein the target-binding molecule comprises an antibody that binds a CD3/TCRαβ complex protein, wherein the localizing domain comprises a retention signaling domain comprising an amino acid sequence selected from the group consisting of an endoplasmic reticulum (ER) retention sequence, a Golgi retention sequence, and a proteosome localizing sequence, and wherein the target-binding molecule linked to the localizing domain is not secreted by the engineered CAR-T cell.

Provided herein is a method of treating cancer in a patient in need thereof, comprising administering a therapeutically effective amount of a pharmaceutical composition comprising any one of the engineered immune cells described herein to the patient with cancer, thereby treating cancer in a subject in need thereof.

In other aspects, provided herein is a method of treating a pre-malignant condition or cancer expressing CD3 or CD19 in a patient, comprising administering a therapeutically effective amount of a pharmaceutical composition comprising any one of the engineered immune cells described herein to the patient with cancer, thereby treating cancer in a subject in need thereof.

In another aspect, provided herein is a method of impairing a hematological cancer expressing CD3 or CD19 comprising contacting a hematological cancer cell with any one of the engineered immune cells described herein.

In some embodiments, the invention relates to a method for stimulating a T-cell to a target cell population or tissue in a mammal, e.g., human patient comprising administering a therapeutically effective amount of a pharmaceutical composition comprising any one of the engineered immune cells described herein to a mammal.

BRIEF DESCRIPTION OF THE DRAWINGS

FIG. 1A-FIG. 1D. Anti-CD3ε PEBLs block surface CD3 expression. (FIG. 1A) Flow cytometric dot-plots illustrate surface CD3 downregulation in Jurkat by anti-CD3ε PEBLs compared with cells transduced with GFP alone ("Control") or SEKDEL (SEQ ID NO:50). (FIG. 1B) Surface CD3 expression in Jurkat transduced with the indicated constructs. Bars show a mean of 2 to 3 experiments for KEDL, SEKDEL, and PEBL 2,4,5,8,9,11, or individual results for the remainder. (FIG. 1C) Intracellular or surface expression of PEBL-derived anti-CD3ε scFv in Jurkat. Bars show a mean of 2 to 3 experiments for PEBL 2,4,8,9,11, or individual results for the remainder. (FIG. 1D) Flow cytometric histograms illustrate CD3 expression in peripheral blood T cells transduced with anti-CD3ε SEKDEL or PEBLs, relative to that of lymphocytes transduced with GFP alone, 8 to 13 days posttransduction.

(FIG. 2A) TCRαβ expression in GFP-positive T lymphocytes 5 to 9 days after PEBL transduction. Mean (±standard deviation [SD]) is shown for cells transduced with GFP only ("Control"; n=25), PEBL2 (n=4), and PEBL5 (n=18); other data represent results of 1 or mean of 2 experiments. (FIG. 2B) Flow cytometric dot-plots illustrate TCRαβ downregulation in T lymphocytes compared with cells transduced with GFP only. (FIG. 2C) CD3/TCRαβ expression in Jurkat cells transduced with PEBL after long-term culture; Control, cells transduced with GFP alone. (FIG. 2D) Collective results of CD3/TCRαβ expression in long-term cultures of T lymphocytes (with 200 IU/mL IL-2) or Jurkat cells. Symbols indicate persistence of more than 90% reduction of surface CD3/TCRαβ in GFP+ transduced cells.

FIG. 3A-FIG. 3F. CD3/TCRαβ downregulation by PEBL does not affect cell proliferation, but abrogates CD3/TCRαβ signaling. (FIG. 3A) Growth rate of Jurkat transduced with anti-CD3 PEBLs or GFP only ("Control"). Symbols indicate mean (±SD) of triplicate measurements. (FIG. 3B) Survival of PEBL-transduced or control T lymphocytes from 5 donors (7 experiments) cultured with IL-2 (200 IU/mL). Symbols indicate mean of triplicate measurements. (FIG. 3C) CD25 and CD69 mean fluorescence intensity (MFI) in Jurkat after 24 hours with OKT3 or nonreactive mouse IgG2a. Bars indicate mean (±SD) of triplicate measurements. (FIG. 3D) Viable PEBL or control T lymphocytes recovered from cultures with OKT3 compared with cultures without OKT3, all containing IL-2 (200 IU/mL). Symbols represent mean (±SD) of 9 measurements with cells from 3 donors. P values by Student t test are shown for significant differences (**** $P<0.0001$). (FIG. 3E) Jurkat cells transduced with either a TCR specific for HBV s183 or a vector containing neomycin-resistant gene only ("NeoR") were transduced with anti-CD3 PEBL or mCherry only ("Control") after neomycin selection. CD3, TCRαβ, and TCRVβ3 chain (part of the HBV s183 TCR) expression is shown; TCRVβ3 expression was tested on the cell surface, and intracellularly after cell permeabilization. (FIG. 3F) Transduced Jurkat cells shown in panel E were cocultured with T2 cells loaded with HBV s183 peptide for 24 hours. Shown are CD25 and CD69 MFI minus those measured after culture with T2 cells, but without peptide. Symbols represent mean of triplicate measurements.

FIG. 4A-FIG. 4D. CAR expression and signaling in T cells with CD3/TCRαβ expression blockade. (FIG. 4A) Flow cytometric dot-plots illustrate CD3 downregulation and anti-CD19-41BB-CD3ζ CAR expression. Cells were transduced with the CAR construct followed by anti-CD3ε PEBL, or with GFP only followed by mCherry only ("Control"). (FIG. 4B) Percentage of T lymphocytes transduced with PEBL or GFP alone ("Control") expressing anti-CD19-41BB-CD3ζ CAR 24 hours after CAR mRNA electroporation (n=5), or 5 to 6 days after CAR viral transduction (n=4); P=0.207. (FIG. 4C) IFNγ production by PEBL or control T cells electroporated with CAR mRNA or no mRNA and cultured with CD19+ RS4; 11 for 8 hours at E:T 1:2. Bars represent mean (±SD) of 9 measurements with cells from 3 donors; ****P<0.0001. (FIG. 4D) T lymphocytes were first transduced with CAR and then transduced with either mCherry alone or anti-CD3 PEBL. Cells were then cultured with irradiated CD19+ OP-1 for 3 weeks. Results were compared with cells transduced with GFP only and then with mCherry only ("Control"). Symbols indicate mean (±SD) percentage cell recovery relative to number of input cells in triplicate cultures.

(FIG. 5A) Four-hour cytotoxicity assays of PEBL or control (mCherry-transduced) T cells from 3 donors electroporated either with anti-CD19-41BB-CD3ζ CAR mRNA or no mRNA against CD19+ ALL cell lines at 2:1 E:T (see also supplemental FIG. 4). Symbols indicate mean of 3 measurements for each donor. (FIG. 5B) Cytotoxicity of CAR-transduced T lymphocytes from 2 donors, sequentially transduced with a retroviral vector containing either mCherry alone or anti-CD3 PEBL was tested against CD19+ cell lines. Control, cells transduced with GFP only followed by mCherry only. Shown are data for 4-hour assays against CD19+ ALL cell lines at 1:1 E:T (full set of data in FIG. 12A and FIG. 12B). Each symbol indicates mean of triplicate experiments for each donor. (FIG. 5C-FIG. 5D) T lymphocytes transduced as in panel B were tested for long-term cytotoxicity against Nalm6 transduced with mCherry. Leukemia cell growth was measured with IncuCyte Zoom System (Essen BioScience). Whole-well imaging of triplicate cultures at 80 hours; E:T 1:8, is shown in FIG. 5C; leukemia cell growth measurements at the indicated E:T ratios in FIG. 5D. *P<0.001; **P<0.0001.

(FIG. 6A) NSG mice were irradiated with 2.5 Gy and IV injected 1 day later with 1×10$^7$ T lymphocytes transduced with either anti-CD3 PEBL or GFP only ("Control"; n=8 per group). Body weight is expressed as change relative to weight on day 3 after irradiation. (FIG. 6B) Hemoglobin levels and (C) platelet counts in peripheral blood. (FIG. 6D) Kaplan-Meier overall survival curves and log-rank test. Mice were euthanized when weight reduction exceeded 20% in 2 consecutive measurements (additional data in FIG. 14). (FIG. 6E) Human CD45+ cell counts in blood 18 days after T-cell injection. *P=0.0148; ***P<0.001.

(FIG. 7A) NSG mice were IV injected with 5×10$^5$ Nalm6-luciferase cells. Three days later, mice received 2×10$^7$ T-lymphocytes transduced with anti-CD19-41BB-CD3ζ CAR plus either PEBL or mCherry alone; other mice received tissue culture medium instead ("no T cells"). Bioluminescence images on day 3 are shown with enhanced sensitivity to illustrate Nalm6 engraftment. (FIG. 7B) Symbols correspond to the average bioluminescence signal in ventral and dorsal imaging. (FIG. 7C) Kaplan-Meier curves and log-rank test for overall survival. Mice were euthanized when the ventral and dorsal bioluminescence average signal reached 1×10$^{10}$ photons per second. **P<0.0001. (FIG. 7D) NSG mice were IV injected with 5×0$^5$ Nalm6-luciferase cells and with 2×10$^7$ T lymphocytes on day 3 as described in panel A. Before T lymphocytes injection, mice received 2.5 Gy total body irradiation. Bioluminescence images on day 3 are shown with enhanced sensitivity to illustrate Nalm6 engraftment. (FIG. 7E) Symbols correspond to bioluminescence average by ventral and dorsal imaging. (FIG. 7F) Kaplan-Meier curves and log-rank test for overall survival. Mice were euthanized when the ventral and dorsal bioluminescence average signal reached 1×10$^{10}$ photons per second, or when signs of GVHD (>20% weight reduction exceeded in 2 consecutive measurements, with reduced mobility and/or fur loss) were evident. GVHD occurred in 3 of the 5 CAR+mCherry mice and 0 of the 6 CAR+PEBL mice; relapse ("Rel.") rates were 0 of 5 vs 2 of 6, respectively. P=0.0014; ***P=0.0006.

FIG. 8A. Protein expression blocker (PEBL) constructs described herein.

FIG. 8B. Immunophenotype of T lymphocytes transduced with PEBL or GFP only ("Control"). Shown are the mean (±SD) of 3-5 measurements in transduced lymphocytes from 4 donors. Cell markers were analyzed 6-8 days after transduction. Percentages were calculated after gating on GFP+ cells for mock and CD3-negative cells for PEBL. P>0.05 for all comparisons. Antibodies were from BD Biosciences (CD4 PE-Cy7, CD8 PE, CD7 PE, CD25 PE-Cy7, CD62L APC, CD69 PE, Biolegend (CD2 APC, CD137 APC, CD279 PE, CD366 PE), and ThermoFisher Scientific (CD223 APC).

FIG. 8C. Pathological features of immunodeficient mice injected with T cells transduced with anti-CD3 PEBL or GFP alon ("Control").

(FIG. 10A) Flow cytometry histograms illustrate surface and intracellular expression of CD3 in Jurkat cells transduced with anti-CD3 PEBL5 or GFP alone ("Mock"). (FIG. 10B) Confocal microscopy imaging of anti-CD3 PEBL5 transduced Jurkat cells. After cell permeabilization, the PEBL scFv was detected with biotin conjugated goat anti-mouse F(ab')2 antibody followed by streptavidin PE, and CD3 was detected with anti-CD3 APC. (FIG. 10C) PEBLs are not secreted by transduced cells. PEBLs can be localized in a subcellular compartment within a cell. For instance, PEBLs can be retained in the ER or the Golgi. Supernatant of Jurkat cells transduced with anti-CD3 PEBLs, anti-CD3 scFv alone, or GFP only ("Mock") over 48 hours was incubated with CD3+ Loucy cells in 4° C. for 45 minutes. Secreted scFv bound to the surface of Loucy was visualized with biotin-conjugated goat anti-mouse F(ab')2 antibody followed by streptavidin APC.

FIG. 11A: Cytotoxicity of PEBL- or mock-transduced T cells electroporated either with anti-CD19-41BB-CD3ζ CAR mRNA or no mRNA. Shown are data for 4-hour assays against CD19+ ALL cell lines. Each symbols indicates the mean (±SD) of triplicate experiments at the indicated E:T ratios. FIG. 11B: The cytotoxicity of CAR- or GFP only-transduced T lymphocytes, sequentially transduced with either mCherry alone or anti-CD3 PEBL was tested against CD19+ cell lines. Shown are data for 4-hour assays against CD19+ ALL cell lines. Each symbols indicates the mean (±SD) of triplicate experiments at the indicated E:T ratios; each panel corresponds to experiments with cells from one donor.

(FIG. 13A) Schematic representation of the bicistronic construct. An illustrative 2A sequence of ATNFSLLKQAGDVEENPGP (SEQ ID NO:42) is provided in FIG. 13A. (FIG. 13B) Flow cytometric dot-plots illustrate CD3 downregulation and anti-CD19-41BB-CD3ζ CAR expression in peripheral blood T lymphocytes. Cells were transduced with GFP only ("Control") or the bicistronic construct (CAR-2A-PEBL). For the latter, shown are results before and after depletion of residual CD3+ cells. (FIG. 13C) Cytotoxicity of T lymphocytes transduced with either CAR or CAR-2A-PEBL, compared to that of control T lymphocytes. Shown are data for 4-hour assays against the CD19+ ALL cell lines OP-1, Nalm6 and RS4; 11. Each symbol indicates the mean (±SD) of triplicate experiments at the E:T ratios shown.

(FIG. 14A) Hemoglobin levels and (FIG. 14B) platelets counts in blood collected via cheek prick. (FIG. 14C) Hematoxylin-eosin staining, and immunohistochemistry with anti-human CD4 and CD8 antibodies of tissues from one of the mice in the Mock group. Infiltration of CD4+ or CD8+ lymphocytes as well as fibrosis was seen in all tissues, with reduction of hematopoietic cells in spleen and bone marrow.

DETAILED DESCRIPTION OF THE INVENTION

Figure 2A:
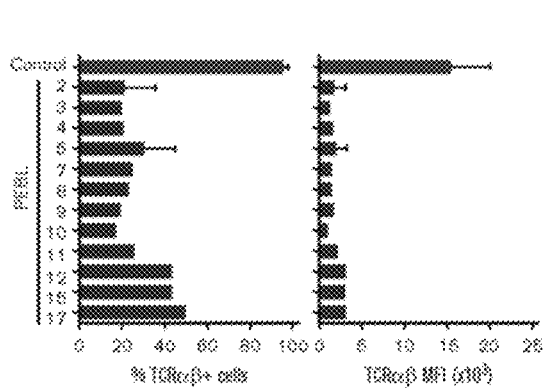
FIG. 2A-FIG. 2D. Anti-CD3ε PEBLs downregulate TCRαβ.
Figure 2B:
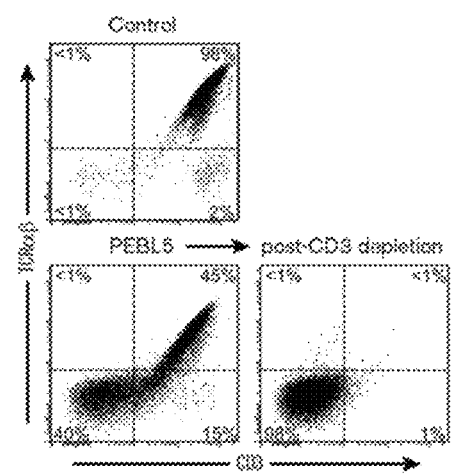

A description of example embodiments of the invention follows.

1. ENGINEERED CELLS EXPRESSING PROTEIN EXPRESSION BLOCKERS (PEBLs)

The methods described herein enable rapid removal or inactivation of specific target TCR complex proteins such as TCRα, TCRβ, CD3 (e.g., CD3δ, CD3ε, CD3γ, and CD3ζ) in immune cells. The method relies, in part, on a polypeptide construct containing a target-binding molecule that binds a target (e.g., protein) to be removed or neutralized. The target-binding molecule is linked to a domain (e.g., localizing domain) that directs the polypeptide to specific cellular compartments, such as the Golgi, endoplasmic reticulum (ER), proteasome, or cellular membrane, depending on the application. For simplicity, a target-binding molecule linked to a localizing domain can be referred to herein as a "Protein Expression Blocker" or "PEBL".

It has been shown that secretion of cytokines by activated immune cells triggers cytokine release syndrome and macrophage activation syndrome, presenting serious adverse effects of immune cell therapy (Lee D W, et al, Blood. 2014; 124(2): 188-195). Thus, PEBLs outlined herein can be used to block cytokines such as IL-6, IL-2, IL-4, IL-7, IL-10, IL-12, IL-15, IL-18, IL-21, IL-27, IL-35, interferon (IFN)-γ, IFN-β, IFN-α, tumor necrosis factor (TNF)-α, and transforming growth factor (TGF)-β, which may contribute to such inflammatory cascade. As such, the target-binding molecule can be a molecule that specifically binds to IL-6, IL-2, IL-4, IL-7, IL-10, IL-12, IL-15, IL-18, IL-21, IL-27, IL-35, IFN-γ, IFN-β, IFN-α, TNF-α, or TGF-β. In some embodiments, the target-binding molecule is a molecule that specifically binds to a TCR complex protein such as TCRα, TCRβ, CD3δ, CD3ε, CD3γ, and CD3ζ.

All such suitable binding molecules capable of activating or inactivating an immune response upon binding to a ligand (e.g., peptide or antigen) expressed on a T cell are collectively referred to as a "target-binding molecule." As would be appreciated by those of skill in the art, a target-binding molecule need not exclusively contain an antibody or antigen-binding fragment (e.g., scFv); rather the portion of the target-binding molecule that binds to a target molecule can be derived from, e.g., a receptor in a receptor-ligand pair, or a ligand in a receptor-ligand pair.

In some embodiments, the localizing domain comprises a retention signaling domain. In certain embodiments, the localizing domain comprises a retention signaling domain and a transmembrane domain. In some instances, the retention signaling domain comprises an endoplasmic reticulum (ER) retention sequence, a Golgi retention sequence, or a proteasome localizing sequence. The retention signaling domain can include an amino acid sequence that prevents or hinders a protein from being secreted by a cell. The retention signaling domain can include an amino acid sequence that retains a protein in an intracellular compartment. In some cases, the retention signaling domain can include an amino acid sequence that retains an anchor a protein in a cellular membrane such as a membrane of the ER or Golgi. For instance, the retention signaling domain can contain a KDEL sequence (SEQ ID NO:32), KKD or KKE sequence KKMP sequence (SEQ ID NO:33), YQRL sequence (SEQ ID NO:34), or KKXX sequence, wherein X is any amino acid sequence (SEQ ID NO:35).

In some embodiments, the protein expression blocking (PEBL) polypeptides are not secreted by a cell. In some embodiments, the PEBL polypeptides are not expressed on the cell surface of a cell. In some embodiments, the PEBL polypeptides do not function as a chimeric antigen receptor (CAR) that is expressed on the cell surface of a T cell.

The transmembrane domain can comprise a transmembrane domain derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In certain embodiments, the transmembrane domain of the localizing domain is derived from CD8α. The transmembrane domain can be linked to a retention signaling domain. In some embodiments, the transmembrane domain is linked to the retention signaling domain by way of a linker.

Non-limiting examples of a linker include $(GS)_n$, $(GGS)_n$, $(Gly_3Ser)_n$, $(Gly_2SerGly)_n$, $(Gly_2SerGly_2)_n$, or $(Gly_4Ser)_n$, wherein n is 1, 2, 3, 4, 5, 6, 7, 8, 9, or 10. In some embodiment, the linker is $(Gly_4Ser)_3$ or $(Gly_4Ser)_4$. Variation in the linker length may retain or enhance activity, giving rise to superior efficacy in activity studies.

In some embodiments, the localizing domain of the present invention comprises an amino acid sequence provided in Table 1 and FIG. 8A. In some instances, the localizing domain comprises the amino acid sequence of SEQ ID NO:11. In some instances, the localizing domain comprises the amino acid sequence of SEQ ID NO:12. In some instances, the localizing domain comprises the amino acid sequence of SEQ ID NO:13. In some instances, the localizing domain comprises the amino acid sequence of SEQ ID NO:14. In some instances, the localizing domain comprises the amino acid sequence of SEQ ID NO:15. In some instances, the localizing domain comprises the amino acid sequence of SEQ ID NO:16. In some instances, the localizing domain comprises the amino acid sequence of SEQ ID NO:17. In some instances, the localizing domain comprises the amino acid sequence of SEQ ID NO:18. In some instances, the localizing domain comprises the amino acid sequence of SEQ ID NO:19. In some instances, the localizing domain comprises the amino acid sequence of SEQ ID NO:20. In some instances, the localizing domain comprises the amino acid sequence of SEQ ID NO:21. In some instances, the localizing domain comprises the amino acid sequence of SEQ ID NO:22. In some instances, the localizing domain comprises the amino acid sequence of SEQ ID NO:23. In some instances, the localizing domain comprises the amino acid sequence of SEQ ID NO:24. In some instances, the localizing domain comprises the amino acid sequence of SEQ ID NO:25. In some instances, the localizing domain comprises the amino acid sequence of SEQ ID NO:26. In some instances, the localizing domain comprises the amino acid sequence of SEQ ID NO:27. In some instances, the localizing domain comprises the amino acid sequence of SEQ ID NO:28. In some instances, the localizing domain comprises the amino acid sequence of SEQ ID NO:29. In some instances, the localizing domain comprises the amino acid sequence of SEQ ID NO:30. In some instances, the localizing domain comprises the amino acid sequence of SEQ ID NO:31.

As such, the localizing domain located at the C-terminal region of the PEBL while the target-binding domain is at the N-terminal region. In some embodiments, the PEBL from N-terminus to C-terminus comprises a target-binding domain, a linker, and a localizing domain. In other embodiments, the PEBL from N-terminus to C-terminus comprises a signal peptide, a target-binding domain, a linker, and a localizing domain. In certain embodiments, the PEBL from N-terminus to C-terminus comprises a signal peptide, a target-binding domain, and a localizing domain. In other embodiments, the PEBL from N-terminus to C-terminus comprises a target-binding domain and a localizing domain.

The engineered cells of the invention do not produce functional T cell receptors. In some embodiments, one or more of the components or subunits of the CD3/TCRαβ complex are not expressed on the cell surface. In other words, such cells are CD3/TCRαβ-negative or CD3/TCRαβ-deficient.

2. ENGINEERED CELLS EXPRESSING PROTEIN EXPRESSION BLOCKERS (PEBLs) AND CHIMERIC ANTIGEN RECEPTORS (CARs)

Accordingly, in one embodiment, the present invention relates to an engineered immune cell (e.g., an engineered T cell) that comprises a nucleic acid comprising a nucleotide sequence encoding a chimeric antigen receptor (e.g., CAR), and a nucleic acid comprising a nucleotide sequence encoding a target-binding molecule linked to a localizing domain (e.g., PEBL).

As used herein, an "engineered" immune cell includes an immune cell that has been genetically modified as compared to a naturally-occurring immune cell. For example, an engineered T cell produced according to the present methods carries a nucleic acid comprising a nucleotide sequence that does not naturally occur in a T cell from which it was derived. In some embodiments, the engineered immune cell of the present invention includes a PEBL and a chimeric antigen receptor (CAR). Non-limiting examples of an illustrative CAR include a CAR that binds CD3, CD19, CD22, CD30, CD123, B cell maturation antigen (BCMA), GD2, mesothelin, EGVRvIII, HER2, c-Met, PD-L1, other tumor associated antigens.

Illustrative tumor associated antigens include, but are not limited to, mesothelin, EGFRvIII, TSHR, CD19, CD123, CD22, CD30, CD171, CS-1, CLL-1, CD33, GD2, GD3, BCMA, Tn Ag, prostate specific membrane antigen (PSMA), ROR1, FLT3, FAP, TAG72, CD38, CD44v6, CEA, EPCAM, B7H3, KIT, IL-13Ra2, interleukin-11 receptor a (IL-11Ra), PSCA, PRSS21, VEGFR2, LewisY, CD24, platelet-derived growth factor receptor-beta (PDGFR-beta), SSEA-4, CD20, Folate receptor alpha (FRa), ERBB2 (Her2/neu), MUC1, epidermal growth factor receptor (EGFR), NCAM, Prostase, PAP, ELF2M, Ephrin B2, IGF-I receptor, CAIX, LMP2, gp1OO, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD 179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B 1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1

In some embodiments, the engineered immune cell of the present invention includes an anti-CD3 scFv linked to a localizing domain and a CAR that binds CD19. In a particular embodiment, the engineered immune cell of the present invention includes an anti-CD3 scFv linked to a localizing domain and an anti-CD19-4-1BB-CD3ζ CAR.

In other embodiments, the engineered immune cell of the present invention includes an anti-CD3 scFv linked to a localizing domain and a CAR that binds CD3. In a particular embodiment, the engineered immune cell of the present invention includes an anti-CD3 scFv linked to a localizing domain and an anti-CD3-4-1BB-CD3ζ CAR.

In certain embodiments, the engineered immune cell is an engineered T cell. In some instances, the T cell is a cytotoxic T cell, a helper T cell, a regulatory T cell, effector T cell, memory T cell, natural killer T cell, gamma delta T cell, and the like.

PEBLs outlined herein prevent transport of target proteins to a cellular membrane. For instance, PEBLs directed to a protein of the CD3/TCR complex described herein are retained in the ER. PEBLs directed to CD3ε can co-localize intracellularly with endogenous CD3. Thus, endogenous CD3 expression on the cell surface is suppressed. In some embodiments, such PEBLs abrogate CD3. In other embodiments, the PEBLs abrogate TCRαβ expression. PEBLs directed to CD3 can abrogate CD3/TCRαβ expression. In some instances, the PEBLs do not cause immunophenotypic changes in the engineered immune cell. Also, PEBLs do not affect proliferation of the engineered immune cell. In some embodiments, the PEBLs are co-expressed with a CAR, such as an anti-CD 19-4-1BB-CD3ζ CAR.

In certain aspects, the CAR binds to molecules expressed on the surface of tumor cells, including but not limited to, CD20, CD22, CD33, CD2, CD3, CD4, CD5, CD7, CD8, CD45, CD52, CD38, CS-1, TIM3, CD123, mesothelin, folate receptor, HER2-neu, epidermal-growth factor receptor, and epidermal growth factor receptor. In some embodiments, the immune activating receptor is a CAR (e.g., anti-CD19-4-1BB-CD3ζ CAR). In certain embodiments, the immune activating receptor comprises an antibody or antigen-binding fragment thereof (e.g., scFv) that binds to molecules expressed on the surface of tumor cells, including but not limited to, CD20, CD22, CD33, CD2, CD3, CD4, CD5, CD7, CD8, CD45, CD52, CD38, CS-1, TIM3, CD123, mesothelin, folate receptor, HER2-neu, epidermal-growth factor receptor, and epidermal growth factor receptor.

The transmembrane domain of a chimeric antigen receptor (e.g., CAR) according to the present invention can be derived from a single-pass membrane protein, including, but not limited to, CD8α, CD8β, 4-1BB, CD28, CD34, CD4, FcεRIγ, CD16 (e.g., CD16A or CD16B), OX40, CD3ζ, CD3δ, CD3γ, CD35, TCRα, CD32 (e.g., CD32A or CD32B), CD64 (e.g., CD64A, CD64B, or CD64C), VEGFR2, FAS, and FGFR2B. In some examples, the membrane protein is not CD8α. The transmembrane domain may also be a non-naturally occurring hydrophobic protein segment.

The hinge domain of the chimeric antigen receptor (e.g., CAR) can be derived from a protein such as CD8 α, or IgG. The hinge domain can be a fragment of the transmembrane or hinge domain of CD8 α, or a non-naturally occurring peptide, such as a polypeptide consisting of hydrophilic residues of varying length, or a (GGGGS)$_n$ (SEQ ID NO: 36) polypeptide, in which n is an integer of, e.g., 2-12, inclusive.

The signaling domain of the chimeric antigen receptor (e.g., CAR) can be derived from CD3ζ, FcεRIγ, DAP10, DAP12 or other molecules known to deliver activating signals in immune cells. At least one co-stimulatory signaling domain of the receptor can be a co-stimulatory molecule such as 4-1BB (also known as CD137), CD28 variant, OX40, ICOS, CD27, GITR, HVEM, TIM-1, TIM-3, LFA-1, or CD2. Such molecules are readily available and known in the art.

As would be appreciated by those of skill in the art, the components of an immune activating receptor can be engineered to comprise a number of functional combinations, as described herein, to produce a desired result. Using the particular anti-CD19-4-1BB-CD3ζ CAR as an example, the antibody (e.g., or antigen-binding fragment thereof such as an scFv) that binds a molecule can be substituted for an antibody that binds different molecule, as described herein (e.g., anti-CD20, anti-CD33, anti-CD123, etc., instead of anti-CD19). In other embodiments, the co-stimulatory molecule (4-1BB in this specific example) can also be varied with a different co-stimulatory molecule, e.g., CD28. In some embodiments, the stimulatory molecule (CD3, in this specific example), can be substituted with another known stimulatory molecule. In various embodiments, the transmembrane domain of the receptor can also be varied as desired. The design, production, and testing for functionality of such immune activating receptors can be readily determined by those of skill in the art. Similarly, the design, delivery into cells and expression of nucleic acids encoding such immune activating receptors are readily known and available in the art.

As used herein, the term "nucleic acid" refers to a polymer comprising multiple nucleotide monomers (e.g., ribonucleotide monomers or deoxyribonucleotide monomers). "Nucleic acid" includes, for example, genomic DNA, cDNA, RNA, and DNA-RNA hybrid molecules. Nucleic acid molecules can be naturally occurring, recombinant, or synthetic. In addition, nucleic acid molecules can be single-stranded, double-stranded or triple-stranded. In some embodiments, nucleic acid molecules can be modified. In the case of a double-stranded polymer, "nucleic acid" can refer to either or both strands of the molecule.

The term "nucleotide sequence," in reference to a nucleic acid, refers to a contiguous series of nucleotides that are joined by covalent linkages, such as phosphorus linkages (e.g., phosphodiester, alkyl and aryl-phosphonate, phosphorothioate, phosphotriester bonds), and/or non-phosphorus linkages (e.g., peptide and/or sulfamate bonds). In certain embodiments, the nucleotide sequence encoding, e.g., a target-binding molecule linked to a localizing domain is a heterologous sequence (e.g., a gene that is of a different species or cell type origin).

The terms "nucleotide" and "nucleotide monomer" refer to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., adenosine, thymidine, guanosine, cytidine, uridine, inosine, deoxyadenosine, deoxythymidine, deoxyguanosine, or deoxycytidine) and nucleotides comprising modified bases known in the art.

As will be appreciated by those of skill in the art, in some aspects, the nucleic acid further comprises a plasmid sequence. The plasmid sequence can include, for example, one or more sequences selected from the group consisting of a promoter sequence, a selection marker sequence, and a locus-targeting sequence.

As used herein, the gene encoding a target-binding molecule linked to a localizing domain is sometimes referred to as "gene encoding a PEBL."

In certain embodiments, the target-binding molecule is an antibody or antigen-binding fragment thereof. As used herein, "antibody" means an intact antibody or antigen-binding fragment of an antibody, including an intact antibody or antigen-binding fragment that has been modified or engineered, or that is a human antibody. Examples of antibodies that have been modified or engineered are chimeric antibodies, humanized antibodies, multiparatopic antibodies (e.g., biparatopic antibodies), and multispecific antibodies (e.g., bispecific antibodies). Examples of antigen-binding fragments include Fab, Fab', F(ab')2, Fv, single chain antibodies (e.g., scFv), minibodies and diabodies.

A "Fab fragment" comprises one light chain and the CH1 and variable regions of one heavy chain. The heavy chain of a Fab molecule cannot form a disulfide bond with another heavy chain molecule.

An "Fc" region contains two heavy chain fragments comprising the CH2 and CH3 domains of an antibody. The two heavy chain fragments are held together by two or more disulfide bonds and by hydrophobic interactions of the CH3 domains.

A "Fab' fragment" contains one light chain and a portion of one heavy chain that contains the VH domain and the CHI domain and also the region between the CHI and CH2 domains, such that an interchain disulfide bond can be formed between the two heavy chains of two Fab' fragments to form a F(ab')2 molecule.

A "F(ab')2 fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

In a particular embodiment, the target-binding molecule is single-chain Fv antibody ("scFv antibody"). scFv refers to antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun (1994) The Pharmacology of Monoclonal Antibodies, vol. 113, Rosenburg and Moore eds. Springer-Verlag, New York, pp. 269-315. See also, PCT Publication No. WO 88/01649 and U.S. Pat. Nos. 4,946,778 and 5,260,203. By way of example, the linker between the VH and VL domains of the scFvs disclosed herein comprise, e.g., GGGGSGGGGSGGGGSGGGGS (SEQ ID NO:37) or GGGGSGGGGSGGGGS (SEQ ID NO:38). As would be appreciated by those of skill in the art, various suitable linkers can be designed and tested for optimal function, as provided in the art, and as disclosed herein.

The scFv that is part of the PEBL molecule is not necessarily the same as the scFv that occurs in the context of, e.g., a chimeric antigen receptor (CAR) or a similar antibody-binding signaling receptor. In some embodiments, the scFv that is part of the PEBL molecule is the same as the scFv that occurs in the context of, e.g., a chimeric antigen receptor (CAR) or a similar antibody-binding signaling receptor.

In some embodiments, the nucleic acid comprising a nucleotide sequence encoding a target-binding molecule (e.g., an scFv in the context of a PEBL molecule) comprises one or more amino acid sequences that have at least 80%, at least 85%, at least 88%, at least 90%, at least 92%, at least 94%, at least 95%, at least 96%, at least 97%, at least 98%, at least 99%, or 100% sequence identity to any one or more of SEQ ID NOS:1 and 2.

The term "sequence identity" means that two nucleotide or amino acid sequences, when optimally aligned, such as by the programs GAP or BESTFIT using default gap weights, share at least, e.g., 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et ah, Current Protocols in Molecular Biology). One example of algorithm that is suitable for determining percent sequence identity and sequence similarity is the BLAST algorithm, which is described in Altschul et al, J. Mol. Biol. 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

In certain embodiments, the antibody (e.g., scFv) comprises $V_H$ and $V_L$ having amino acid sequences set forth in SEQ ID NO:1 and SEQ ID NO:2, respectively. In some embodiments, the antibody (e.g., scFv) comprises $V_H$ and $V_L$ having sequence that each have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the $V_H$ and $V_L$ sequences set forth in SEQ ID NO:1 and SEQ ID NO:2, respectively.

A "diabody" is a small antibody fragment with two antigen-binding sites. The fragments comprise a heavy chain variable region ($V_H$) connected to a light chain variable region ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described in, e.g., patent documents EP 404,097; WO 93/11161; and Holliger et al, (1993) Proc. Natl. Acad. Sci. USA 90: 6444-6448.

In certain embodiments, the antibody is a triabody or a tetrabody. Methods of designing and producing triabodies and tetrabodies are known in the art. See, e.g., Todorovska et al, J. Immunol. Methods 248(1-2):47-66, 2001.

A "domain antibody fragment" is an immunologically functional immunoglobulin fragment containing only the variable region of a heavy chain or the variable region of a light chain. In some instances, two or more VH regions are covalently joined with a peptide linker to create a bivalent domain antibody fragment. The two VH regions of a bivalent domain antibody fragment may target the same or different antigens.

In some embodiments, the antibody is modified or engineered. Examples of modified or engineered antibodies include chimeric antibodies, multiparatopic antibodies (e.g., biparatopic antibodies), and multispecific antibodies (e.g., bispecific antibodies).

As used herein, "multiparatopic antibody" means an antibody that comprises at least two single domain antibodies, in which at least one single domain antibody is directed against a first antigenic determinant on an antigen and at least one other single domain antibody is directed against a second antigenic determinant on the same antigen. Thus, for example, a "biparatopic" antibody comprises at least one single domain antibody directed against a first antigenic determinant on an antigen and at least one further single domain antibody directed against a second antigenic determinant on the same antigen.

As used herein, "multispecific antibody" means an antibody that comprises at least two single domain antibodies, in which at least one single domain antibody is directed against a first antigen and at least one other single domain antibody is directed against a second antigen (different from the first antigen). Thus, for example, a "bispecific" antibody is one that comprises at least one single domain antibody directed against a first antigen and at least one further single domain antibody directed against a second antigen, e.g., different from the first antigen.

In some embodiments, the antibodies disclosed herein are monoclonal antibodies, e.g., murine monoclonal antibodies. Methods of producing monoclonal antibodies are known in the art. See, for example, Pluckthun (1994) The Pharmacology of Monoclonal Antibodies, Vol. 113, Rosenburg and Moore eds. Springer-Verlag, New York, pp. 269-315.

In various embodiments, the target-binding molecule in the context of a PEBL molecule is a receptor or a ligand that binds to a target molecule. For example, that target-binding molecule can be a ligand that binds PD-1 (e.g., PD-L1 or PD-L2). Thus, as would be appreciated by those of skill in the art, the target-binding molecule can be an antibody, or a ligand/receptor that binds a target molecule.

As used herein, "operatively linked" in the context of a PEBL gene refers to a gene encoding a target-binding molecule directly in frame (e.g., without a linker) adjacent to one or more genes encoding one or more localizing domains. Alternatively, the gene encoding a target-binding molecule may be connected to one or more gene encoding one or more localizing domains through a linker sequence, as described herein.

As used herein, "linked" in the context of a PEBL protein refers to the joining of a first domain, e.g., a target-binding molecule to a second domain, e.g., a localizing domain. The linker can be an amino acid sequence. Various suitable linkers known in the art can be used to tether the target-binding molecule to a localizing domain. For example, non-naturally occurring peptides, such as a polypeptide consisting of hydrophilic residues of varying length, or a (GGGGS)$_n$ (SEQ ID NO:40) polypeptide, in which n is an integer of, e.g., 2-12, inclusive, can be used according to the present invention. In particular embodiments, the linker comprises, e.g., GGGGSGGGGS (SEQ ID NO: 39). In some embodiments, the linker comprises, e.g., GGGGSGGGGSGGGGSGGGGS (SEQ ID NO: 37). In various embodiments, peptide linkers having lengths of about 5 to about 100 amino acids, inclusive, can be used in the present invention. In certain embodiments, peptide linkers having lengths of about 20 to about 40 amino acids, inclusive, can be used in the present invention. In some embodiments, peptide linkers having lengths of at least 5 amino acids, at least 10 amino acids, at least 15 amino acids, at least 20 amino acids, at least 25 amino acids, at least 30 amino acids, at least 35 amino acids, or at least 40 amino acids can be used in the present invention. As would be appreciated by those of skill in the art, such linker sequences as well as variants of such linker sequences are known in the art. Methods of designing constructs that incorporate linker sequences as well as methods of assessing functionality are readily available to those of skill in the art.

In certain embodiments, the PEBL molecule binds to a target expressed on the surface of an immune cell. In some embodiments, the PEBL molecule inhibits the activity or function of the target molecule. By way of example, as disclosed herein, PEBL molecule can be designed to bind to, e.g., TCRα, TCRβ, CD3 (e.g., CD3ε, CD3γ, CD3δ, or CD3ζ), CD7, CD45, hB2MG, KIR2DL1, KIR2DL2/DL3, NKG2A, or NKG2D hereby downregulating the cell surface expression of such molecules. Downregulation of such molecules can be achieved through, for example, localizing/targeting the molecules for degradation and/or internalization. In other embodiments, the PEBL molecule renders the target inactive (e.g., the target can no longer interact and/or bind to its cognate ligand or receptor).

In some embodiments, the engineered immune cells of the present invention have enhanced therapeutic efficacy. As used herein, "enhanced therapeutic efficacy" refers to one or more of reduced graft-versus-host disease (GVHD) in a host or recipient, reduced or elimination of rejection by a host, extended survival in a host, reduced inhibition by the tumor in a host, reduced self-killing in a host, reduced inflammatory cascade in a host, or sustained CAR-mediated signal transduction in a host.

In certain embodiments of the present invention, the target-binding molecule in the context of a PEBL molecule binds to a molecule in a CD3/T-cell receptor (TCR) complex, a cytokine, a human MHC class I molecule, a human MHC claim II molecule, or a receptor that downregulates immune response.

In certain embodiments, a molecule in a CD3/TCR complex can be TCRα, TCRβ, TCRγ, TCRδ, CD3ε, CD3δ, CD3γ, or CD3ζ. In a particular embodiment, the molecule is CD3δ. In certain embodiments, the molecule is CD3γ. In some embodiments, the molecule is CD3ε. In a particular embodiment, the molecule is CD3ζ.

In another embodiment, the MHC class I molecule can be β-2 microglobulin, α1-microglobulin, α2-microglobulin, or α3-microglobulin.

In other embodiments, a receptor that downregulates immune response is selected from, e.g., PD-1, CTLA-4, TIM-1, TIM-3, killer immunoglobulin-like receptors (KIRs, e.g., KIR2DL1 (also known as CD158a), KIR2DL2/DL3 (also known as CD158b)), CD94 or NKG2A (also known as CD159a), protein tyrosine phosphatases such as Src homology region 2 domain-containing phosphatase (SHP)-1 and SHP-2. Thus, such receptors can be targeted by the targeting-binding molecule of a PEBL molecule, as described herein.

In various embodiments, examples of cytokines that can be targeted with targeting-binding molecule of a PEBL molecule include, e.g., interleukin (IL)-6, IL-2, IL-4, IL-7, IL-10, IL-12, IL-15, IL-18, IL-21, IL-27, IL-35, interferon (IFN)-γ, IFN-β, IFN-α, TNF-α, or TGF-β. In a further aspect, the PEBL molecule binds to a molecule selected from, e.g., CD2, CD4, CD5, CD7, CD8, CD30, CD38, CD45, CD52, or CD127. In certain aspects of the present invention, the PEBL can bind to a molecule that is expressed on the surface of a cell including, but not limited to members of the CD1 family of glycoproteins, CD2, CD3, CD4, CD5, CD7, CD8, CD25, CD28, CD30, CD38, CD45, CD45RA, CD45RO, CD52, CD56, CD57, CD99, CD127, and CD137. In some embodiments, the PEBL molecule specifically binds to CD3ε, CD3γ, CD3δ, or CD3ζ.

Methods of producing antibodies and antibody fragments thereof against any target protein are well-known and routine in the art. Moreover, as exemplified herein, commercially available antibodies to various targets, e.g., CD3 and CD7 can be used to generate a PEBL molecule, as exemplified herein. Antibodies known in the art, as well as fragments of antibodies (e.g., scFv) derived therefrom, can be used in the present invention, as exemplified herein.

In other aspects, the localizing domain of the PEBL molecule comprises an endoplasmic reticulum (ER) retention sequence KDEL (SEQ ID NO:32), or other ER or Golgi retention sequences such as KKXX (SEQ ID NO:35), KXD or KXE (where X can be any amino acid, see, e.g., Gao C, et al, Trends in Plant Science 19: 508-515, 2014) and YQRL (SEQ ID NO:34) (see Zhan J, et al, Cancer Immunol Immunother 46:55-60, 1998); a proteosome targeting sequence that comprises, e.g., "PEST" motif-SHGFPPEVE-EQDDGTLPMSCAQESGMDRHPAACASARINV (SEQ ID NO:41); and/or a sequence that targets the target-binding molecule to the cell membrane, such as the CD8a transmembrane domain, or the transmembrane of another single-pass membrane protein, as described herein (e.g., CD8α, CD8β, 4-1BB, CD28, CD34, CD4, FcsRIy, CD 16 (such as CD16A or CD16B), OX40, CD3ζ, CD3δ, CD3ε, CD3γ, CD35, TCRα, CD32 (such as CD32A or CD32B), CD64 (such as CD64A, CD64B, or CD64C), VEGFR2, FAS, or FGFR2B). Examples of particular localizing domains (sequences) exemplified herein are shown in FIG. 8a. Various other localizing sequences are known and available in the art, for example in WO2016/126213.

In some embodiments, the PEBL molecules of the present invention can comprise one or more localizing domains. For example, the PEBL molecule can have at least one, at least two, at least three, at least four, at least five, at least six, at least seven, at least eight, at least nine, or at least ten localizing domains linked together. When more than one localizing domain is used in a given PEBL molecule, each localizing domain can be linked with or without any intervening linker. In some instances, localization domains such as a CD8a transmembrane domain, KDEL motif, and a linker can be used in a single PEBL molecule. While this particular construct shows the localization domains without any intervening linkers, various intervening linkers can be incorporated between some or all of the localization domains. Other examples are shown in FIG. 8A.

As would be appreciated by those of skill in the art, the chimeric antigen receptor and/or the PEBL molecule can be designed to bind to the targets disclosed herein, as well as variants of the targets disclosed herein. By way of example, a chimeric antigen receptor and/or the PEBL molecule can be designed to bind to a molecule in a CD3/TCR complex, or a naturally-occurring variant molecule thereof. Such naturally-occurring variants can have the same function as the wild-type form of the molecule. In other embodiments, the variant can have a function that is altered relative to the wild-type form of the molecule (e.g., confers a diseased state).

As would be appreciated by those of skill in the art, the various components of the PEBL molecule constructs can be substituted in different combinations (e.g., to contain a different linker, different localizing sequence, different scFv, etc.), so long as the combination produces a functional PEBL. Methods of assessing functionality for a particular construct are within the ambit of those of skill in the art, as disclosed herein.

In further aspects, the present invention relates to the use of an engineered immune cell that comprises a nucleic acid comprising a nucleotide sequence encoding a PEBL molecule, and a nucleic acid comprising a nucleotide sequence encoding a chimeric antigen receptor for treating cancer, comprising administering a therapeutically effective amount of the engineered immune cell to a subject in need thereof.

In another aspect, the present invention relates to the use of an engineered immune cell that comprises a first nucleic acid comprising a nucleotide sequence encoding a chimeric antigen receptor (CAR) and a second nucleic acid comprising a nucleotide sequence encoding a single-chain variable fragment (scFv) linked to a localizing domain for treating cancer, comprising administering a therapeutically effective amount of the engineered immune cell to a subject in need thereof. In some embodiments, the first nucleic acid sequence and the second nucleic acid sequence are bicistronic.

In other aspects, the present invention relates to the use of an engineered immune cell that comprises a nucleic acid comprising a nucleotide sequence encoding a chimeric antigen receptor (CAR), and a nucleic acid comprising a nucleotide sequence encoding a target-binding molecule (e.g., scFv) linked to a localizing domain for treating an autoimmune disorder, comprising administering a therapeutically effective amount of the engineered immune cell to a subject in need thereof.

In other aspects, the present invention also relates to the use of an engineered immune cell that comprises a nucleic acid comprising a nucleotide sequence encoding a chimeric antigen receptor (CAR), and a nucleic acid comprising a nucleotide sequence encoding a target-binding molecule (e.g., scFv) linked to a localizing domain for treating an infectious disease, comprising administering a therapeutically effective amount of the engineered immune cell to a subject in need thereof.

In various embodiments, the chimeric antigen receptor is a CAR (e.g., anti-CD19-4-1-BB-CD3ζ CAR). In some embodiments, the PEBL molecule or single-chain variable fragment (scFv) linked to a localizing domain is selected from any one or more constructs shown in FIG. 8A.

3. ADMINISTRATION OF ENGINEERED IMMUNE CELLS

Provided herein are methods directed to reducing or ameliorating a disease or disorder by administering a therapeutically effective amount of the engineered immune cells expressing a PEBL and/or a CAR. In one embodiment, the engineered CD3/TCRαβ-negative T cells are administered to reduce the symptoms of, treat, or prevent cancer. In some embodiments, the engineered CD3/TCRαβ-negative T cells are administered to reduce the symptoms of, treat, or prevent an autoimmune disease. In other embodiments, the engineered CD3/TCRαβ-negative T cells are administered to treat or prevent graft-versus-host disease or transplant rejection upon undergoing transplant surgery.

The term "therapeutically effective amount" refers an amount of the engineered immune cells (e.g., engineered CD3/TCRαβ-negative T cells) of the present invention that, when administered to a patient, alleviates the signs and or symptoms of the disease (e.g., cancer, infection or GVHD). The actual amount to be administered can be determined based on studies done either in vitro or in vivo where the functional CD3/TCRαβ-negative T cells exhibit pharmacological activity against disease. For example, an amount of CD3/TCRαβ-negative T cells may be assayed for inhibition of target cell proliferation and the amount of CD3/TCRαβ-negative T cells that demonstrates inhibition can represent a therapeutically effective amount.

A "pharmaceutical composition" refers to a composition suitable for administration to a subject, e.g., a human subject. Such compositions may be specifically formulated for administration via one or more of a number of routes, including but not limited to buccal, intraarterial, intracardial, intracerebroventricular, intradermal, intramuscular, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, liquid, gel, drops, or other means of administration.

The engineered T cells according to the invention can be made into a pharmaceutical composition or made implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the engineered T cells can be formulated into a preparation in semisolid or liquid form, such as a capsule, solution, injection, inhalant, or aerosol, in the usual ways for their respective route of administration. In most cases, a pharmaceutically acceptable form is such that does not ineffectuate the cells expressing the PEBL and/or CAR. In some embodiments, the engineered T cells can be made into a pharmaceutical composition containing a balanced salt solution, preferably Hanks' balanced salt solution, or normal saline.

In some aspects, the engineered immune cell is administered by infusion into the subject. Methods of infusing immune cells (e.g., allogeneic or autologous immune cells) are known in the art. A sufficient number of cells are administered to the recipient in order to ameliorate the symptoms of the disease. Typically, dosages of $10^7$ to $10^{10}$ cells are infused in a single setting, e.g., dosages of $10^9$ cells. Infusions are administered either as a single $10^9$ cell dose or divided into several $10^9$ cell dosages. The frequency of infusions can be every 3 to 30 days or even longer intervals if desired or indicated. The quantity of infusions is generally at least 1 infusion per subject and preferably at least 3 infusions, as tolerated, or until the disease symptoms have been ameliorated. The cells can be infused intravenously at a rate of 50-250 ml/hr. Other suitable modes of administration include intra-arterial infusion, direct injection into tumor and/or perfusion of tumor bed after surgery, implantation at the tumor site in an artificial scaffold, intrathecal administration, and intraocular administration. Methods of adapting the present invention to such modes of delivery are readily available to one skilled in the art.

In certain aspects, the cancer to be treated is a solid tumor or a hematologic malignancy. Examples of hematologic malignancies include acute myeloid leukemia, chronic myelogenous leukemia, myelodysplasia, acute lymphoblastic leukemia, chronic lymphocytic leukemia, multiple myeloma, Hodgkin and non-Hodgkin lymphoma. Examples of solid tumors include lung cancer, melanoma, breast cancer, prostate cancer, colon cancer, renal cell carcinoma, ovarian cancer, pancreatic cancer, hepatocellular carcinoma, neuroblastoma, rhabdomyosarcoma, and brain tumor.

4. PRODUCTION OF ENGINEERED IMMUNE CELLS

In another embodiment, the present invention relates to a method for producing an engineered immune cell of the present invention, comprising introducing into an immune cell a nucleic acid comprising a nucleotide sequence encoding a chimeric antigen receptor, and a nucleic acid comprising a nucleotide sequence encoding a target-binding molecule linked to a localizing domain (e.g., a PEBL molecule), thereby producing an engineered immune cell.

In certain embodiments, the nucleic acid comprising a nucleotide sequence is introduced into an immune cell ex vivo or in vitro. In other embodiments, the nucleic acid comprising a nucleotide sequence is introduced into an immune cell in vivo.

In some embodiments, the nucleic acids described herein are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. The nucleic acid encoding the target-binding molecule can be operably linked to the nucleic acid encoding the localizing domain. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art. If such sites do not exist, the synthetic oligonucleotide adapters or linkers are used in accordance with conventional practice.

In some embodiments, an "immune cell" includes, e.g., T cell such as but not limited to, a cytotoxic T cell, a helper T cell, a regulatory T cell, effector T cell, memory T cell, natural killer T cell, gamma delta T cell, and the like.

Figure 13A:
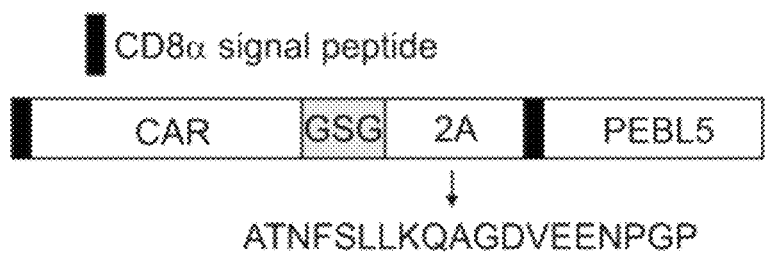
FIG. 13A-FIG. 13C. Development of a bicistronic vector delivering CAR and PEBL constructs.

The nucleic acid comprising a nucleotide sequence to be introduced can be a single bicistronic construct containing a chimeric antigen receptor described herein and a target-binding molecule (e.g., scFv) linked to a localizing domain. As described herein, a single bicistronic construct can be prepared by inserting an internal ribosomal entry site (IRES) or a 2A peptide-coding region site between the two cDNAs encoding the chimeric antigen receptor as described herein (e.g., CAR) and the target-binding molecule (e.g., scFv). In some embodiments, the bicistronic construct includes a CAR upstream of a PEBL with an IRES or 2A peptide coding region between them. In some cases, an illustrative bicistronic construct is represented FIG. 13A. In other embodiments, the bicistronic construct includes a PEBL upstream of a CAR upstream with an IRES or 2A peptide coding region between them. The design of tricistronic delivery systems to delete more than one target should also be feasible. Alternatively, separate transductions (simultaneously or sequentially) of the individual constructs (e.g., CAR and PEBL) could be performed. Methods of introducing exogenous nucleic acids are exemplified herein, and are well-known in the art.

The nucleic acids described herein can be introduced (directly transduced) into a cell using retroviral and lentiviral vector constructs. The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art. In other embodiments, the nucleic acids can be directly transfected into a cell. In yet other embodiments, the nucleic acids can be electroporated into a cell. Detailed methods for electroporation are described, e.g., in Roth et al., Nature, 2018, 559: 405-409 and Van Tendello et al., Gene Therapy, 2000, 7, 1431-1437.

As used herein, the indefinite articles "a" and "an" should be understood to mean "at least one" unless clearly indicated to the contrary.

The engineered immune cells described herein can comprise a target-binding molecule linked to a localizing domain that binds to CD3, as described in WO2016/126213. The sequences of the components of anti-CD3 PEBLs as described in FIG. 2 and Tables 1 and 2 of WO2016/126213 and Table 1 below.

TABLE 1

Sequence information for components of an anti-CD3ε target-binding molecule linked to a localizing domain.

| Component | Sequence |
| --- | --- |
| CD8 signal peptide | MALPVTALLLPLALLLHAARP (SEQ ID NO: 5) |
| VH-VL Linker | GGGGSGGGGSGGGGSGGGGS (SEQ ID NO: 6) |
| CD8α Transmembrane amino acid | KPTTTPAPRPPTPAPTIASQPLSLRPEA CRPAAGGAVHTRGLDFACDIYIWAPLAG TCGVLLLSLITLY (SEQ ID NO: 7) |
| CD8 signal peptide cDNA | ATGGCCTTACCAGTGACCGCCTTGCTCC TGCCGCTGGCCTTGCTGCTCCACGCCGC CAGGCCG (SEQ ID NO: 8) |
| VH-VL linker cDNA | GGTGGTGGTGGTTCTGGTGGTGGTGGTT CTGGCGGCGGCGGCTCCGGTGGTGGTGG ATCC (SEQ ID NO: 9) |
| CD8 transmembrane cDNA | AAGCCCACCACGACGCCAGCGCCGCGAC CACCAACACCGGCGCCCACCATCGCGTC GCAGCCCCTGTCCCTGCGCCCAGAGGCG TGCCGGCCAGCGGCGGGGGGCGCAGTGC ACACGAGGGGGCTGGACTTCGCCTGTGA TATCTACATCTGGGCGCCCTTGGCCGGG ACTTGTGGGTCCTTCTCCTGTCACTGG TTATCACCCTTTAC (SEQ ID NO: 10) |

TABLE 1-continued

Sequence information for components of an anti-CD3ε target-binding molecule linked to a localizing domain.

| Component | Sequence |
| --- | --- |
| VH amino acid sequence | EVQLQQSGAELARPGASVKMSCKASGYT FTRYTMHWVKQRPGQGLEWIGYINPSRG YTNYNQKFKDKATLTTDKSSSTAYMQLS SLTSEDSAVYYCARYYDDHYCLDYWGQG TTLTVSSA (SEQ ID NO: 1) |
| VL amino acid sequence | QIVLTQSPAIMSASPGEKVTMTCSASSS VSYMNWYQQKSGTSPKRWIYDTSKLASG VPAHFRGSGSGTSYSLTISGMEAEDAAT YYCQQWSSNPFTFGSGTKLEINR (SEQ ID NO: 2) |
| VH nucleotide sequence | GAGGTCCAGCTGCAGCAGTCTGGGGCTG AACTGGCAAGACCTGGGGCCTCAGTGAA GATGTCCTGCAAGGCTTCTGGCTACACC TTTACTAGGTACACGATGCACTGGGTAA AACAGAGGCCTGGACAGGGTCTGGAATG GATTGGATACATTAATCCTAGCCGTGGT TATACTAATTACAATCAGAAGTTCAAGG ACAAGGCCACATTGACTACAGACAAATC CTCCAGCACAGCCTACATGCAACTGAGC AGCCTGACATCTGAGGACTCTGCAGTCT ATTACTGTGCAAGATATTATGATGATCA TTACTGCCTTGACTACTGGGGCCAAGGC ACCACTCTCACAGTCTCCTCAGCC (SEQ ID NO: 3) |
| VL nucleotide sequence | CAAATTGTTCTCACCCAGTCTCCAGCAA TCATGTCTGCATCTCCAGGGGAGAAGGT CACCATGACCTGCAGTGCCAGCTCAAGT GTAAGTTACATGAACTGGTACCAGCAGA AGTCAGGCACCTCCCCCAAAAGATGGAT TTATGACACATCCAAACTGGCTTCTGGA GTCCCTGCTCACTTCAGGGGCAGTGGGT CTGGGACCTCTTACTCTCTCACAATCAG CGGCATGGAGGCTGAAGATGCTGCCACT TATTACTGCCAGCAGTGGAGTAGTAACC CATTCACGTTCGGCTCGGGGACAAAGTT GGAAATAAACCGG (SEQ ID NO: 4) |

5. GENOME EDITING TO PRODUCE CD3/TCRαβ-NEGATIVE IMMUNE CELLS

As noted above, downregulation of expression of an immune molecule on an effector T cells can be achieved according to a variety of other known methods including, for example, gene editing methods with meganucleases, TALEN, CRISPR/Cas9, and zinc finger nucleases. Thus, in certain embodiments, the engineered immune cell further comprises a modified gene, which modification renders a target gene or protein non-functional. By way of example, the engineered immune cell of the present invention further comprises a modified (e.g., non-functional) TCRα gene, TCRβ gene, or CD3 gene (modified using, e.g., meganucleases, TALEN, CRISPR/Cas9, or zinc finger nucleases) that prevents or reduces expression of CD protein, and/or otherwise impairs (e.g., structurally) the CD protein from being recognized by or interfering with the CAR. Methods of modifying gene expression using such methods are readily available and well-known in the art.

Methods of inactivating a target gene in an immune cell using CRISPR/Cas6 technology are described, for example, in US Patent Publication Nos. US2016/0272999, US2017/0204372, and US2017/0119820.

The CRISPR/Cas system is a system for inducing targeted genetic alterations (genome modifications). Target recognition by the Cas9 protein requires a "seed" sequence within the guide RNA (gRNA) and a conserved multinucleotide containing protospacer adjacent motif (PAM) sequence upstream of the gRNA-binding region. The CRISPR/Cas system can thereby be engineered to cleave substantially any DNA sequence by redesigning the gRNA in cell lines, primary cells, and engineered cells. The CRISPR/Cas system can simultaneously target multiple genomic loci by co-expressing a single Cas9 protein with two or more gRNAs, making this system uniquely suited for multiple gene editing or synergistic activation of target genes. Examples of a CRISPR/Cas system used to inhibit gene expression are described in U.S. Publication No.: 2014/0068797 and U.S. Pat. Nos. 8,697,359 and 8,771,945. The system induces permanent gene disruption that utilizes the RNA-guided Cas9 endonuclease to introduce DNA double stranded breaks which trigger error-prone repair pathways to result in frame shift mutations. In some cases, other endonucleases may also be used, including but not limited to, Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, T7, Fok1, other nucleases known in the art, homologs thereof, or modified versions thereof.

CRISPR/Cas gene disruption occurs when a gRNA sequence specific for a target gene and a Cas endonuclease are introduced into a cell and form a complex that enables the Cas endonuclease to introduce a double strand break at the target gene. In some instances, the CRISPR system comprises one or more expression vectors comprising a nucleic acid sequence encoding the Cas endonuclease and a guide nucleic acid sequence specific for the target gene. The guide nucleic acid sequence is specific for a gene and targets that gene for Cas endonuclease-induced double strand breaks. The sequence of the guide nucleic acid sequence may be within a loci of the gene. In some embodiment, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40, 45, 50, or more nucleotides in length. The guide nucleic acid sequence includes a RNA sequence, a DNA sequence, a combination thereof (a RNA-DNA combination sequence), or a sequence with synthetic nucleotides, such as a peptide nucleic acid (PNA) or Locked Nucleic Acid (LNA). The guide nucleic acid sequence can be a single molecule or a double molecule. In one embodiment, the guide nucleic acid sequence comprises a single guide RNA.

In some embodiments, the engineered immune cell of the present invention can be modified via the CRISPR/Cas system to inactivate the human CD3 gene. Details of the genomic structure and sequence of the human CD3 gene can be found, for example, in NCBI Gene database under GeneID Nos. 6955 (TCRα), 6957 (TCRβ), 915 (CD3δ), 916 (CD3ε), 917 (CD3γ), and 919 (CD3ζ).

Commercially available kits, gRNA vectors and donor vectors, for knockout of specific target genes are available, for example, from Origene (Rockville, Md.), GenScript (Atlanta, Ga.), Applied Biological Materials (ABM; Richmond, British Colombia), BioCat (Heidelberg, Germany) or others. For example, commercially available kits or kit components for knockout of CD3δ via CRISPR include, for example, those available as catalog numbers KN210010, KN210010G1, KN210010G2, and KN210010D, for knockout of CD3εδ via CRISPR include, for example, those available as catalog numbers KN208276, KN208276G1, KN208276G2, and KN208276D, for knockout of CD3γ via CRISPR include, for example, those available as catalog numbers KN220512, KN220512G1, KN220512G2, and KN220512D, each available from OriGene. Also, commercially available kits or kit components available from Santa Cruz Biotechnology for knockout of CD3ζ via CRISPR include, for example, those available as catalog numbers sc-419554, sc-419554-HDR, sc-419554-NIC, and sc-419554-NIC2.

In some embodiments, the CRISPR/Cas system can be used to introduce any of the nucleic acid outlined herein into the genome of an immune cell, e.g., a T cell.

6. DETAILED DESCRIPTION OF EXEMPLARY EMBODIMENTS

In certain embodiments, provided is an engineered immune cell comprising: (i) a nucleic acid comprising a nucleotide sequence encoding a target-binding molecule linked to a localizing domain (e.g., PEBL), wherein the target-binding molecule is an antibody that binds CD3, and the localizing domain comprises a retention signal domain comprising an amino acid sequence selected from the group consisting of an endoplasmic reticulum (ER) sequence, a Golgi retention sequence, a proteosome localizing sequence, and a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In some instances, another nucleic acid comprising a nucleotide sequence encoding a chimeric antigen receptor (CAR). In certain cases, the CAR comprises intracellular signaling domains of 4-1BB and CD3ζ, and an antibody that binds Cluster of Differentiation 19 (CD19). In certain embodiments, the antibody that binds CD3 in the context of the target-binding molecule comprises: a $V_H$ sequence set forth in SEQ ID NO:1 and a $V_L$ sequence set forth in SEQ ID NO:2. As described herein, in certain embodiments, the antibody comprises a $V_H$ and a $V_L$ having sequence that each have at least 95% sequence identity, at least 96% sequence identity, at least 97% sequence identity, at least 98% sequence identity, at least 99% sequence identity, or 100% sequence identity to the VH and VL sequences set forth in SEQ ID NO:1 and SEQ ID NO:2, respectively. In some cases, the antibody is a single chain variable fragment (scFv). In some embodiments, the localizing domain of the PEBL comprises an amino acid sequence set forth in FIG. 8A or Table 1. In certain embodiments, the CAR further comprises a hinge and transmembrane sequence.

In some embodiments, the engineered immune cell is an engineered T cell (e.g., engineered cytotoxic T cell, engineered helper T cell, engineered regulatory T cell, engineered effector T cell, engineered memory T cell, engineered natural killer T cell, and engineered gamma delta T cell), an engineered natural killer (NK) cell, an engineered NK/T cell, an engineered monocyte, an engineered macrophage, or an engineered dendritic cell. In some cases, the engineered immune cell is an allogeneic cell. In other cases, the engineered immune cell is an autologous cell.

In some embodiments, the engineered immune cell lacks CD3/TCRαβ expression for at least 6 months, e.g., 6 months, 7 months, 8 months, 9 months, 10 months, 11 months, 12 months, 13 months, 14 months, 15 months, 16 months, 17 months, or more. In other embodiments, the engineered immune cell lacks CD3/TCRαβ expression for at least 12 months, e.g., 12 months, 13 months, 14 months, 15 months, 16 months, 17 months, 18 months, 19 months, 20 months, 22 months, 23 months, 24 months, or more. In particular embodiments, the engineered immune cell lacks CD3/TCRαβ expression for at least 20 months, e.g., 20 months, 22 months, 23 months, 24 months, 25 months, 26 months, 27 months, 28 months, 29 months, 30 months, 31 months, 32 months, or more.

In certain embodiments, the engineered immune cell proliferates at a substantially equal rate compared to a comparable immune cell.

The engineered cells of the present invention can be expanded in a culture media under specific conditions. In some embodiments, the engineered cells are cultured in the presence of IL-2. The engineered cells can be cryopreserved according to any method recognized by one skilled in the art. Prior to administration to the patient, the engineered calls can be thawed and cultured. In other cases, the engineered calls can also be expanded prior administration.

In some embodiments, a subject has a reduced likelihood of developing graft-versus-host-disease when the engineered immune cell is administered to the subject, wherein the engineered immune cell is allogeneic to said subject. The engineered immune cell can induce cytotoxicity of CD19+ leukemic cells.

In some aspects, also provided is a substantially pure population of engineered immune cells comprising any one of the engineered immune cells described herein, wherein at least 90%, e.g., at least 90%, 91%, 92%, 93%, 94%, 95%, 96%, 97%, 98%, 99% or more of the engineered immune cells lack CD3/TCRαβ expression. In some cases, the substantially pure population comprises at least 80%, e.g., at least 80%, 81%, 82%, 83%, 84%, 85%, 86%, 87%, 88%, 89%, 90%, 91%, 92%, 93%, 94%, 95%, 96%, 97%, 98%, 99%, or more engineered immune cells lacking CD3/TCRαβ expression.

In some aspects, also provided is a nucleic acid comprising a nucleotide sequence encoding a target-binding molecule linked to a localizing domain (e.g., PEBL), wherein the target-binding molecule is an antibody that binds CD3, and the localizing domain comprises retention signal domain is an amino acid sequence selected from the group consisting of an endoplasmic reticulum (ER) sequence, a Golgi retention sequence, a proteosome localizing sequence, and a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In some cases, provided is an expression vector comprising the nucleic acid described herein. In some instances, provided is a host cell comprising the expression vector.

In other aspects, also provided is a method of treating cancer in a subject in need thereof, comprising administering a therapeutically effective amount of an engineered immune cell having any of the embodiments described herein to the subject, thereby treating cancer in a subject in need thereof. In some aspects, provided is a method of treating cancer in a subject in need thereof, comprising administering a therapeutically effective amount of a substantially pure population of engineered immune cells having any of the embodiments described herein to the subject, thereby treating cancer in a subject in need thereof.

In some embodiments, also provided is a method of treating an autoimmune disease in a subject in need thereof, comprising administering a therapeutically effective amount of an engineered immune cell having any of the embodiments described herein to the subject, thereby treating an autoimmune disease in a subject in need thereof. In some embodiments, provided is a method of treating an autoimmune disease in a subject in need thereof, comprising administering a therapeutically effective amount of a substantially pure population of engineered immune cells having any of the embodiments described herein to the subject, thereby treating an autoimmune disease in a subject in need thereof.

In certain embodiments, the method comprises administering a therapeutically effective amount of an engineered immune cell comprising a nucleic acid having a nucleotide sequence encoding a target-binding molecule linked to a localizing domain, as described herein. In some instances, a second nucleic acid comprises a nucleotide sequence encoding a CAR. In some embodiments, the CAR comprises intracellular signaling domains of 4-1BB and CD3ζ, and an antibody that binds a cytokine such as CD19 or CD3.

In certain embodiments, the cancer includes, but is not limited to, a CD3-positive cancer, a CD19-positive cancer, a solid tumor cancer, a blood cancer, a B-cell malignancy, e.g., a B-cell acute lymphocytic leukemia, a lymphoblastic leukemia, a B-cell chronic lymphocytic leukemia, a B-cell non-Hodgkin's lymphoma.

As used herein, the terms "treat," "treating," or "treatment," refer to counteracting a medical condition (e.g., a condition related to a malignancy, autoimmune disease, graft-versus-host disease, transplantation rejection, viral infection, infectious disease, etc.) to the extent that the medical condition is improved according to a clinically-acceptable standard.

The term "subject" or "patient," used interchangeably, refers to a mammal (e.g., human, non-human primate, cow, sheep, goat, horse, dog, cat, rabbit, guinea pig, rat, mouse). In certain embodiments, the subject is a human. A "subject in need thereof" refers to a subject (e.g., patient) who has, or is at risk for developing, a disease or condition that can be treated (e.g., improved, ameliorated, prevented) by inducing T cells to exert specific cytotoxicity against target cells.

As defined herein, a "therapeutically effective amount" refers to an amount that, when administered to a subject, is sufficient to achieve a desired therapeutic effect (treats a condition related to a T cell malignancy) in the subject under the conditions of administration. An effective amount of the agent to be administered can be determined by a clinician of ordinary skill using the guidance provided herein and other methods known in the art, and is dependent on several factors including, for example, the particular agent chosen, the subject's age, sensitivity, tolerance to drugs and overall well-being.

In some embodiments, the engineered immune cell is autologous to the subject in need of treatment, e.g., cancer treatment, autoimmune disease treatment, infectious disease treatment, GVHD treatment, and transplantation rejection treatment. In other embodiments, the engineered immune cell is allogenic to the subject in need of treatment. The isolated engineered immune cell of the present invention can be an "off-the-shelf" immune cell that can be administered to a plurality of subjects and provides a reduced risk of GVHD. In some embodiments, the engineered immune cell does not elicit a GVHD response upon administration to a plurality of subjects (e.g., at least two more more subjects).

In certain embodiments, the engineered immune cell is administered into the subject by intravenous injection, intravenous infusion, intraarterial infusion, subcutaneous injection, intramuscular injection, intrasternal injection, intratumoral injection, direct injection into tumor and/or perfusion of tumor bed after surgery, implantation at a tumor site in an artificial scaffold, intrathecal administration, and intraocular administration.

In certain embodiments, the engineered immune cell is administered by infusion into the subject. Methods of infusing immune cells (e.g., allogeneic or autologous immune cells) are known in the art. A sufficient number of cells are administered to the recipient in order to ameliorate the symptoms of the disease. Typically, dosages of $10^7$ to $10^{10}$ cells are infused in a single setting, e.g., dosages of $10^9$ cells. Infusions are administered either as a single $10^9$ cell dose or divided into several $10^9$ cell dosages. The frequency of infusions can be daily, every 2 to 30 days or even longer intervals if desired or indicated. The quantity of infusions is generally at least 1 infusion per subject and preferably at least 3 infusions, as tolerated, or until the disease symptoms have been ameliorated. The cells can be infused intravenously at a rate of 50-250 ml/hr. Other suitable modes of administration include intra-arterial infusion, intraperitoneal infusion, direct injection into tumor and/or perfusion of tumor bed after surgery, implantation at the tumor site in an artificial scaffold, intrathecal administration. Methods of adapting the present invention to such modes of delivery are readily available to one skilled in the art.

In certain embodiments, the method of treating cancer according to the present invention is combined with at least one other known cancer therapy, e.g., chemotherapy.

In other aspects, also provided is use of an engineered immune cell having any of the embodiments described herein for treating cancer, comprising administering a therapeutically effective amount of the engineered immune cell to a subject in need thereof. In certain embodiments, the cancer is a B cell malignancy. In certain embodiments, the B cell malignancy is acute lymphoblastic leukemia (ALL), chronic lymphocytic leukemia, or non-Hodgkin lymphoma.

In certain embodiments, the engineered immune cell is administered into the subject by intravenous infusion, intra-arterial infusion, intraperitoneal infusion, direct injection into tumor and/or perfusion of tumor bed after surgery, implantation at a tumor site in an artificial scaffold, or intrathecal administration.

In some embodiments, the nucleotide sequence encoding a CAR and the nucleotide sequence encoding a PEBL are introduced sequentially. In other embodiments, the nucleotide sequence encoding a CAR and the nucleotide sequence encoding a PEBL are introduced simultaneously. In certain cases, the nucleotide sequence encoding a CAR and the nucleotide sequence encoding a PEBL are operatively linked, and thus can be introduced on a single expression vector or plasmid.

In certain aspects, provided herein is a nucleic acid comprising a nucleotide sequence encoding a target-binding molecule linked to a localizing domain (e.g., PEBL). In some embodiments, the target-binding molecule is an antibody that binds a CD3/TCRαβ complex protein, the localizing domain comprises a retention signaling domain comprising an amino acid sequence selected from the group consisting of an ER sequence, a Golgi retention sequence, and a proteosome localizing sequence. The CD3/TCRαβ complex protein can be selected from TCRα, TCRβ, CD3ε, CD3δ, CD3γ, and CD3. The antibody that binds a CD3/TCRαβ complex protein can be a scFv. In some instance, the scFv comprises a variable heavy chain ($V_H$) sequence having at least 95% sequence identity to SEQ ID NO:1 and a variable light chain (VL) sequence having at least 95% sequence identity to SEQ ID NO:2. In certain instances, the scFv comprises a variable heavy chain (VH) sequence set forth in SEQ ID NO:1 and a variable light chain (VL) sequence set forth in SEQ ID NO:2. As described above, the engineered immune cell can be an allogeneic immune cell. For instance, the engineered immune cell can be used as an "off-the-shelf" immune cell. In other embodiments, the engineered immune cell is an autologous immune cell. The transmembrane domain can comprise a transmembrane domain derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. For instance, transmembrane domain comprises the transmembrane domain from CD8α. In some embodiments, the retention signaling domain comprises an amino acid sequence selected from KDEL, KKMP, KKTN, or KKXX, wherein X can be any amino acid. The localizing domain can comprise an amino acid sequence set forth in FIG. 8A or Table 1. In other aspects, provided is an expression vector comprising a nucleic acid outlined herein. In certain aspects, provided is a host cell comprising an expression vector described herein.

In another aspect, provided is a method for producing the engineered immune cell. The method comprises introducing into an immune cell the nucleic acid outlined herein. The immune cell can be a T cell. In some cases, the immune cell is an allogeneic cell. In some embodiments, the method further comprises introducing a nucleic acid encoding a chimeric antigen receptor (CAR) into the immune cell. In some embodiments, the nucleic acid of the PEBL is operatively linked to the nucleic acid encoding the CAR. In other embodiments, the nucleic acid of the PEBL and the nucleic acid encoding the CAR are arranged for bicistronic expression (e.g., both nucleic acid sequences are expressed from the same RNA transcript).

In yet another aspect, provided is a polypeptide comprising a target-binding molecule linked to a localizing domain, wherein the localizing domain comprises a retention signaling domain comprising an amino acid sequence selected from the group consisting of an endoplasmic reticulum (ER) sequence, a Golgi retention sequence, and a proteosome localizing sequence, and a transmembrane domain derived from CD8α, and the polypeptide is not secreted by the cell and is not expressed on the cell surface of the cell. As such, the polypeptide remains within the cell and does not interact or bind to neighboring cells (e.g., cancer cells). In some cases, the C-terminal end of the target-binding molecule is connected to the N-terminal end of the localizing domain. The target-binding molecule can specifically bind a checkpoint inhibitor, a CD protein, or a T cell antigen. The target-binding molecule may be an antibody, such as a single chain variable fragment or scFv. In some instances, the scFv comprises a variable heavy chain (VH) sequence having at least 95% sequence identity to SEQ ID NO:1 and a variable light chain (VL) sequence having at least 95% sequence identity to SEQ ID NO:2. In certain instances, the scFv comprises a variable heavy chain (VH) sequence set forth in SEQ ID NO:1 and a variable light chain (VL) sequence set forth in SEQ ID NO:2. In some embodiments, the retention signaling domain comprises an amino acid sequence selected from KDEL, KKMP, KKTN, or KKXX, wherein X can be any amino acid. The localizing domain can comprise an amino acid sequence set forth in FIG. 8A or Table 1. In some embodiments, provided herein is a polynucleotide encoding such a polypeptide. In other embodiments, provided herein is an expression vector comprising such a polynucleotide outlined herein. In certain embodiments, provided is a host cell comprising the expression vector described herein.

In various aspects, also provided is a kit for producing an engineered immune cell described herein. The present kit can be used to produce, e.g., allogeneic or autologous effector T cells, allogeneic or autologous cytotoxic T cells, allogeneic or autologous helper T cells, allogeneic or autologous regulatory T cells, and the like.

Accordingly, provided herein is a kit comprising a nucleic acid comprising a nucleotide sequence encoding PEBL such as an anti-CD3ε PEBL. In some embodiments, the kit comprising a nucleic acid comprising a nucleotide sequence encoding a PEBL such as an anti-CD3ε PEBL, and a nucleic acid comprising a nucleotide sequence encoding a CAR. The kit can be designed according to any of the embodiments described herein.

In certain embodiments, the nucleotide sequence encoding the CAR and/or the nucleotide sequence encoding the PEBL further comprise sequences (e.g., plasmid or vector sequences) that allow, e.g., cloning and/or expression. For example, the nucleotide sequence can be provided as part of a plasmid for ease of cloning into other plasmids and/or vectors for, e.g., transfection into a cell (e.g., an immune cell). In certain embodiments, the nucleotide sequence encoding the CAR and the nucleotide sequence encoding the PEBL are provided on a single plasmid or vector. In certain embodiments, the nucleotide sequences are provided on separate plasmids or vectors.

In some embodiments, the kit further comprises a component or reagent for isolating CD3/TCRαβ-negative immune cell. In particular embodiments, the kit comprises an anti-CD3 antibody or an anti-TCRαβ antibody. CD3/TCRαβ-negative immune cells can be isolated from a population of cell by removing CD3/TCRαβ-positive cells. The kit can also include a solid support attached to an anti-CD3 antibody that binds CD3/TCRαβ-positive cells. In various embodiments, the kit can include a solid support attached to an anti-TCRαβ antibody that binds CD3/TCRαβ-positive cells.

Typically, the kits are compartmentalized for ease of use and can include one or more containers with reagents. In certain embodiments, all of the kit components are packaged together. Alternatively, one or more individual components of the kit can be provided in a separate package from the other kits components. The kits can also include instructions for using the kit components.

The disclosures of WO 2016/126213 and Kamiya et al., Blood Advances, 2018, 2(8):517-528 are incorporated herein by reference in their entirety for all purposes.

Provided herein are exemplary embodiments as set forth below.

Embodiment 1

An engineered CD3/TCRαβ-negative T cell comprising a polypeptide comprising a target-binding molecule linked to a localizing domain, wherein the target-binding molecule comprises an antibody that binds a CD3/TCRαβ complex protein, wherein the localizing domain comprises a retention signaling domain comprising an amino acid sequence selected from the group consisting of an endoplasmic reticulum (ER) retention sequence, a Golgi retention sequence, and a proteosome localizing sequence, and wherein the target-binding molecule linked to the localizing domain is not secreted by the engineered cell.

Embodiment 2

The engineered T cell of embodiment 1, wherein the CD3/TCRαβ complex protein is selected from the group consisting of TCRα, TCRβ, CD3ε, CD3δ, CD3γ, and CD3ζ.

Embodiment 3

The engineered immune cell of embodiment 1 or 2, wherein the antibody is a single chain variable fragment (scFv).

Embodiment 4

The engineered T cell of embodiment 3, wherein the scFv comprises a variable heavy chain (VH) sequence having at least 95% sequence identity to SEQ ID NO:1 and a variable light chain (VL) sequence having at least 95% sequence identity to SEQ ID NO:2.

Embodiment 5

The engineered T cell of embodiment 3, wherein the scFv comprises a variable heavy chain (VH) sequence set forth in SEQ ID NO:1 and a variable light chain (VL) sequence set forth in SEQ ID NO:2.

Embodiment 6

The engineered T cell of any one of embodiments 1 to 5, wherein the engineered T cell is an engineered CD4+ T cell or an engineered CD8+ T cell.

Embodiment 7

The engineered T cell of any one of embodiments 1 to 5, wherein the engineered T cell is an engineered helper T cell or an engineered regulatory T cell.

Embodiment 8

The engineered T cell of any one of embodiments 1 to 5, wherein the engineered T cell is an engineered effector T cell or an engineered memory T cell.

Embodiment 9

The engineered T cell of any one of embodiments 1 to 8, wherein the engineered T cell is an allogeneic T cell.

Embodiment 10

The engineered T cell of any one of embodiments 1 to 8, wherein the engineered T cell is an autologous T cell.

Embodiment 11

The engineered T cell of any one of embodiments 1 to 10, wherein the localizing domain further comprises a transmembrane domain selected from a transmembrane domain derived from CD8□, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B.

Embodiment 12

The engineered T cell of embodiment 11, wherein the transmembrane domain is the transmembrane domain derived from CD8α.

Embodiment 13

The engineered T cell of any one of embodiments 1 to 12, wherein the ER retention sequence comprises an amino acid sequence selected from KDEL (SEQ ID NO:32), KKMP (SEQ ID NO:33), KKTN (SEQ ID NO:43), or KKXX, wherein X is any amino acid (SEQ ID NO:35).

Embodiment 14

The engineered T cell of any one of embodiments 1 to 13, wherein the localizing domain comprises an amino acid sequence selected from any one in FIG. 8A or any one of SEQ ID NOS:11-31.

Embodiment 15

The engineered T cell of any one of embodiments 1 to 14, wherein CD3/TCRαβ expression is blocked in the engineered T cell.

Embodiment 16

The engineered T cell of embodiment 15, wherein the blockage of CD3/TCRαβ expression persists for at least 6 months or for at least 12 months.

Embodiment 17

The engineered T cell of any one of embodiments 1 to 16, wherein the engineered T cell proliferates at a substantially equivalent rate as a comparable T cell.

Embodiment 18

The engineered T cell of any one of embodiments 1 to 17, wherein the engineered T cell elicits a reduced graft-versus-host response in a subject upon administration of the cell.

Embodiment 19

The engineered T cell of any one of embodiments 1 to 18, wherein the engineered T cell further comprises a chimeric antigen receptor (CAR).

Embodiment 20

The engineered T cell of embodiment 19, wherein the CAR comprises an anti-CD19 scFv domain, a 4-1BB stimulatory signaling domain, and a CD3t signaling domain.

Embodiment 21

The engineered T cell of embodiment 20, wherein the engineered T cell induces cytotoxicity of CD19+ cancer cells.

Embodiment 22

The engineered T cell of embodiment 19, wherein the CAR comprises an anti-CD3 scFv domain, a 4-1BB stimulatory signaling domain, and a CD3t signaling domain.

Embodiment 23

The engineered T cell of embodiment 22, wherein the engineered T cell induces cytotoxicity of CD3+ cancer cells.

Embodiment 24

A substantially pure population of engineered T cells comprising any one of the engineered T cells of embodiments 1 to 23, wherein at least 90% of the engineered T cells exhibit blockage of CD3/TCRαβ expression.

Embodiment 25

The substantially pure population of engineered T cells of claim 24, wherein at least 95% of the engineered T cells exhibit blockage of CD3/TCRαβ expression.

Embodiment 26

A method of treating an autoimmune disease or a viral disease in a patient in need thereof, comprising administering a therapeutically effective amount of a pharmaceutical composition comprising the engineered T cells of any one of embodiments 1 to 18 to the patient with an autoimmune disease or a viral disease.

Embodiment 27

A method of reducing or eliminating the likelihood of graft-versus-host disease in a patient, comprising administering a therapeutically effective amount of a pharmaceutical composition comprising the engineered T cells of any one of embodiments 1 to 18 to the patient.

Embodiment 28

The method of embodiment 26 or 27, wherein administering comprises intravenous, intramuscular, subcutaneous, intraarterial, intraperitoneal, or intrathecal administration.

Embodiment 29

A method of treating cancer in a patient in need thereof, comprising administering a therapeutically effective amount of a pharmaceutical composition comprising the engineered T cells of any one of embodiments 19 to 23 to the patient with cancer, thereby treating cancer in the patient.

Embodiment 30

The method of embodiment 29, wherein the cancer is a B-cell malignancy.

Embodiment 31

The method of embodiment 30, wherein the B cell malignancy is selected from the group consisting of relapsed or refractory acute lymphoblastic leukemia (ALL), chronic lymphocytic leukemia (CLL), B-cell non-Hodgkin lymphoma (B-NHL), and large B-cell lymphoma.

Embodiment 32

The method of any one of embodiments 29 to 31, wherein administration comprises intravenous infusion, intra-arterial infusion, intraperitoneal infusion, direct injection into tumor and/or perfusion of tumor bed after surgery, implantation at a tumor site in an artificial scaffold, or intrathecal administration.

Embodiment 33

A polynucleotide encoding a target-binding molecule linked to a localizing domain, wherein the target-binding molecule comprises an antibody that binds a CD3/TCRαβ complex protein, and wherein the localizing domain comprises a retention signaling domain comprising an amino acid sequence selected from the group consisting of an endoplasmic reticulum (ER) retention sequence, a Golgi retention sequence, and a proteosome localizing sequence.

Embodiment 34

The polynucleotide of embodiment 33, wherein the CD3/TCRαβ complex protein is selected from the group consisting of TCRα, TCRβ, CD3ε, CD3δ, CD3γ, and CD3.

Embodiment 35

The polynucleotide of embodiment 33 or 34, wherein the antibody is a scFv.

Embodiment 36

The polynucleotide of embodiment 35, wherein said scFv comprises a variable heavy chain (VH) sequence having at least 95% sequence identity to SEQ ID NO:1 and a variable light chain (VL) sequence having at least 95% sequence identity to SEQ ID NO:2.

Embodiment 37

The polynucleotide of embodiment 35, wherein said scFv comprises a variable heavy chain (VH) sequence set forth in SEQ ID NO:1 and a variable light chain (VL) sequence set forth in SEQ ID NO:2.

Embodiment 38

The polynucleotide of any one of embodiments 33 to 37, wherein the localizing domain further comprises a transmembrane domain selected from a transmembrane domain derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B.

Embodiment 39

The polynucleotide of embodiments 38, wherein the transmembrane domain is a transmembrane derived from CD8α.

Embodiment 40

The polynucleotide of any one of embodiments 33 to 39, wherein the retention signaling domain comprises an amino acid sequence selected from KDEL (SEQ ID NO:32), KKMP (SEQ ID NO:33), KKTN (SEQ ID NO:43), or KKXX, wherein X is any amino acid (SEQ ID NO:35).

Embodiment 41

The polynucleotide of any one of embodiments 33 to 40, wherein the localizing domain comprises an amino acid sequence selected from any one in FIG. 8A or any one of SEQ ID NOS:11-31.

Embodiment 42

An expression vector comprising the polynucleotide of any one of embodiments 33 to 41.

Embodiment 43

The expression vector of embodiment 42, further comprising a polynucleotide encoding a chimeric antigen receptor.

Embodiment 44

The expression vector of embodiment 43, wherein the polynucleotide encoding the target-binding molecule linked to the localizing domain and the polynucleotide encoding the chimeric antigen receptor are bicistronic.

Embodiment 45

A host cell comprising the expression vectors of any one of embodiments 42 to 44.

Embodiment 46

Use of the substantially pure population of engineered T cells in embodiment 25 or 26 for treating cancer, comprising administering a therapeutically effective amount of the substantially pure population engineered T cells to a subject in need thereof.

Embodiment 47

The use of embodiment 46, wherein the cancer is a B cell malignancy.

Embodiment 48

The use of embodiment 47, wherein the B cell malignancy is selected from the group consisting of relapsed or refractory acute lymphoblastic leukemia (ALL), chronic lymphocytic leukemia (CLL), B-cell non-Hodgkin lymphoma (B-NHL), and large B-cell lymphoma.

Embodiment 49

The use of any one of embodiments 46 to 48, wherein the substantially pure population of engineered immune cells are administered into the subject by intravenous infusion, intra-arterial infusion, intraperitoneal infusion, direct injection into tumor and/or perfusion of tumor bed after surgery, implantation at a tumor site in an artificial scaffold, or intrathecal administration.

Embodiment 50

A method for producing an engineered CD3/TCRαβ-negative T cell, the method comprising: (i) introducing the polynucleotide encoding the target-binding domain linked to the localizing domain of any one of claims 33 to 41 into a T cell, and (ii) isolating the resulting CD3/TCRαβ-negative T cell.

Embodiment 51

The method of embodiment 50, wherein the T cell is an allogeneic T cell.

Embodiment 52

The method of embodiment 50 or 51, wherein the T cell is an engineered CD4+ T cell or an engineered CD8+ T cell.

Embodiment 53

The method of embodiment 50 or 51, wherein the engineered T cell is an engineered helper T cell or an engineered regulatory T cell.

Embodiment 54

The method of embodiment 50 or 51, wherein the engineered T cell is an engineered effector T cell or an engineered memory T cell.

Embodiment 55

The method of any one of embodiments 50 to 54, further comprising introducing a polynucleotide encoding a chimeric antigen receptor (CAR) into the T cell.

Embodiment 56

The method of embodiment 55, wherein the polynucleotide encoding the target-binding domain linked to the localizing domain and the polynucleotide encoding a chimeric antigen receptor is operatively linked to the nucleic acid encoding the CAR are bicistronic.

Embodiment 57

An engineered CD3/TCRαβ-negative chimeric antigen receptor T (CAR-T) cell comprising: (i) a chimeric antigen receptor (CAR), and (ii) a target-binding molecule linked to a localizing domain, wherein the target-binding molecule comprises an antibody that binds a CD3/TCRαβ complex protein, wherein the localizing domain comprises a retention signaling domain comprising an amino acid sequence selected from the group consisting of an endoplasmic reticulum (ER) retention sequence, a Golgi retention sequence, and a proteosome localizing sequence, and wherein the target-binding molecule linked to the localizing domain is not secreted by the engineered CAR-T cell.

Embodiment 58

The engineered CAR-T cell of embodiment 57, wherein the CD3/TCRαβ complex protein is selected from the group consisting of TCRα, TCRβ, CD3ε, CD3δ, CD3γ, and CD3ζ.

Embodiment 59

The engineered CAR-T cell of embodiment 57 or 58, wherein the antibody is a single chain variable fragment (scFv).

Embodiment 60

The engineered CAR-T cell of embodiment 59, wherein the scFv comprises a variable heavy chain (VH) sequence having at least 95% sequence identity to SEQ ID NO:1 and a variable light chain (VL) sequence having at least 95% sequence identity to SEQ ID NO:2.

Embodiment 61

The engineered CAR-T cell of embodiment 59, wherein the scFv comprises a variable heavy chain (VH) sequence set forth in SEQ ID NO:1 and a variable light chain (VL) sequence set forth in SEQ ID NO:2.

Embodiment 62

The engineered CAR-T cell of any one of embodiments 57 to 61, wherein the engineered CAR-T cell is an engineered CD4+ T cell or an engineered CD8+ T cell.

Embodiment 63

The engineered CAR-T cell of any one of embodiments 57 to 61, wherein the engineered CAR-T T cell is an engineered helper T cell or an engineered regulatory T cell.

Embodiment 64

The engineered CAR-T cell of any one of embodiments 57 to 61, wherein the engineered CAR-T cell is an engineered effector T cell or an engineered memory T cell.

Embodiment 65

The engineered CAR-T cell of any one of embodiments 57 to 64, wherein the engineered CAR-T cell is an autologous T cell.

Embodiment 66

The engineered CAR-T cell of any one of embodiments 57 to 64, wherein the engineered CAR-T cell is an allogeneic T cell.

Embodiment 67

The engineered CAR-T cell of any one of embodiments 57 to 66, wherein the localizing domain further comprises a transmembrane domain selected from a transmembrane domain derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B.

Embodiment 68

The engineered CAR-T cell of embodiment 67, wherein the transmembrane domain is the transmembrane domain derived from CD8α.

Embodiment 69

The engineered CAR-T cell of any one of embodiments 57 to 68, wherein the ER retention sequence comprises an amino acid sequence selected from KDEL (SEQ ID NO:32), KKMP (SEQ ID NO:33), KKTN (SEQ ID NO:43), or KKXX, wherein X is any amino acid (SEQ ID NO:35).

Embodiment 70

The engineered CAR-T cell of any one of embodiments 57 to 69, wherein the localizing domain comprises an amino acid sequence selected from any one in FIG. 8A or any one of SEQ ID NOS:11-31.

Embodiment 71

The engineered CAR-T cell of any one of embodiments 57 to 70, wherein the CAR binds to CD3 or CD19.

Embodiment 72

The engineered CAR-T cell of embodiment 71, wherein the CAR comprises an anti-CD3 scFv domain, a 4-1BB stimulatory signaling domain, and a CD3t signaling domain.

Embodiment 73

The engineered CAR-T cell of embodiment 71, wherein the CAR comprises an anti-CD19 scFv domain, a 4-1BB stimulatory signaling domain, and a CD3t signaling domain.

EXAMPLES

Example 1: A Novel Method to Generate T Cell Receptor-Deficient Chimeric Antigen Receptor T Cells Abstract Practical methods to improve chimeric antigen receptor (CAR)-T cell therapies are needed to broaden their applicability. The use of allogeneic, instead of autologous, CAR-T cells is attractive, but endogenous T-cell receptors (TCRs) must be knocked-down to reduce risk of graft-versus-host-disease (GVHD). To remove surface TCRαβ, we combined an antibody-derived single chain variable fragment (scFv) specific for CD3ε with 21 different amino acid sequences predicted to mediate to retain it intracellularly. After transduction in Jurkat cells and peripheral blood T cells, several of these Protein Expression Blockers (PEBLs) co-localized intracellularly with CD3, blocking surface CD3 and TCRαβ expression. In 25 experiments, median TCRαβ expression in T lymphocytes was reduced from 95.7% to 25.0%; CD3/TCRαβ cell depletion yielded virtually pure TCRαβ-negative T cells. Anti-CD3ε PEBLs abrogated TCRαβ-mediated signaling, without affecting immunophenotype or proliferation. In anti-CD3ε PEBL-T cells expression of an anti-CD19-41BB-CD3ζ CAR induced cytokine secretion, long-term proliferation and CD19+ leukemia cell killing, at rates meeting or exceeding those of CAR-T cells with normal CD3/TCRαβ expression. In immunodeficient mice, anti-CD3ε PEBL T cells had markedly reduced GVHD potential; when transduced with anti-CD19 CAR, these T cells engrafted leukemic cells. PEBL blockade of surface CD3/TCRαβ expression is an effective tool to prepare allogeneic CAR-T cells. Combined PEBL and CAR expression can be achieved in a single-step procedure, is easily adaptable to current cell manufacturing protocols, and can be used to target other T-cell molecules to enhance CAR-T cell therapies.

Introduction

Genetically-engineered immune cells are a powerful new treatment for cancer. Results of recent clinical trials with T lymphocytes expressing chimeric antigen receptors (CARs) have provided compelling demonstration of the power of this approach. Thus, CAR-T cells specific for the surface molecule CD19 induced morphologic and molecular remissions in patients with treatment-refractory CD19-positive malignancies, such as acute lymphoblastic leukemia (ALL), chronic lymphocytic leukemia and non-Hodgkin lymphoma.[1-10] Other malignancies can be attacked by T cells redirected against different antigens. Hence, the possible applications for genetically-engineered cellular therapy in oncology are wide-ranging.[10,11]

The initial clinical experience with CAR-T cells has also identified limitations that could diminish therapeutic effect and hamper development. A major issue is the variable fitness of immune cells collected from patients with cancer, resulting in an unpredictable capacity to expand in vivo and exert antitumor effects.[10,12] This variability complicates the identification of the most effective cell dosages and might lead to infusion of short-lived and ineffective cells. T lymphocytes from healthy donors should offer better consistency and effectiveness, but pose the risk for graft-versus-host disease (GVHD), a potentially fatal consequence of donor lymphocyte infusion.[13,14] In such an allogeneic setting, additional modifications to the infused T cells are required to suppress their capacity to recognize host tissues; namely, downregulation of CD3/TCRαβ.[15,16]

Contemporary methodologies for gene editing have opened new opportunities relevant to cell therapy of cancer.[17] Zinc finger meganucleases, TALEN, and CRISPR-Cas9 can delete genes encoding TCRαβ chains, leading to T cells that lack alloreactivity,[15,18,19] whereas other genes can be targeted to delay rejection.[15] A report using TALEN deletion of the TCRα and CD52 loci together with anti-CD19 CAR expression indicates that combining CAR expression with gene editing is feasible in a clinical setting,[20] although it may still be technically challenging.

To expand the arsenal of tools for enhancing cell-based therapies of cancer, we developed a method which allows simple and effective blockade of surface receptor expression in immune cells. Specific constructs, named Protein Expression Blockers (PEBLs), prevent transport of targeted proteins to the cell membrane. PEBL constructs can be readily combined with other gene modifications and be incorporated into existing clinical-grade protocols for ex vivo cell processing to optimize the function of immune cells. We tested the potential of this approach to downregulate CD3/TCRαβ expression in CAR-T cells.

Materials and Methods

Tumor Cell Lines and T Cells

Kurkat, Loucy, Nalm6, RS4; 11, and K562 were from the American Type Culture Collection (Rockville, Md.); OP-1 was established in our laboratory.[21] A murine stem cell virus (MSCV) retroviral vector was used to express the firefly luciferase gene plus green fluorescent protein (GFP) in Nalm6, and CD19 plus DsRed in K562.[22]

Peripheral blood from healthy donors was obtained from anonymized byproducts of platelet donations at the National University Hospital Blood Bank, Singapore, with Institutional Review Board (National University of Singapore) approval in accordance with the Declaration of Helsinki. Mononucleated cells were separated by centrifugation on Lymphoprep (Axis-Shield, Oslo, Norway). T cells, enriched with Dynabeads Human T-Activator CD3/CD28 (Thermo Fisher Scientific, Waltham, Mass.), were cultured in RPMI-1640 (Thermo Fisher), 10% fetal bovine serum (GE-Healthcare, Chicago, Ill.), and antibiotics, with interleukin 2 (IL-2; Proleukin, Novartis, Basel, Switzerland; 100 IU/mL) added every 2 days.

PEBL Constructs

From RNA of the PLU4 murine hybridoma, secreting an anti-human CD3 monoclonal antibody (immunoglobulin G2a [IgG2a] isotype; Creative Diagnostics, Shirley, NY), we synthesized cDNA by Moloney Murine Leukemia Virus reverse transcriptase and Oligo(dT)15 primer (Promega, Madison, Wis.). We amplified variable regions of heavy and light chain with IgG Library Primer Set Mouse BioGenomics (US Biological, Salem, Mass.) and assembled them into a single-chain variable fragment (scFv) by a flexible linker sequence encoding $(Gly_4Ser)_4$. CD8α signal peptide and transmembrane domains were from human-activated T-cell cDNA.

To generate PEBL constructs, each retention-signaling domain (FIG. 8A) was added to the 3' end of the variable heavy chain fragment by PCR. Constructs were subcloned into the MSCV retroviral vector containing an internal ribosome entry site and GFP or mCherry. Preparation of retroviral supernatant and gene transduction were performed as previously described.[23] Briefly, retroviral vector-conditioned medium was added to polypropylene tubes coated with RetroNectin (Takara, Otsu, Japan); after removing the supernatant, activated T cells were added and left at 37° C. for 12 hours; fresh viral supernatant was added on 2 other successive days. T lymphocytes were maintained in RPMI-1640 with fetal bovine serum, antibiotics, and 200 IU/mL IL-2 until the time of the experiments.

To remove residual CD3/TCRαβ-positive T cells after PEBL transduction, we used allophycocyanin (APC)-conjugated anti-CD3 (BD Biosciences, San Jose, Calif.; or Miltenyi Biotec, Bergisch Gladbach, Germany) and anti-TCRαβ antibodies (BioLegend, San Diego, Calif.), with anti-APC MicroBeads and LD column (Miltenyi Biotec).

A CAR constituted by an anti-CD19 scFv, CD8α hinge and transmembrane domains, and cytoplasmic domains of 41BB and CD3ζ (anti-CD19-41BB-CD3ζ)[22] was inserted in the MSCV vector, as described for PEBLs. In some experiments, CAR-T cells were expanded by coculture with 100 Gy-irradiated K562 cells transduced with CD19, at a 1:1 E:T ratio. We also transduced T cells with a MSCV vector containing both CAR and PEBL constructs separated by a sequence encoding a self-cleaving 2A peptide.[24] Electroporation of anti-CD19-41BB-CD3 mRNA was performed as previously described.[25,26] Cells electroporated without mRNA were used as control.

Determination of scFv Specificity, PEBL and CAR Expression, and Cell Marker Profile To identify the CD3 subunit bound to the antibody derived from the PLU4 hybridoma, the cDNA of each CD3 subunit (Origene, Rockville, Md.) was subcloned into MSCV-internal ribosome entry site-GFP and transduced into K562 cells. K562 cells were then permeabilized with 8E reagent (a permeabilization reagent developed by the inventors), incubated with supernatant from PLU4 hybridoma cells, followed by Alexa Fluor 647 conjugated goat anti-mouse IgG (Southern Biotech, Birmingham, Ala.).

CAR and PEBL expression was detected by biotin-conjugated goat anti-mouse IgG F(ab')2 antibody (Jackson ImmunoResearch, West Grove, Pa.), and phycoerythrin (PE)- or APC-conjugated streptavidin (Jackson ImmunoResearch). For intracellular staining, cells were permeabilized with 8E. To determine whether PEBLs were secreted, supernatant from anti-CD3 scFv- or PEBL-transduced Jurkat was added to Loucy and incubated in 4° C. for 45 minutes; surface-bound scFv and PEBLs were detected with biotin-conjugated goat anti-mouse IgG F(ab')2 antibody and streptavidin APC.

CD3 expression was detected with anti-CD3 APC (SK7, BD Biosciences). PE- or APC-conjugated anti-TCRαβ (IP26), CD2 APC (RPA-2.10), CD137 APC (4B4-1), CD279 PE (EH12.2H7), and CD3δ6 PE (F38-2E2) were from BioLegend (San Diego, Calif.). Anti-CD4 PE-Cy7 (SK3), CD8 PE (RPA-T8), CD7 PE (M-T701), CD25 PE-Cy7 or APC (2A3), CD62L APC (DREG-56), and CD69 PE or APC (L78) were from BD Biosciences; CD223 APC (3DS223H) was from Thermo Fisher. Cell staining was analyzed using Fortessa or Accuri C6 flow cytometers (BD Biosciences).

T-Cell Activation, Cytokine Production, Proliferation, and Cytoxicity

OKT3 (10 μg/mL, Miltenyi Biotech) or isotype-matched control (R&D, Minneapolis, Minn.) was dispensed into 96-well flat-bottom plates (Corning, Corning, N.Y.) and left at 4° C. for 12 hours. After removing soluble antibody, 1 to $2 \times 10^5$ Jurkat cells per well were seeded and cultured at 37° C., 5% $CO_2$ for 24 hours. PE- or APC-conjugated anti-CD25 and anti-CD69 antibodies were used to determine T-cell activation, with isotype-matched nonreactive antibodies as control (all from BD Biosciences).

Jurkat cells were transduced with a TCR specific for the hepatitis B virus (HBV) s183 peptide in the context of HLA-A2 (provided by A. Bertoletti, Duke-NUS, Singapore).[27] The TCR was inserted into a MSCV vector containing a neomycin-resistant gene, and transduced cells were selected by exposure to neomycin. Expression of TCRβ on the cell surface and intracellularly (after cell permeabilization with 8E) was detected with an anti-TCR Vβ3 antibody conjugated to fluorescein isothiocyanate (Beckman Coulter, Brea, Calif.). HBV s183-Jurkat cells, transduced with an mCherry vector with or without anti-CD3 PEBL, were cocultured with T2 cells (also from A. Bertoletti) pulsed with 1 μg/mL HBV s183 peptide (Genscript, Piscataway, N.J.) at a 1:1 E:T ratio. After 24 hours, cells were stained with anti-CD25 PE and anti-CD69 APC.

To measure interferon γ (IFNγ) production, $1 \times 10^5$ T cells and $2 \times 10^5$ RS4; 11 cells were seeded in a 96-well round bottom plate. After 8 hours in the presence of 0.1% Brefeldin A (GolgiPlug, BD Biosciences), cells were labeled with APC- or PE-conjugated anti-IFNγ (clone 25723.11, BD Biosciences) after cell membrane permeabilization.

To measure cell proliferation, $5 \times 10^4$ T cells transduced with CAR or GFP only were placed in 96-well round bottom plate in RPMI-1640 with 10% fetal bovine serum, antibiotics, and 200 IU/mL of IL-2. OP-1 cells were irradiated (100 Gy) and mixed with the T cells at 1:1 E:T. Every 2 days, 200 IU/mL of IL2 was added. GFP+ cells were counted by flow cytometry; a new set of irradiated OP-1 cells was added at 1:1 E:T every 7 days.[23]

To test cytotoxicity, target cells were labeled with calcein red-orange AM (Thermo Fisher) and plated into a 96-well round bottom plate at a concentration of $5 \times 10^4$ cells per 100 μL. cells were added at various E:T ratios and cultured at 37° C., 5% $CO_2$. After 4 hours, the number of viable target cells was counted by flow cytometry. In some tests, luciferase-labeled cells were used as a target. The assay was performed in a 96-well flat bottom plate, BrightGlo (Promega) was added to the wells after 4 hours, and luminescence was measured using a Flx 800 plate reader (BioTek, Winooski, Vt.).[23]

Mouse Models

To model GVHD, NOD.Cg-Prkdc$^{scid}$ IL2rg$^{tm1Wjl}$/SzJ (NSG) mice (Jackson Laboratory, Bar Harbor, Me.) received 2.5 Gy total body irradiation. One day later, $1 \times 10^7$ T cells transduced with either anti-CD3 PEBL plus GFP or GFP alone were IV infused. All mice received IL-2 (20 000 IU)

3 times per week intraperitoneally (IP). Body weight and GVHD symptoms were monitored 3 times per week; blood was collected once a week by cheek prick. Mice were euthanized when body weight reduction exceeded 20% of the baseline in 2 consecutive measurements. Histopathology evaluation for GVHD was performed at the Advanced Molecular Pathology Laboratory, Institute of Molecular and Cell Biology (Singapore). Anti-human CD3 polyclonal antibody (Agilent Technologies, Santa Clara, Calif.), anti-human CD4 (EPR6855), and anti-human CD8 (EP1150Y; both from Abcam, Cambridge, United Kingdom) were used for immunohistochemistry.

For the acute lymphoblastic leukemia (ALL) model, Nalm6 cells expressing luciferase ($0.5 \times 10^6$ cells per mouse) were IV injected, followed 3 days later by T cells transduced with anti-CD19-41BB-CD3ζ and either anti-CD3 PEBL or mCherry ($2 \times 10^7$ per mouse IV); control mice received RPMI-1640 medium. In a second experiment, mice received 2.5 Gy total body irradiation on day 3 before infusion of T cells or RPMI-1640. All mice received IL-2 (20 000 IU) 3 times per week IP. Leukemia cell load was determined with the Xenogen IVIS-200 System (Perkin Elmer, Waltham, Mass.) after injecting 150m/g body weight of aqueous d-luciferin potassium salt (Perkin Elmer) IP. Luminescence was analyzed with Living Image 3.0 software. Mice were euthanized when the luminescence reached $1 \times 10^{10}$ photons per second, or earlier if body weight reduction exceeded 20% of their baseline in 2 consecutive measurement or there were other physical signs warranting euthanasia.

Results

Design and Functional Screening of PEBL Constructs

Figure 9:
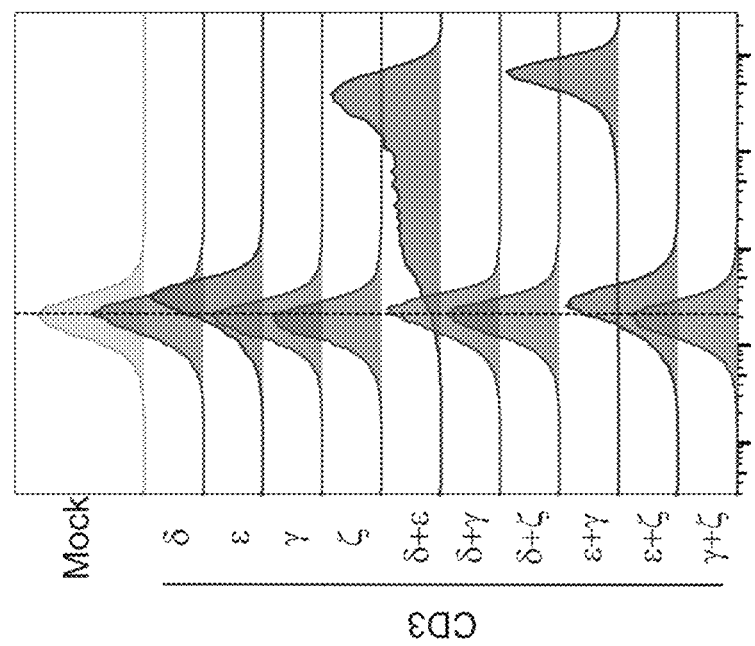
FIG. 9. Specificity of anti-CD3 antibody used to derive the scFv for the PEBLs. K562 cells were transduced with cDNA of each CD3 subunit (δ, ε, γ, ζ), combinations of 2 subunits, or a vector containing GFP only ("Control"). Transduced cells were permeabilized and incubated with the supernatant secreted from PLU4 hybridoma cells, and then stained with Alexa Fluor 647 conjugated goat anti-mouse IgG antibody (SouthernBiotech, Birmingham, Ala.). Analysis was performed with a Fortessa flow cytometer (BD Bioscience) and FlowJo software.

The CD3/TCRαβ complex is assembled in the endoplasmic reticulum (ER); all components are required for its cell surface expression. To determine the CD3 specificity of the PLU4 antibody, we transduced K562 cells with CD3ε, CD3γ, CD3δ, and CD3t alone or in combination and tested PLU4 reactivity by flow cytometry (FIG. 9). The staining pattern indicated reactivity with an epitope of CD3ε most accessible when associated with either CD3γ or CD3δ.

We generated an scFv from the PLU4 hybridoma cDNA and linked it to sequences encoding peptides predicted to anchor it to the ER and/or the Golgi apparatus (FIG. 8A). We tested 21 constructs for their capacity to suppress CD3 surface expression and compared them with a construct containing SEKDEL (SEQ ID NO:50), a sequence reported to suppress expression of surface proteins when linked to an scFv.[31] In Jurkat cells, retroviral transduction of many of the PEBLs caused a nearly complete elimination of surface CD3 expression (FIGS. 1A-1B), whereas most cells transduced with the SEKDEL construct remained CD3-positive.

Figure 10C:
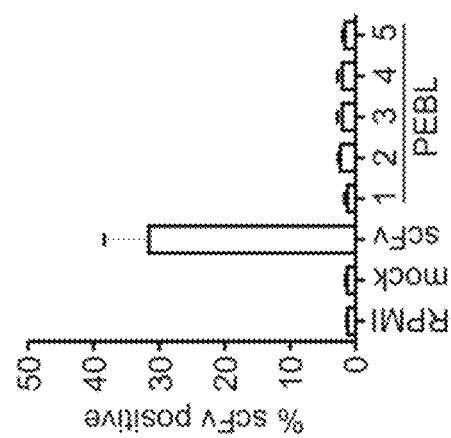
FIG. 10A-FIG. 10C. Cellular localization of anti-CD3ε PEBL.
Figure 10B:
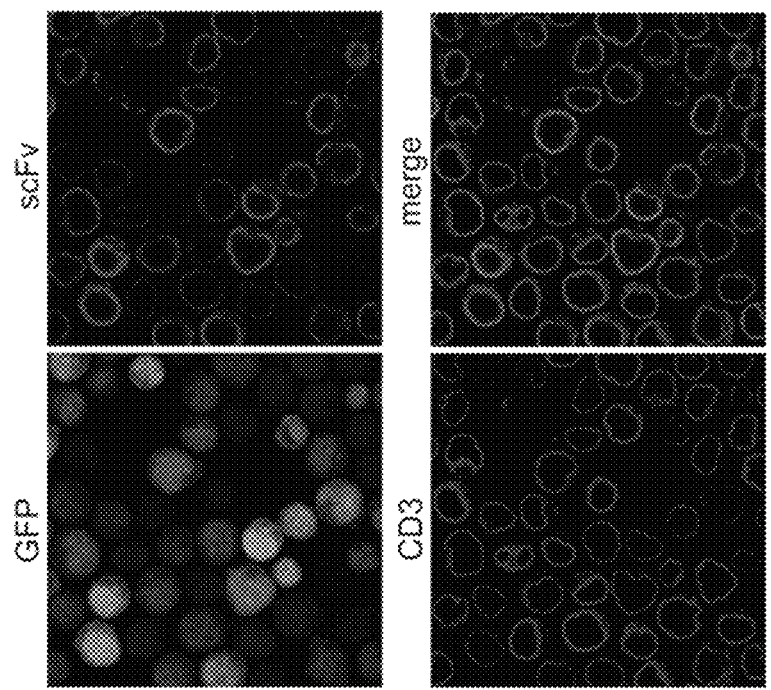
Figure 10A:
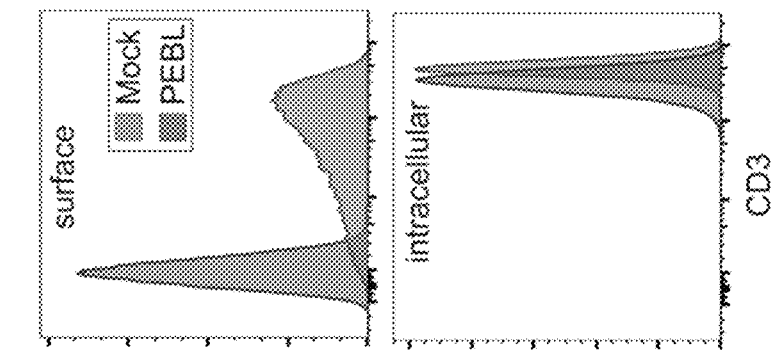

Expression of PEBLs 1-8, 11, and 19 was confined intracellularly; other PEBLs had varying degrees of surface expression (FIG. 1C, FIGS. 10A-10C). PEBLs colocalized with C3 intracellularly; no secretion was detected in tests with PEBLs 1-5 (FIGS. 10A-10C). Importantly, PEBLs also effectively downregulated CD3 expression in activated peripheral blood T lymphocytes (FIG. 1D).

CD3 Downregulation with PEBLs Suppresses TCRαβ Expression

In addition to CD3, PEBL transduction also downregulated TCRαβ expression in peripheral blood T lymphocytes. In 25 experiments, median percentage of T cells expressing TCRαβ was reduced from 95.7% (range, 89.4% to 99.0%) to 25.0% (range, 3.5% to 55.2%; FIG. 2A). The main factor determining the extent of CD3/TCRαβ downregulation was the efficiency of retroviral transduction, which ranged between 58.5% and 99.8% (median GFP+ cells, 94.2%).

Magnetic removal of residual CD3/TCRαβ-positive cells yielded virtually pure populations of CD3/TCRαβ-negative T cells (FIG. 2B); in 11 T-cell preparations from 6 donors, T cells expressing normal levels of CD3/TCRαβ were 0.01% (<0.01% to 0.15%) after only 1 round of CD3/TCRαβ depletion.

Figure 2C:
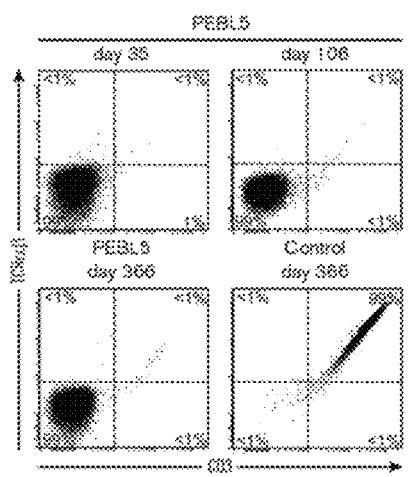
Figure 2D:
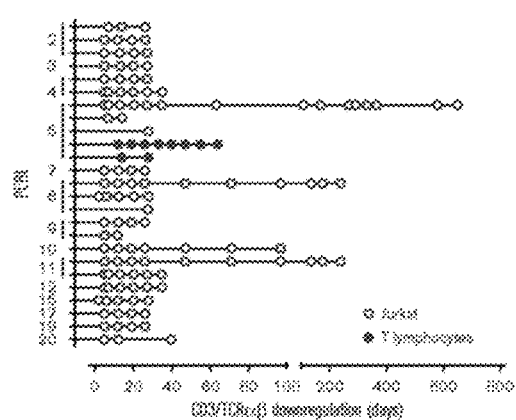
Figure 11:
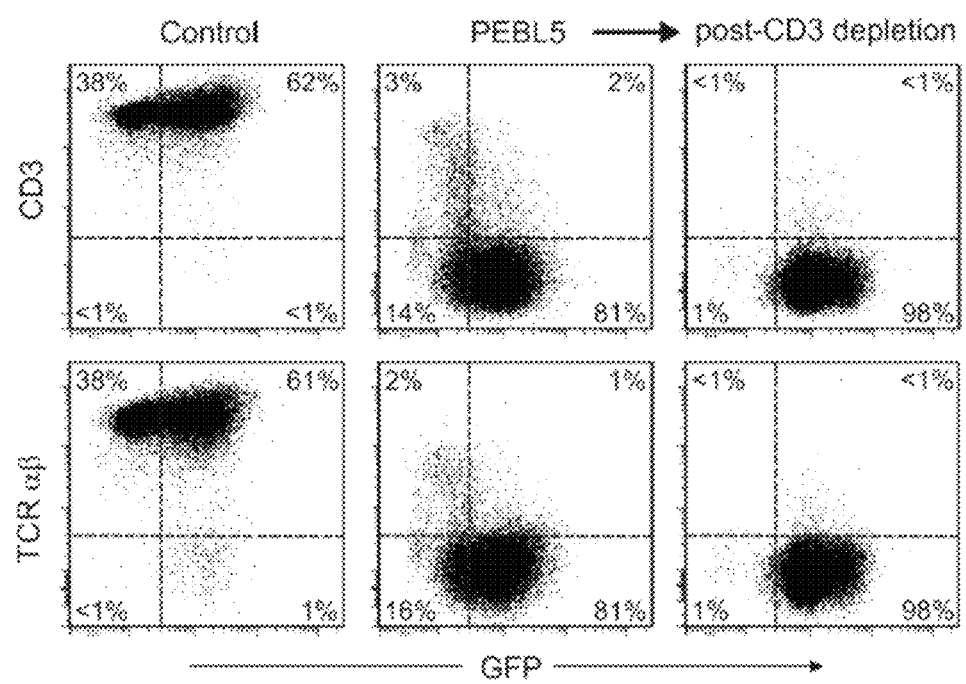
FIG. 11. Downregulation of CD3/TCRαβ in T lymphocytes after long-term culture. Flow cytometric dot-plots illustrate CD3 and TCRαβ expression in T lymphocytes transduced with PEBL5 plus GFP, or GFP alone ("Control"), after 55 days of culture with 200 IU/mL IL-2. Results before and after depletion of residual CD3+ cells are shown.
Figure 12A:
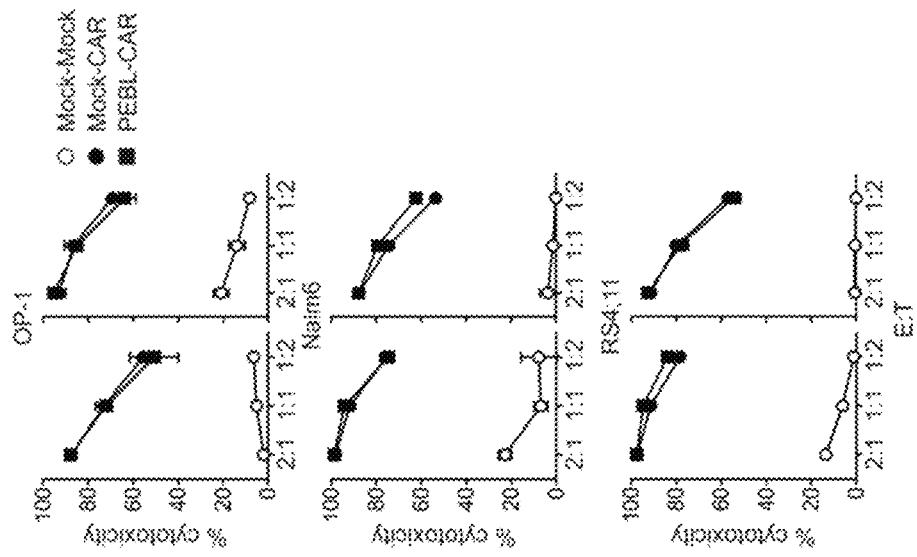
FIG. 12A-FIG. 12B. Cytotoxicity of PEBL-CAR T lymphocytes.
Figure 12B:
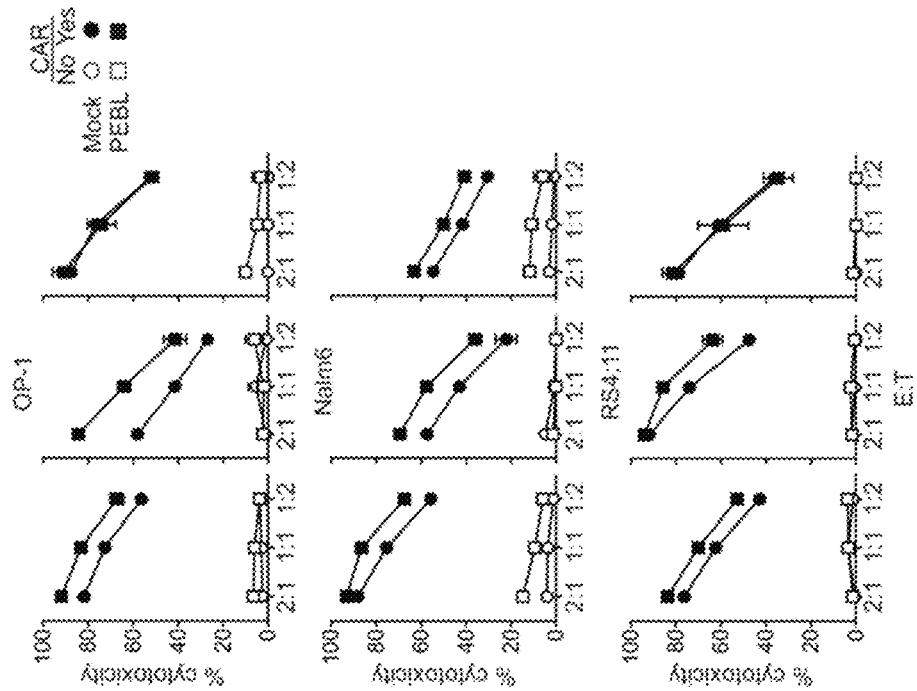

In peripheral blood T lymphocytes and Jurkat cells maintained in continuous culture, CD3/TCRαβ downregulation was persistent, with a follow-up of up to 2 months for T lymphocytes and 21 months for Jurkat cells (FIGS. 2C-2D; FIG. 11).

Function of T Cells with Downregulated CD3/TCRαβ by PEBL

In addition to the lack of surface CD3/TCRαβ, there was no noticeable phenotypic change in lymphocytes transduced with PEBLs; expression of CD4, CD8, CD2, CD7, CD25, CD62L, CD69, CD137 (4-1BB), CD223 (LAG3), CD279 (PD-1), and CD3δ6 (TIM-3) was not significantly altered (FIG. 8B). T-cell proliferation was also unaffected. In experiments with Jurkat cells, the proliferative rate of PEBL-transduced cells was identical to that of cells transduced with GFP alone (FIG. 3A). Likewise, expansion and survival of peripheral blood T cells with IL-2 (200 IU/mL) were not affected by PEBL transduction and CD3/TCRαβ downregulation (FIG. 3B).

Figure 3F:
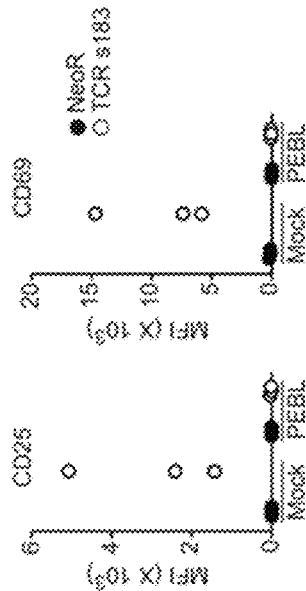
Figure 3E:
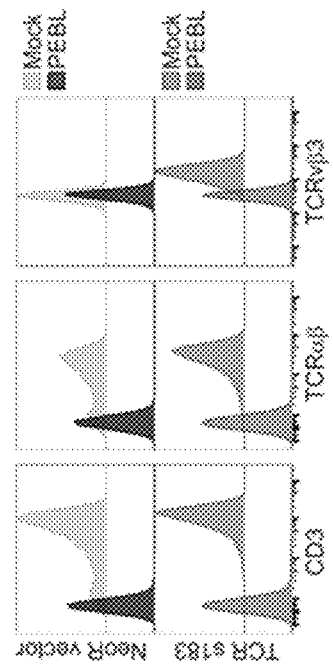

As expected, knock-down of surface CD3 abrogated CD3 signaling. Thus, in Jurkat cells cultured with the anti-CD3 antibody OKT3, the activation markers CD25 and CD69 were not upregulated if cells had been transduced with anti-CD3 PEBL (FIG. 3C). Moreover, if peripheral blood T cells were cultured with OKT3 for 48 hours, viability of cells transduced with GFP alone rapidly decreased, whereas numbers of PEBL-transduced cells remained high (FIG. 3D). Finally, we transduced Jurkat cells with a TCR against the HBV s183 peptide expressed in the context of HLA-A2.27 Anti-CD3c PEBL transduction blocked the surface expression of CD3, of anti-HBV TCRαβ, and of its TCRVβ3 chain (FIG. 3E); it abrogated the cells' capacity to respond to HLA-A2-expressing cells (T2) pulsed with the HBV s183 peptide (FIG. 3F).

Function of Anti-CD19 CAR in T Cells Transduced with Anti-CDR PEBL

PEBL transduction did not affect T-cell immunophenotype and proliferation, suggesting that expression of a CAR in PEBL-T cells might induce target-specific cytotoxicity, as well as in CD3/TCRαβ-positive T cells. To test this notion, we expressed the anti-CD19-41BB-CD3ζ CAR and anti-CD3 PEBL in T cells and compared their function with that of CAR-T cells without PEBL. In 9 paired experiments, CAR expression by either viral transduction (n=4) or mRNA electroporation (n=5) was high, regardless of CD3/TCRαβ expression (FIGS. 4A-4B). Neither PEBL expression nor CD3/TCRαβ downregulation affected CAR function, including CAR-mediated IFNγ secretion and T-cell proliferation (FIGS. 4C-4D).

Figure 5A:
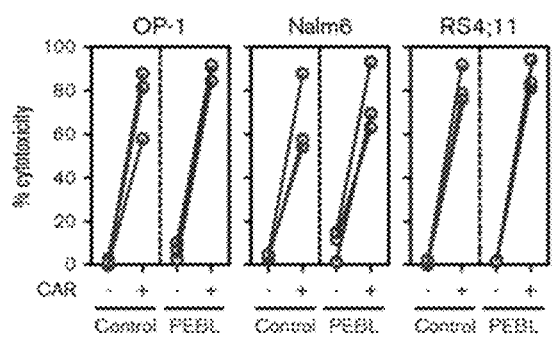
FIG. 5A-FIG. 5D. Cytotoxicity of CAR+PEBL T lymphocytes.
Figure 5B:
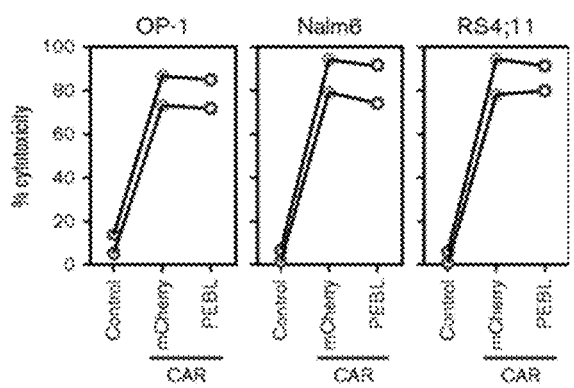
Figure 5C:
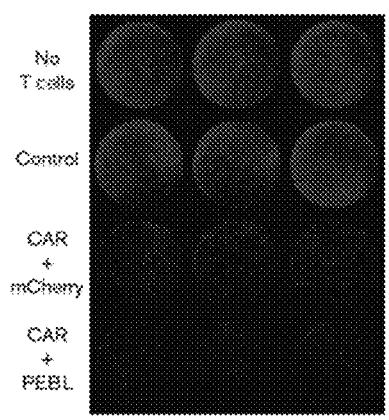
Figure 5D:
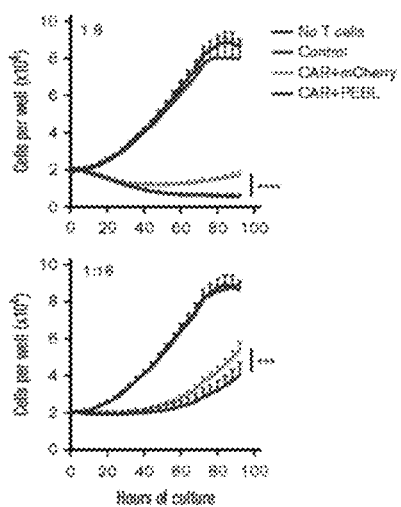

CAR expression in PEBL-transduced T cells induced strong cytotoxicity against CD19+ leukemia cell targets, regardless of whether the CAR was expressed by mRNA electroporation or viral transduction (FIGS. 5A-5B, FIGS. 12a-12B). We also determined CAR cytotoxicity at low E:T ratios over longer periods, using a live-cell imaging system. CAR+PEBL-T cells were at least as effective as CAR-T cells without PEBL at exerting antileukemic cell killing, with higher cytotoxicities seen at 1:8 and 1:16 E:T (FIG. 5C-5D).

Figure 13B:
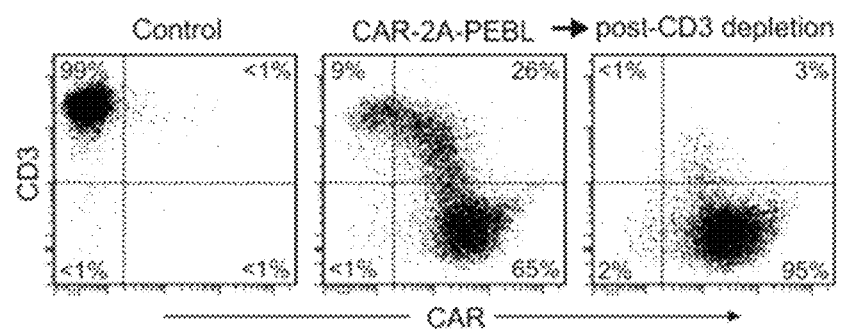
Figure 13C:
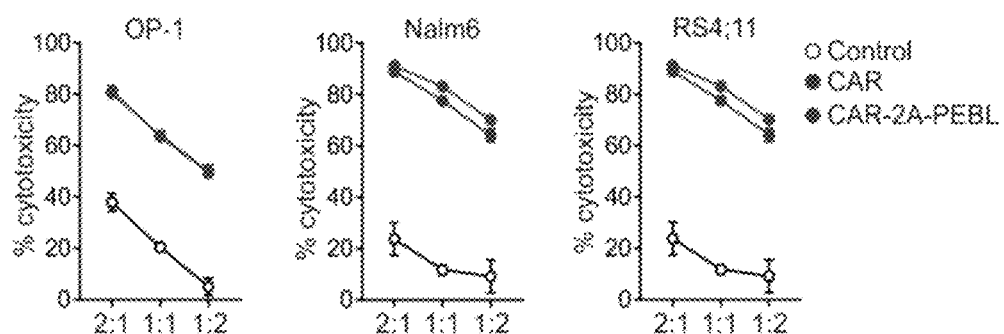

Downregulation of CD3 with CAR expression and function could also be effectively achieved by using a bicistronic vector containing both CAR and PEBL (FIGS. 13A-13C).[24]

Xenoreactivity and Antileukemic Potency of PEBL-T Cells in Immunodeficient Mice

Figure 6B:
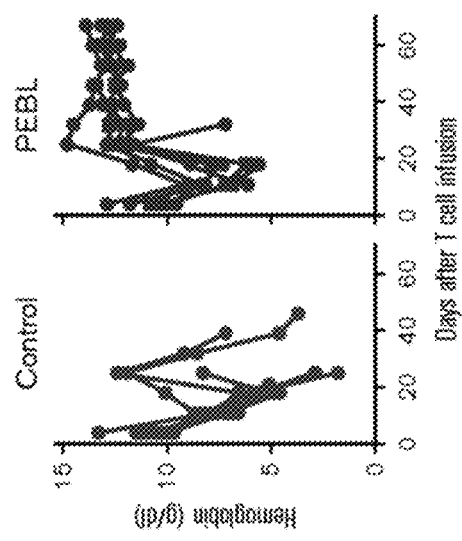
FIG. 6A-FIG. 6E. CD3/TCRαβ knock-down by PEBL prevents GVHD.
Figure 6A:
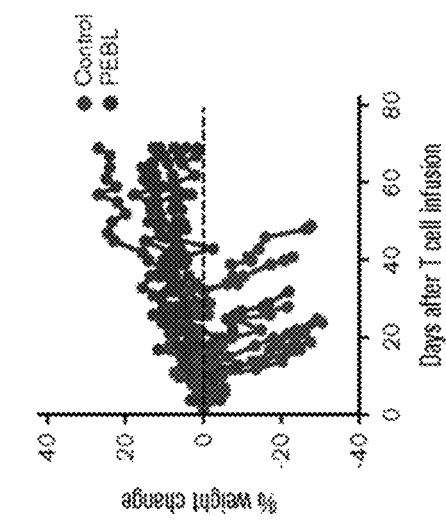
Figure 6E:
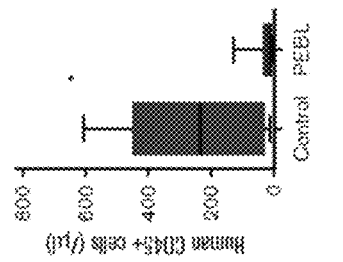
Figure 6D:
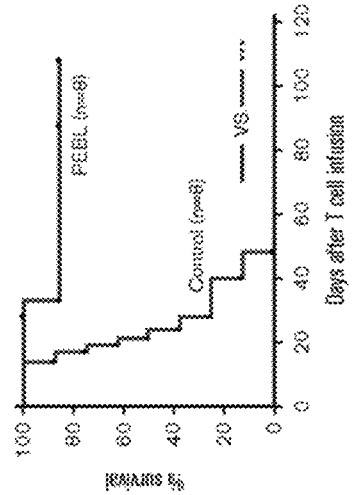
Figure 6C:
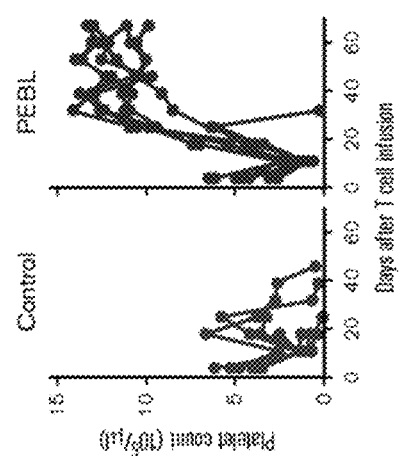
Figure 14A:
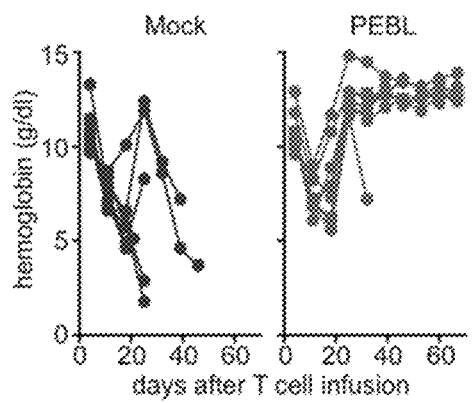
FIG. 14A-FIG. 14C. Signs of GvHD in mice receiving human T lymphocytes without PEBL downregulation of CD3/TCRαβ expression. NOD-SCID-IL2RGnull mice were irradiated with 2.5 Gy, and then i.v. injected 1 day later with 1×10⁷ T lymphocytes transduced with either anti-CD3 PEBL or GFP only ("Mock"; n=8 in each group). All mice received IL-2 (20000 IU) 3 times/week i.p.
Figure 14B:
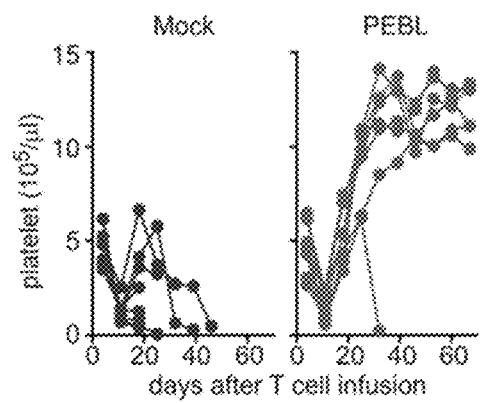
Figure 14C:
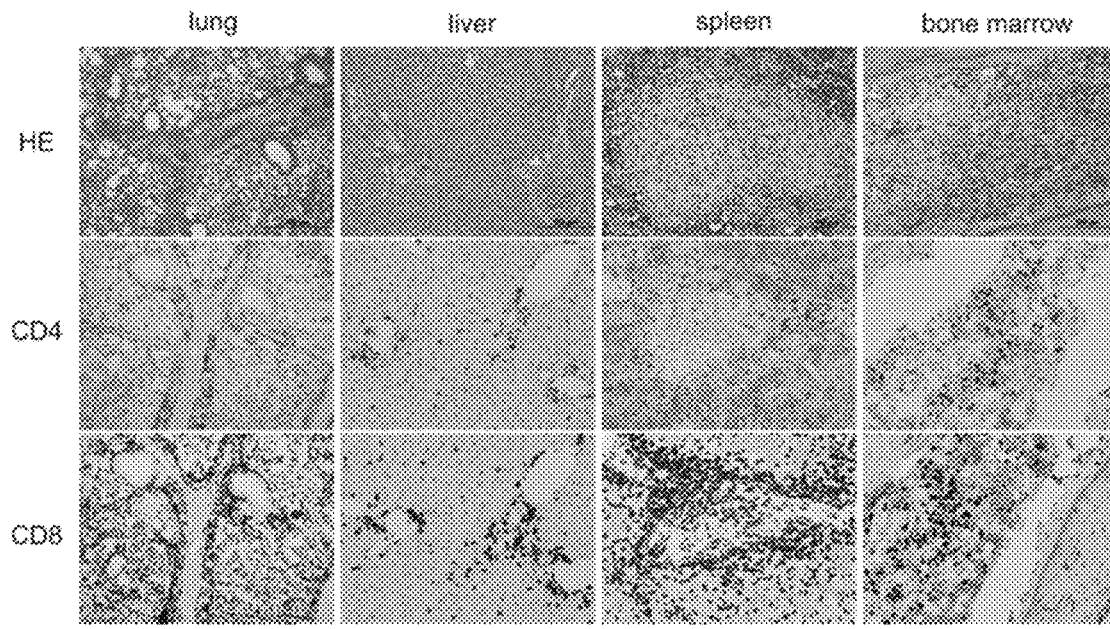
Figure 15:
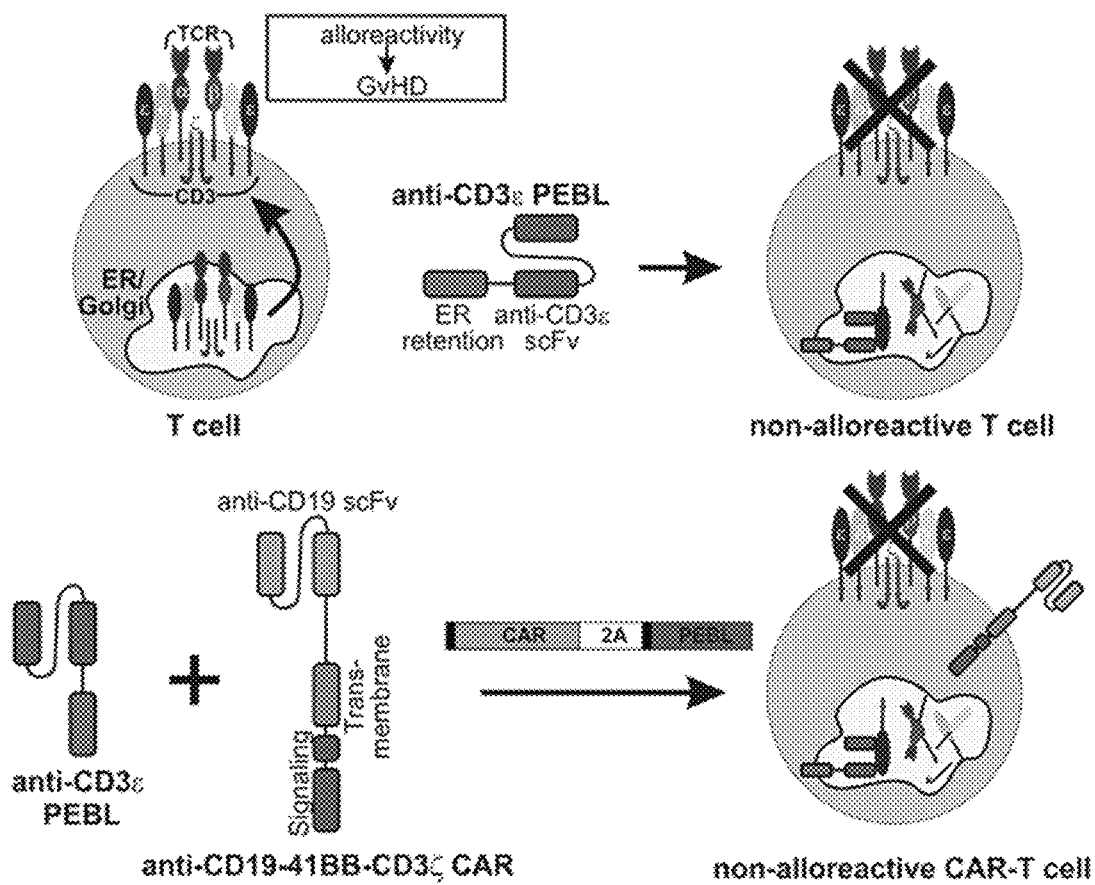
FIG. 15. Schematic diagram of a non-alloreactive T cell expressing an anti-CD3c PEBL and a non-alloreactive CAR-T cell expressing an anti-CD3ε PEBL and a CAR from a bicistronic construct.

To further test the effectiveness of CD3/TCRαβ knockout by PEBL, we infused anti-CD3 PEBL T cells in NSG mice that had received 2.5 Gy radiation and evaluated the T cells' capacity to cause GVHD. All 8 mice injected with human T cells transduced with GFP alone exhibited weight loss, anemia, and thrombocytopenia, whereas these GVHD signs were seen in only 1 of the 8 mice injected with PEBL-transduced T cells (FIGS. 6A-6D; P=0.0003 in log-rank test of survival). Human T-cell numbers measured in their peripheral blood were markedly higher overall in mice injected with GFP-transduced T cells (FIG. 6E), suggesting that PEBL suppressed T-cell stimulation by xenoantigens. The occurrence of GVHD was confirmed by pathological findings (FIG. 14C and FIG. 8C).

Figure 7A:
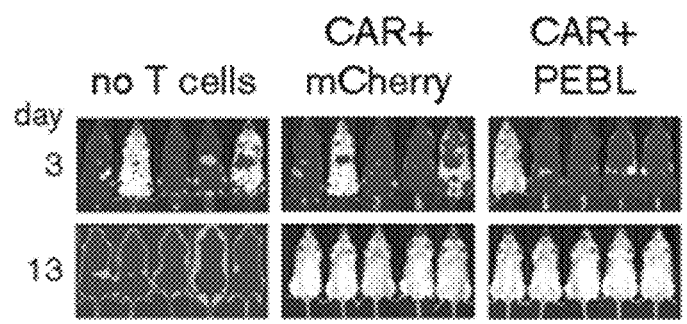
FIG. 7A-FIG. 7F. T cells with CD3/TCRαβ knock-down by PEBL and CAR expression kill leukemia cells in mice.
Figure 7B:
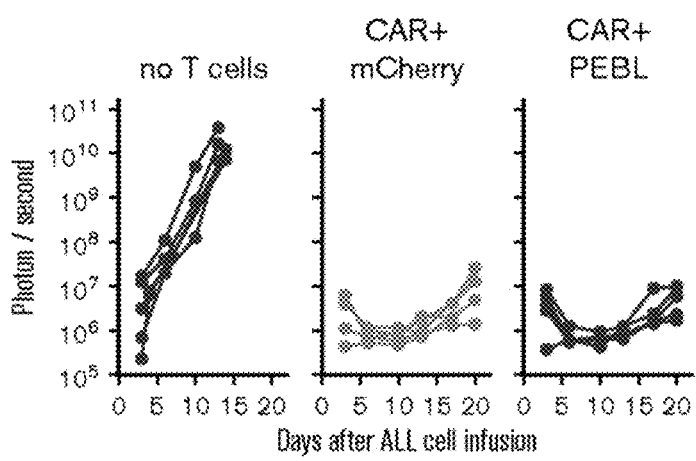
Figure 7C:
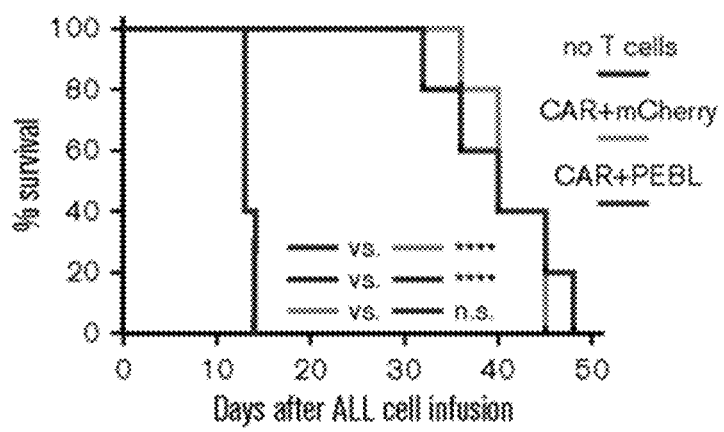
Figure 7D:
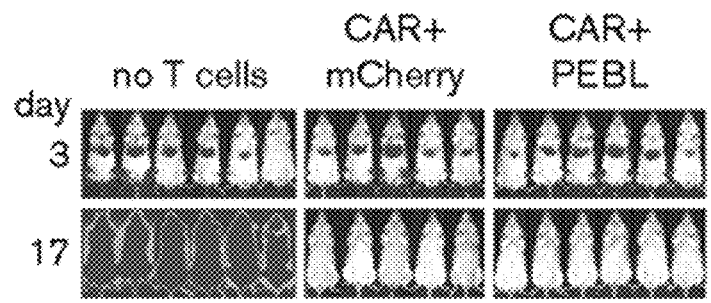
Figure 7E:
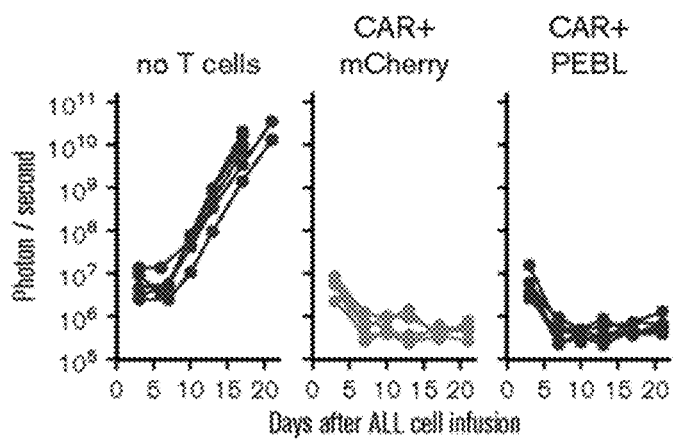
Figure 7F:
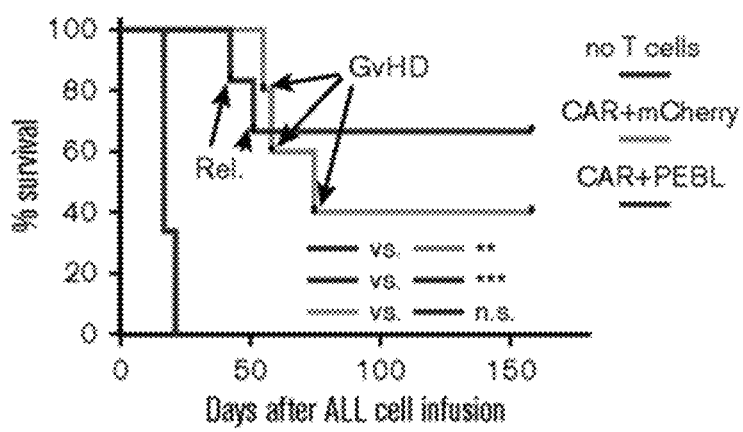

Results of in vitro experiments indicated that PEBL-transduced T cells expressing anti-CD19 CAR retained CAR-mediated cytotoxic capacity. Thus, we tested their antileukemic capacity in a xenograft ALL model. As shown in FIGS. 7A-7C, leukemia cell growth occurred in all untreated control mice, whereas CAR+PEBL-T cells effectively killed Nalm6 leukemic cells at rates that overlapped those of CAR-T cells transduced with mCherry instead of anti-CD3ε PEBL. In a third model, we combined the conditions of the previous 2. After injecting mice with Nalm6 cells and assessing engraftment, mice were irradiated at 2.5 Gy and then treated with CAR-T cells, either transduced with PEBL or with mCherry alone. As shown in FIGS. 7D-7E, all untreated control mice developed leukemia regardless of irradiation, whereas CAR-T cells markedly reduced leukemia burden. Notably, 3 of the 5 mice who received CAR-T cells without PEBL developed GVHD (>20% weight loss, fur loss, reduced mobility), whereas none of the 6 that received CAR+PEBL T cells did (FIG. 7F). The remaining 2 mice in the CAR+mCherry group, and 4 of the 6 mice that received CAR+PEBL T cells, remain in remission more than 150 days after leukemia cell engraftment (FIG. 7F).

Discussion

We developed a method that allows rapid and efficient downregulation of CD3/TCRαβ in T cells. Anti-CD3ε PEBL transduction caused intracellular retention of CD3ε, which, in turn, prevented expression of TCRαβ on the surface of T lymphocytes. We identified PEBL constructs that had minimal or no extracellular leakage and were highly effective at blocking TCRαβ signaling. PEBL-T cells transduced with an antiviral TCR were unable to respond to a cognate viral peptide; PEBL transduction markedly lessened the capacity of human T cells to cause GVHD in mice. PEBL expression and CD3/TCRαβ downregulation was durable; it did not affect expression of other surface molecules, T-cell survival, or proliferation. Importantly, PEBL-T cells responded normally to CAR signaling and killed CAR-targeted ALL cells in vitro and in vivo. a KDEL sequence (SEQ ID NO:32), KKD/E sequence KKMP sequence (SEQ ID NO:33), YQRL sequence (SEQ ID NO:34), or KKXX sequence, wherein X is any amino acid sequence (SEQ ID NO:35).

The best PEBLs in our study contained either the KDEL (SEQ ID NO:32) or KKXX [SEQ ID NO:35; such as, but not limited to, KKMP (SEQ ID NO:33) or KKTN (SEQ ID NO:43)] retention domains, which anchor associated luminal ER proteins, preventing their secretion or membrane expression.[32,33] Thus, our anti-CD3ε PEBLs blocked CD3ε assembly with the other components of the CD3/TCRαβ complex and its surface expression. KDEL peptides (such as SEKDEL, SEQ ID NO:50) have been previously linked to scFv to block protein expression with varying efficiency in experiments performed primarily with cell lines.[31,34] A protein trafficking study found that the amino acids in positions −5 and −6 beyond KDEL were important in the ER localization of soluble proteins.[35] In the PEBL context, we found that the intervening sequence between scFv and KDEL was critical for its function and identified sequences that improved protein retaining compared with SEKDEL. Protein trafficking studies had also indicated that carboxyl-terminal KKXX motifs direct ER localization and that KKXX positioning in relation to the membrane was critical for its effective function.[36] We found that the KKXX motif linked to the CD8α transmembrane domain constituted a robust anchoring platform for PEBLs, and that the spacer between these 2 components affected PEBL function.

Because we did not directly target TCRα or TCRβ chains, a potential concern is that low levels of TCRαβ, undetectable by flow cytometry but sufficient to induce signals, may still persist. We found, however, that T cells transduced with anti-CD3ε PEBL were generally nonresponsive to TCR-mediated signaling. Although it is possible that retention of CD3/TCR and/or PEBL could lead to their accumulation and stress response, we have been unable to detect any deleterious effects. In addition to observing normal growth of PEBL-transduced CD3/TCR-negative Jurkat cells for nearly 2 years, there was no defect in the proliferative and cytotoxic potential of PEBL-transduced T cells. Conceivably, the murine-derived scFv of PEBLs might accelerate rejection of the infused CAR-T cells. This concern, however, could be addressed by using a scFv of human origin, as has been reported for the scFv contained in CARs.[37]

Contemporary gene editing methods have interesting applications in CAR-T-cell therapy.[15,18,20] For example, CRISPR/Cas9 was recently used to insert the anti-CD19 CAR gene into the TCRα-constant (TRAC) locus, eliminating TCRαβ expression.[19,38] One of the advantages of the PEBL method is that it does not require major modifications of current protocols for clinical-grade large-scale cell processing. Because the anti-CD3 PEBL gene can be combined with the CAR gene in a single bicistronic construct, an allogeneic CAR-T cell product can be obtained after a single transduction procedure. Manufacturing T cells with PEBL and CAR expression relies on viral vector and gene components that are essentially identical to those used for CAR expression in current clinical trials. Therefore, this approach is unlikely to raise safety concerns beyond those related to standard CAR expression; uncertainties regarding the application of gene editing methodologies do not pertain. That notwithstanding, the PEBL approach can also be combined with gene editing methods to engineer CAR-T cells resistant to rejection and with higher potency.[15,39,40] Another application is to block expression of T-cell antigens shared by normal and malignant T cells, thus avoiding CAR-mediated fratricide while targeting T-cell leukemias and lymphomas.[41]

Clinical results with autologous CAR-T cells have demonstrated their extraordinary potential.[1-10] A critical next step for this technology is to improve its consistency and manufacturing, so that patients can have access to uniformly robust and timely products. To this end, methods to reliably generate allogeneic CAR-T cells are an important advance. Allogeneic cells can be available regardless of the patient immune cell status and his/her fitness to undergo apheresis.

CAR-T cells could be prepared with the optimal cellular composition, high CAR expression, and maximum functional potency. Clinical observations and experimental data suggest that the risk for GVHD with allogeneic CAR-T cells may be lower than expected if CARs rely on CD28 costimulation and are infused in HLA-matched recipients.[42-45] This, however, may not extend to other CARs and/or different transplant settings. Thus, grade II GVHD was reported in 2 of 3 patients who received infusion of CD137 costimulated donor CAR-T cells,[46] and grade II/III GVHD in 3 of 6 patients who received infusion of haploidentical CAR-T cells costimulated with CD28, CD137, and CD27.[47] In these studies, GVHD required administration of corticosteroids, which are likely to eliminate the CAR-T cells. Regardless of the relative merits of different costimulatory molecules in terms of clinical efficacy and toxicity,[48] lack of TCRαβ expression reportedly can enhance antitumor activity of CAR-T cells.[19] Interestingly, in our tests of long-term cytotoxicity in vitro, T cells transduced with PEBL plus CAR performed better than those with CAR alone, in agreement with this observation. Overall, removing CD3/TCRαβ from allogeneic CAR-T cells products is likely to be advantageous, particularly if it can be accomplished with minimal disruption of established manufacturing protocols.

REFERENCES

1. Kochenderfer J N, Wilson W H, Janik J E, Dudley M E, Stetler-Stevenson M, Feldman S A, et al. Eradication of B-lineage cells and regression of lymphoma in a patient treated with autologous T cells genetically engineered to recognize CD19. Blood 2010 Nov. 18; 116(20): 4099-4102.
2. Porter D L, Levine B L, Kalos M, Bagg A, June C H. Chimeric antigen receptor-modified T cells in chronic lymphoid leukemia. N Engl J Med 2011; 365(8): 725-733.
3. Maude S L, Frey N, Shaw P A, Aplenc R, Barrett D M, Bunin N J, et al. Chimeric antigen receptor T cells for sustained remissions in leukemia. N Engl J Med 2014 Oct. 16; 371(16): 1507-1517.
4. Davila M L, Riviere I, Wang X, Bartido S, Park J, Curran K, et al. Efficacy and toxicity management of 19-28z CAR-T cell therapy in B cell acute lymphoblastic leukemia. Science Transl Med 2014 Feb. 19; 6(224): 224ra225.
5. Kochenderfer J N, Dudley M E, Kassim S H, Somerville R P, Carpenter R O, Stetler-Stevenson M, et al. Chemotherapy-refractory diffuse large B-cell lymphoma and indolent B-cell malignancies can be effectively treated with autologous T cells expressing an anti-CD19 chimeric antigen receptor. J Clin Oncol 2014 Aug. 25.
6. Lee D W, Kochenderfer J N, Stetler-Stevenson M, Cui Y K, Delbrook C, Feldman S A, et al. T cells expressing CD19 chimeric antigen receptors for acute lymphoblastic leukaemia in children and young adults: a phase 1 dose-escalation trial. Lancet 2014 Oct. 10.
7. Turtle C J, Hanafi L A, Berger C, Gooley T A, Cherian S, Hudecek M, et al. CD19 CAR-T cells of defined CD4+: CD8+ composition in adult B cell ALL patients. J Clin Invest 2016 Jun. 1; 126(6): 2123-2138.
8. Neelapu S S, Locke F L, Bartlett N L, et al. Axicabtagene Ciloleucel CAR T-cell therapy in refractory large B-cell lymphoma. N Engl J Med. 2017; 377(26):2531-2544.
9. Schulester et al. Chimeric antigen receptor T cells in refractory B-cell lymphomas. N. Engl J Med. 2017; 377(26):2545-2554.
10. Sadelain M, Riviere I, Riddell S. Therapeutic T cell engineering. Nature 2017 May 24; 545(7655): 423-431.
11. Rosenberg S A, Restifo N P. Adoptive cell transfer as personalized immunotherapy for human cancer. Science 2015 Apr. 3; 348(6230): 62-68.
12. Park J H, Geyer M B, Brentjens R J. CD19-targeted CAR T-cell therapeutics for hematologic malignancies: interpreting clinical outcomes to date. Blood 2016 Jun. 30; 127(26): 3312-3320.
13. Appelbaum F R. Haematopoietic cell transplantation as immunotherapy. Nature 2001; 411(6835): 385-389.
14. Bleakley M, Riddell S R. Molecules and mechanisms of the graft-versus-leukaemia effect. Nature Rev Cancer 2004 May; 4(5): 371-380.
15. Poirot L, Philip B, Schiffer-Mannioui C, Le Clerre D, Chion-Sotinel I, Derniame S, et al. Multiplex Genome-Edited T-cell Manufacturing Platform for "Off-the-Shelf" Adoptive T-cell Immunotherapies. Cancer Res 2015 Sep. 15; 75(18): 3853-3864.
16. Yang et al., Challenges and opportunities of allogeneic donor-derived CAR T cells. Curr Opin Hematol. 2015; 22(6): 5095-515.
17. Boettcher M, McManus M T. Choosing the right tool for the job: RNAi, TALEN, or CRISPR. Mol Cell 2015 May 21; 58(4): 575-585.
18. Torikai H, Reik A, Liu P Q, Zhou Y, Zhang L, Maiti S, et al. A foundation for universal T-cell based immunotherapy: T cells engineered to express a CD19-specific chimeric-antigen-receptor and eliminate expression of endogenous TCR. Blood 2012 Jun. 14; 119(24): 5697-5705.
19. Eyquem J, Mansilla-Soto J, Giavridis T, van der Stegen S J, Hamieh M, Cunanan K M, et al. Targeting a CAR to the TRAC locus with CRISPR/Cas9 enhances tumour rejection. Nature 2017 Mar. 2; 543(7643): 113-117.
20. Qasim W, Zhan H, Samarasinghe S, Adams S, Amrolia P, Stafford S, et al. Molecular remission of infant B-ALL after infusion of universal TALEN gene-edited CAR T cells. Science translational medicine 2017 Jan. 25; 9(374).
21. Manabe A, Coustan-Smith E, Kumagai M, Behm F G, Raimondi S C, Pui C H, et al. Interleukin-4 induces programmed cell death (apoptosis) in cases of high-risk acute lymphoblastic leukemia. Blood 1994; 83(7): 1731-1737.
22. Imai C, Mihara K, Andreansky M, Nicholson I C, Pui C H, Campana D. Chimeric receptors with 4-1BB signaling capacity provoke potent cytotoxicity against acute lymphoblastic leukemia. Leukemia 2004; 18: 676-684.
23. Kudo K, Imai C, Lorenzini P, Kamiya T, Kono K, Davidoff A M, et al. T lymphocytes expressing a CD16 signaling receptor exert antibody-dependent cancer cell killing. Cancer Res 2014 Jan. 1; 74(1): 93-103.
24. Shimasaki N, Fujisaki H, Cho D, Masselli M, Lockey T, Eldridge P, et al. A clinically adaptable method to enhance the cytotoxicity of natural killer cells against B-cell malignancies. Cytotherapy 2012 August; 14(7): 830-40.
26. Shimasaki N, Campana D. Natural killer cell reprogramming with chimeric immune receptors. Methods Mol Biol 2013; 969: 203-220.
27. Koh S, Shimasaki N, Suwanarusk R, Ho Z Z, Chia A, Banu N, et al. A practical approach to immunotherapy of hepatocellular carcinoma using T cells redirected against hepatitis B virus. Mol Ther Nucleic Acids 2013; 2: e114.
28. Alarcon B, Berkhout B, Breitmeyer J, Terhorst C. Assembly of the human T cell receptor-CD3 complex takes place in the endoplasmic reticulum and involves intermediary complexes between the CD3-gamma delta epsilon core and single T cell receptor alpha or beta chains. J Biol Chem 1988 Feb. 25; 263(6): 2953-2961.

29. Clevers H, Alarcon B, Wileman T, Terhorst C. The T cell receptor/CD3 complex: a dynamic protein ensemble. Annu Rev Immunol 1988; 6: 629-662.
30. Weiss A. Molecular and genetic insights into T cell antigen receptor structure and function. Annu Rev Genet 1991; 25: 487-510.
31. Marasco et al., Design, intracellular expression, and activity of a human anti-humna immunodeficiency virus type 1 gp120 single-chain antibody. Proc Natl Acad Sci USA. 1993; 90(16): 7889-7893.
32. Munro S, Pelham H R. A C-terminal signal prevents secretion of luminal E R proteins. Cell 1987 Mar. 13; 48(5): 899-907.
33. Jackson M R, Nilsson T, Peterson P A. Identification of a consensus motif for retention of transmembrane proteins in the endoplasmic reticulum. EMBO J 1990 October; 9(10): 3153-3162.
34. Marschall A L, Dubel S, Boldicke T. Specific in vivo knockdown of protein function by intrabodies. mAbs 2015; 7(6): 1010-1035.
35. Alanen et al., Beyond KDEL: the role of positions 5 and 6 in determining ER localization. J Mol Biol. 2011; 409(3): 291-297.
36. Shikano et al., Membrane receptor trafficking: evidence of proximal and distal zones conferred by two independent endoplasmic reticulum localization signals. Proc Natl Acad Sci USA. 2003; 100(10): 5783-5788.
37. Sommermeyer et al., Fully human CD19-specific chimeric antigen receptors for T-cell therapy. Leukemia, 2017; 31(10): 2191-2199.
38. MacLeod D T, Antony J, Martin A J, Moser R J, Hekele A, Wetzel K J, et al. Integration of a CD19 CAR into the TCR alpha chain locus streamlines production of allogeneic gene-edited CART cells. Mol Ther 2017 Apr. 5; 25(4): 949-961.
39. Schumann K, Lin S, Boyer E, Simeonov D R, Subramaniam M, Gate R E, et al. Generation of knock-in primary human T cells using Cas9 ribonucleoproteins. Proc Natl Acad Sci USA 2015 Aug. 18; 112(33): 10437-10442.
40. Su S, Hu B, Shao J, Shen B, Du J, Du Y, et al. CRISPR-Cas9 mediated efficient PD-1 disruption on human primary T cells from cancer patients. Sci Reports. 2016; 6(1): 20070.
41. Png et al., Blockade of CD7 expression in T cells for effective chimeric antigen receptor targeting of T-cell malignancies. Blood Adv, 2017; 1(25): 2348-2360.
42. Kochenderfer J N, Dudley M E, Carpenter R O, Kassim S H, Rose J J, Telford W G, et al. Donor-derived CD19-targeted T cells cause regression of malignancy persisting after allogeneic hematopoietic stem cell transplantation. Blood 2013 Dec. 12; 122(25): 4129-4139.
43. Brudno et al., Allogeneic T cells that express an anti-CD19 chimeric antigen receptor induce remissions of B-cell malignancies that progress after allogeneic hematopoietic stem-cell transplantation without causing graft-versus-host disease. J Clin Oncol. 2016; 34(10): 1112-1121.
44. Ghosh A, Smith M, James S E, Davila M L, Velardi E, Argyropoulos K V, et al. Donor CD19 CAR T cells exert potent graft-versus-lymphoma activity with diminished graft-versus-host activity. Nat Med 2017 Feb.; 23(2): 242-249.
45. Anwer et al., Donor origin CAR T cells: graft versus malignancy effect without GVHD, a systemic review. Immunotherapy. 2017; 9(2): 123-130.
46. Dai et al., Tolerance and efficacy of autologous or donor-derived T cells expression CD19 chimeric antigen receptors in adult B-ALL with extramedullary leukemia. OncoImmunology. 2015; 4(11): e1027469.
47. Chen et al., Donor-derived CD19-targeted T cell infusion induces minimal residual disease-negative remission in relapsed B-cell acute lymphoblastic leukaemia with no response to donor lymphocyte infusions after haploidentical haematopoietic stem cell transplantation. Br J Haematol. 2017; 179(4): 598-605.
48. Campana D, Schwarz H, Imai C. 4-1B B chimeric antigen receptors. Cancer J 2014 March-April; 20(2): 134-140.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

---

What is claimed is:

1. A method of treating a CD19-positive or a CD3-positive cancer in a patient in need thereof, comprising administering a therapeutically effective amount of engineered CD3/TCRαβ-deficient T cells to the patient,
wherein the engineered CD3/TCRαβ-deficient T cells comprise:
(i) a chimeric antigen receptor (CAR) that binds CD3 or CD19; and
(ii) a polypeptide comprising a target-binding molecule connected by a linker to a localizing domain,
wherein the target-binding molecule comprises an antibody that binds a CD3/TCRαβ complex protein,
wherein
a) the linker comprises (GGGGS)$_n$ (SEQ ID NO: 36), wherein n is an integer of from 2 to 12 and the localizing domain comprises SEQ ID NO:32, or
b) the linker and localizing domain together comprise SEQ ID NO: 12 or SEQ ID NO: 15, and
wherein the polypeptide comprising the target-binding molecule connected by a linker to the localizing domain is not secreted by the engineered CD3/TCRαβ-deficient T cells.

2. The method of claim 1, wherein the antibody is a single chain variable fragment (scFv) that binds the CD3/TCRαβ complex protein selected from the group consisting of TCRα, TCRβ, CD3ε, CD3δ, CD3γ, and CD3ζ.

3. The method of claim 2, wherein the scFv comprises a variable heavy chain (V$_H$) sequence having at least 95% sequence identity to SEQ ID NO:1 and a variable light chain (V$_L$) sequence having at least 95% sequence identity to SEQ ID NO:2.

4. The method of claim 1, wherein the CAR comprises an anti-CD3 scFv domain, a 4-1BB stimulatory signaling domain, and a CD3ζ signaling domain.

5. The method of claim 1, wherein the CAR comprises an anti-CD19 scFv domain, a 4-1BB stimulatory signaling domain, and a CD3t signaling domain.

6. The method of claim 1, wherein T cell is selected from the group consisting of a cytotoxic T cell, a helper T cell, a regulatory T cell, an effector T cell, a memory T cell, a natural killer T cell, and a gamma delta T cell.

7. The method of claim 1, wherein the CD19-positive or a CD3-positive cancer is a hematopoietic cancer.

8. The method of claim 7, wherein the hematopoietic cancer is selected from the group consisting of acute myeloid leukemia, chronic myelogenous leukemia, myelodysplasia, acute lymphoblastic leukemia, chronic lymphocytic leukemia, multiple myeloma, Hodgkin lymphoma, and non-Hodgkin lymphoma.

9. A method of reducing or eliminating the likelihood of graft-versus-host disease in an individual receiving therapeutic T cell treatment, comprising administering engineered CD3/TCRαβ-deficient T cells to the individual, wherein the engineered CD3/TCRαβ-deficient T cells comprise a polypeptide comprising a target-binding molecule connected by a linker to a localizing domain,
wherein the target-binding molecule comprises an antibody that binds a CD3/TCRαβ complex protein,
wherein
a) the linker comprises (GGGGS)n (SEQ ID NO: 36), wherein n is an integer of from 2 to 12 and the localizing domain comprises SEQ ID NO:32, or
b) the linker and localizing domain together comprise SEQ ID NO: 12 or SEQ ID NO: 15, and
wherein the polypeptide comprising the target-binding molecule connected by a linker to the localizing domain is not secreted by the engineered CD3/TCRαβ-deficient T cells.

10. The method of claim 1 or claim 9, wherein the linker comprises (GGGGS)$_4$ (SEQ ID NO: 37).

11. The method of claim 1 or claim 9, wherein the linker comprises (GGGGS)$_2$ (SEQ ID NO: 39).

12. The method of claim 9, wherein the antibody is a single chain variable fragment (scFv) that binds the CD3/TCRαβ complex protein selected from the group consisting of TCRα, TCRβ, CD3ε, CD3δ, CD3γ, and CD3ζ.

13. The method of claim 12, wherein the scFv comprises a variable heavy chain (V$_H$) sequence having at least 95% sequence identity to SEQ ID NO:1 and a variable light chain (V$_L$) sequence having at least 95% sequence identity to SEQ ID NO:2.

14. The method of claim 9, wherein the CAR comprises an anti-CD3 scFv domain, a 4-1BB stimulatory signaling domain, and a CD3ζ signaling domain.

15. The method of claim 9, wherein the CAR comprises an anti-CD19 scFv domain, a 4-1BB stimulatory signaling domain, and a CD3ζ signaling domain.

16. The method of claim 9, wherein T cell is selected from the group consisting of a cytotoxic T cell, a helper T cell, a regulatory T cell, an effector T cell, a memory T cell, a natural killer T cell, and a gamma delta T cell.

* * * * *